United States Patent
Kadiyala et al.

(10) Patent No.: US 12,430,737 B1
(45) Date of Patent: Sep. 30, 2025

(54) AGRICULTURAL SYSTEM

(71) Applicant: Kubota Corporation, Osaka (JP)

(72) Inventors: Srikanth Kadiyala, Fremont, CA (US);
Masaya Mori, Fremont, CA (US);
Kenta Nakamura, Fremont, CA (US);
Kotaro Shimada, Fremont, CA (US)

(73) Assignee: KUBOTA CORPORATION, Osaka (JP)

( * ) Notice: Subject to any disclaimer, the term of this patent is extended or adjusted under 35 U.S.C. 154(b) by 0 days.

(21) Appl. No.: 19/047,938

(22) Filed: Feb. 7, 2025

(51) Int. Cl.
| | |
|---|---|
| G06T 7/00 | (2017.01) |
| G01N 21/27 | (2006.01) |
| G01N 33/02 | (2006.01) |
| H04N 13/204 | (2018.01) |
| H04N 23/13 | (2023.01) |
| H04N 23/695 | (2023.01) |
| H04N 23/90 | (2023.01) |

(52) U.S. Cl.
CPC ........... *G06T 7/0002* (2013.01); *G01N 21/27* (2013.01); *G01N 33/025* (2013.01); *H04N 13/204* (2018.05); *H04N 23/13* (2023.01); *H04N 23/695* (2023.01); *H04N 23/90* (2023.01); *G06T 2200/04* (2013.01); *G06T 2200/24* (2013.01); *G06T 2207/30168* (2013.01); *G06T 2207/30188* (2013.01); *G06T 2207/30252* (2013.01)

(58) Field of Classification Search
CPC .... H04N 13/204; H04N 23/695; H04N 23/90; H04N 23/13; G01N 21/27; G01N 33/025; G06T 7/0002; G06T 2200/04; G06T 2200/24; G06T 2207/30168; G06T 2207/30188
USPC .............................. 348/46, 47, 61
See application file for complete search history.

(56) References Cited

U.S. PATENT DOCUMENTS

| | | | | |
|---|---|---|---|---|
| 12,088,773 | B1* | 9/2024 | Kanagaraj | G06V 10/26 |
| 2015/0109410 | A1* | 4/2015 | Bonefas | G06F 18/22 |
| | | | | 348/43 |
| 2024/0233302 | A1* | 7/2024 | Babu | G05D 1/0278 |
| 2024/0236447 | A1* | 7/2024 | Kadiyala | H04N 23/11 |
| 2024/0276914 | A1* | 8/2024 | Bothe | A01D 45/10 |
| 2024/0281997 | A1* | 8/2024 | Bharathwaj | G06V 10/44 |

* cited by examiner

*Primary Examiner* — Thai Q Tran
(74) *Attorney, Agent, or Firm* — Keating & Bennett, LLP

(57) ABSTRACT

A quality measurement system includes a first camera, a second camera, a display device, and a controller. The controller is configured or programmed to control the first camera to acquire a first image that includes agricultural items and to determine, from the first image, one of the agricultural items that is suitable for measuring quality. The controller is configured or programmed to control the second camera to acquire measurement data of the one of the agricultural items. The controller is configured or programmed to store estimation models for calculating at least one quality score based upon the measurement data acquired by the second camera and to select one of the estimation models according to the one of the agricultural items. The controller is configured or programmed to calculate the at least one quality score of the one of the agricultural items based upon the selected one of the estimation models.

18 Claims, 37 Drawing Sheets

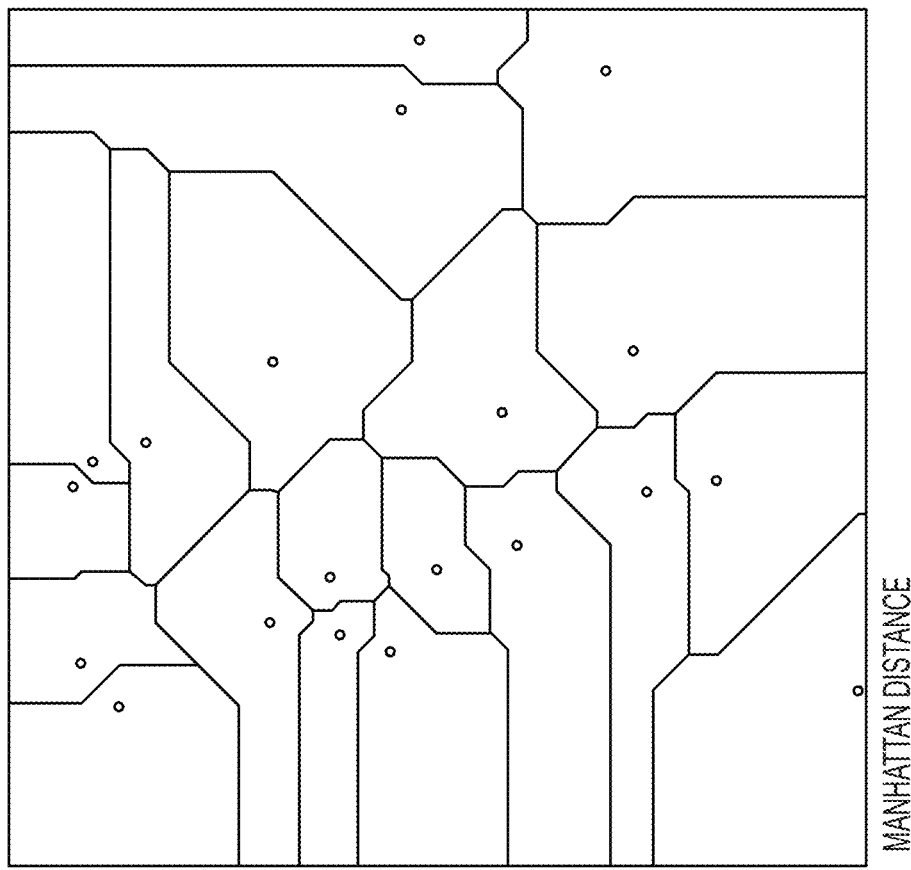
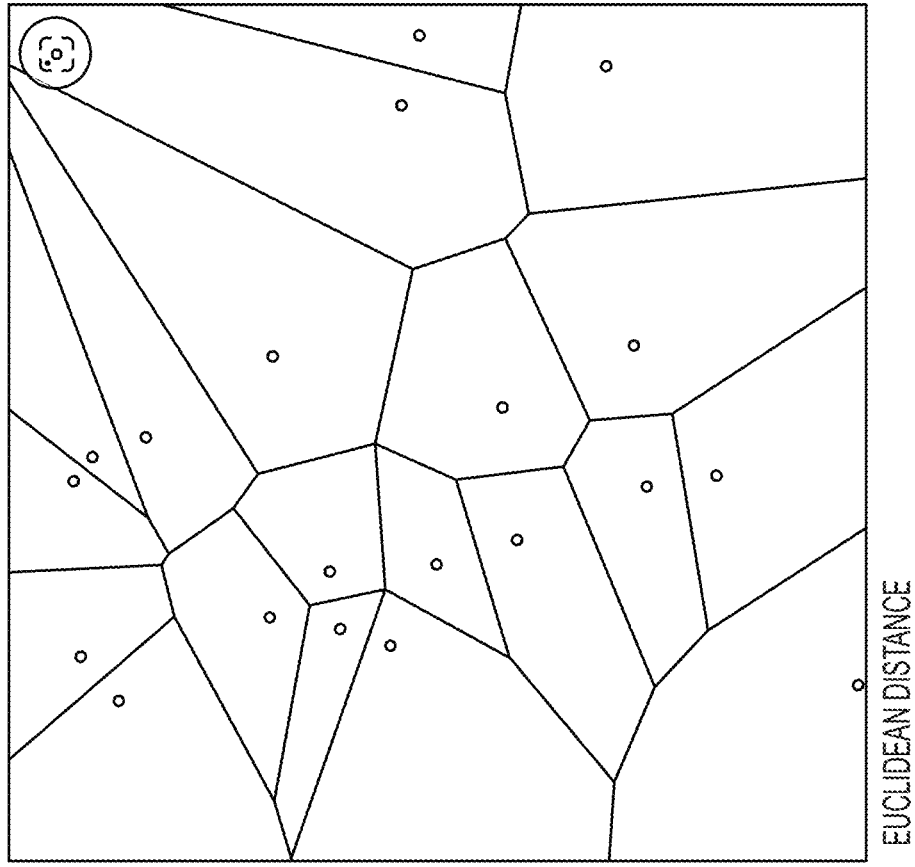
FIG. 20B
FIG. 20A

PATH INFORMATION

GENERAL INFORMATION
FIELD GROUP NAME : FREMONT OFFICE
VARIETY : CARBERNET SAUVIGNON
CLONE : 47.5
ROOTSTOCK : 0.35-36
TRELLIS : VSP
YEAR PLANTED : 2010

FIELD BLOCK INFORMATION
FIELD BLOCK NAME : FIELD BLOCK 1
NO. OF ROWS : 46
TOTAL NO. OF VINES : 246
BLOCK AREA : 3 ACRES

WORK AREA INFORMATION
START ROW INDEX : 1
END ROW INDEX : 1
START POINT : CORNER 1
END POINT : CORNER 4
PATH MODE : PART
NO. OF VINES IN W/A : 14 ACRES

600

MACHINE
ROVER_GRAPEQUALITY
○ ONLINE
📶
🔋 69%
📷 GRAPE QUALITY
GOOD

610

TASK PARAMETERS
GRAPE VARIETY : CHARDONNAY
MEASURE DRY BUNCH : OFF
✱ AVOID SPIDER WEB : OFF
AVOID MOLD : OFF
AVOID SUNBURNED : OFF
SAMPLING RATE : 7%
SAMPLING MODE : RANDOM MODE

620

630

EXECUTE

*FIG. 27*

AGRICULTURAL SYSTEM

BACKGROUND OF THE INVENTION

1. Field of the Invention

The present invention relates to an agricultural system.

2. Description of the Related Art

Conventionally, agricultural systems that include a hyperspectral imaging (HSI) camera are used to scan a plurality of agricultural items (e.g., a plurality of grape bunches). When a plurality of agricultural items are present, the agricultural system can use the hyperspectral imaging to scan each of the plurality of agricultural items, or arbitrarily select one or more of the plurality of agricultural items to be scanned.

For the foregoing reasons, there is a need for an agricultural system that can be reliably and efficiently used to sample agricultural items.

SUMMARY OF THE INVENTION

Preferred embodiments of the present invention are directed to a system that can reliably be used to reliably and efficiently sample agricultural items.

A quality measurement system includes a first camera, a second camera, a display device, and a controller. The controller is configured or programmed to control the first camera to acquire a first image that includes a plurality of agricultural items. The controller is configured or programmed to determine, from the first image, one of the plurality of agricultural items that is suitable for measuring quality. The controller is configured or programmed to control the second camera to acquire measurement data of the one of the plurality of agricultural items. The controller is configured or programmed to store a plurality of estimation models for calculating at least one quality score based upon the measurement data acquired by the second camera. The controller is configured or programmed to select one of the plurality of estimation models according to the one of the plurality of agricultural items. The controller is configured or programmed to calculate the at least one quality score of the one of the plurality of agricultural items based upon the selected one of the plurality of estimation models.

The controller can be configured or programmed to select the one of the plurality of estimation models according to a variety of the one of the plurality of agricultural items. The one of the plurality of agricultural items can be a grape bunch, and the controller can be configured or programmed to store predetermined relationships between plurality of estimation models and grape varieties. At least one of the plurality of estimation models can be associated with at least two grape varieties.

Each of the plurality of estimation models can be a calibration curve that associates wavelength intensity with the at least one quality score. The at least one quality score can include one or more of Brix, pH, and titratable acidity (TA).

The first camera can be a stereo camera, and the second camera can be an HSI (hyperspectral imaging) camera.

The controller can be configured or programmed to select the one of the plurality of estimation models according to a location of the quality measurement system.

A vehicle can include the quality measurement system, and the controller can be configured or programmed to control movement of the vehicle. The controller can be configured or programmed to control the vehicle to stop and remain stationary while the first camera acquires the first image. The controller can be configured or programmed to control the vehicle to stop and remain stationary while the second camera acquires the second image.

The vehicle can include at least one slider that is configured to move the second camera. The controller can be configured or programmed to control the at least one slider to move the second camera while the vehicle is stationary.

An agricultural system can include the vehicle and a display device that is operable by a user. The controller can be configured or programmed to determine the one of the plurality of agricultural items that is suitable for measuring quality in response to an input by the user of the display device. The display device can be configured to display a selection of varieties of the plurality of agricultural items. The display device can be configured to display selectable parameters for measuring the at least one quality score. The controller can be configured or programmed to receive operational parameters input by the user of the display device prior to controlling the vehicle to begin movement to the plurality of agricultural items.

BRIEF DESCRIPTION OF THE DRAWINGS

FIGS. 20A and 20B show example views of a first region of the application display of FIGS. 19A and 19B.

FIG. 27 shows an application display according to a preferred embodiment of the present invention that includes task parameters for sampling agricultural items.

DETAILED DESCRIPTION OF PREFERRED EMBODIMENTS

Figure 1:
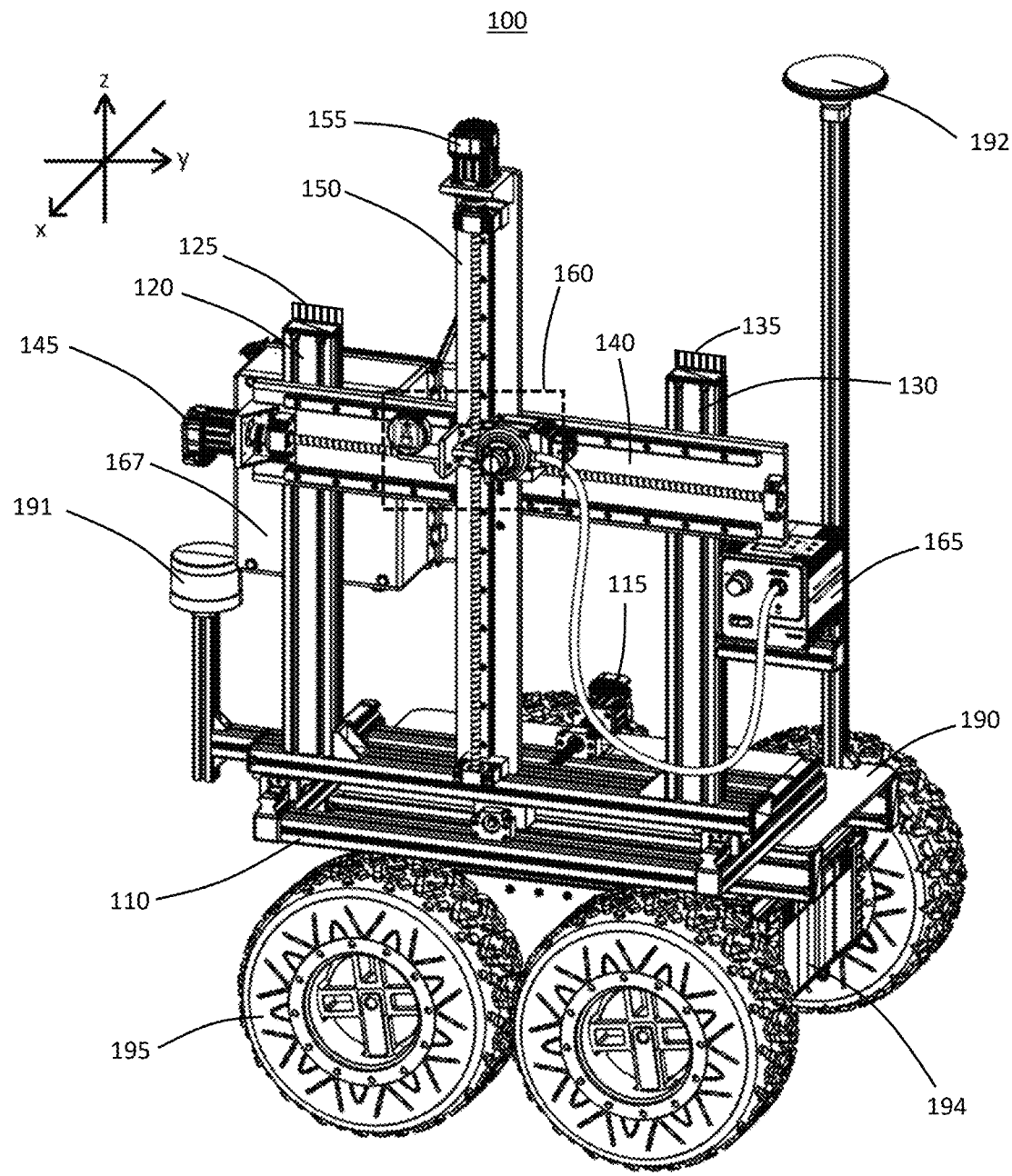
FIG. 1 shows a front perspective view of a cartesian arm system according to a preferred embodiment of the present invention.
Figure 2:
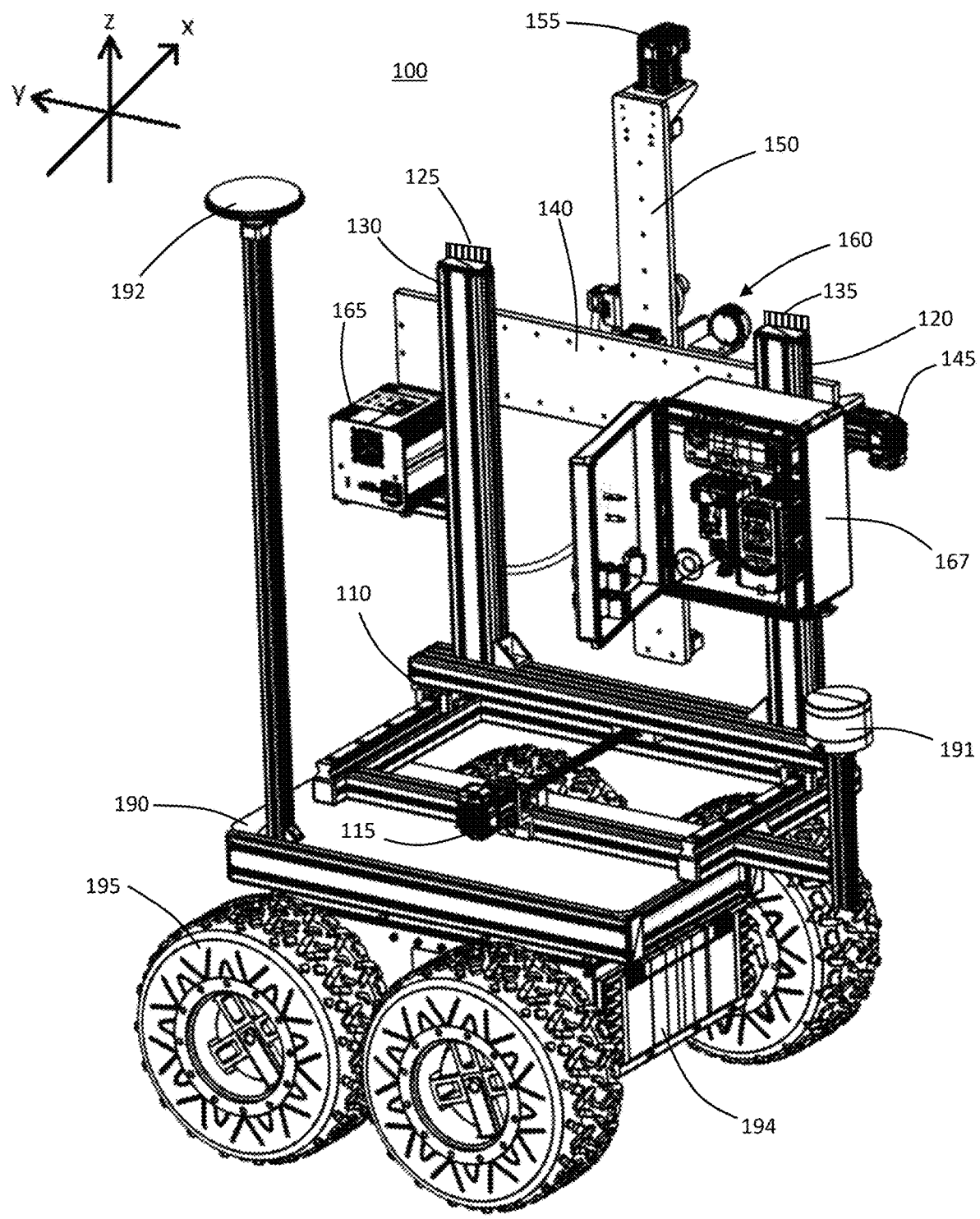
FIG. 2 shows a rear perspective view of the cartesian arm system shown in FIG. 1.

FIG. 1 shows a front perspective view of a cartesian arm system 100 according to a preferred embodiment of the present invention. As shown in FIG. 1, the cartesian arm system 100 can include a vehicle or the like. However, the cartesian arm system 100 can be mounted on a cart that is able to be towed by a vehicle or a person. FIG. 2 shows a rear perspective view of the cartesian arm system 100 of FIG. 1.

As shown in FIGS. 1 and 2, the cartesian arm system 100 includes a base frame 110, side frames 120 and 130, a horizontal frame 140, and a vertical frame 150. The side frames 120 and 130 are mounted to the base frame 110, and the side frames 120 and 130 directly support the horizontal frame 140. The vertical frame 150 is mounted on the horizontal frame 140. One or more devices 160, such as one or more cameras and/or light sources, can be mounted on the vertical frame 150. The cartesian arm system 100 is preferably able to support a payload of about 5 kg, for example.

The base frame 110 includes a base frame motor 115 that is able to move the side frames 120 and 130 along the base frame 110, such that the one or more devices 160 can be moved in a first direction (the x-axis shown in FIG. 1). The horizontal frame 140 includes a horizontal frame motor 145 that is able to move the vertical frame 150 along the horizontal frame 140, such that the one or more devices 160 can be moved in a second direction (the y-axis shown in FIG. 1). The vertical frame 150 includes a vertical frame motor 155 that is able to move the one or more devices 160 along the vertical frame 150 in a third direction (the z-axis shown in FIG. 1). Each of the base frame motor 115, the horizontal frame motor 145, and the vertical frame motor 155 can be a screw motor, for example. Screw motors can provide a relatively high level of precision to accurately move and locate the one or more devices 160. However, each of the base frame motor 115, the horizontal frame motor 145, and the vertical frame motor 155 can be any motor that provides a continuous torque greater than or equal to about 0.2 N m, and preferably any motor that provides a continuous torque greater than or equal to about 0.3 N m.

Each of the base frame motor 115, the horizontal frame motor 145, and the vertical frame motor 155 can be designed and/or sized according to an overall weight of the one or more devices 160. In addition, a coupler for each of the base frame motor 115, the horizontal frame motor 145, and the vertical frame motor 155 can be changed according to a motor shaft diameter and/or a corresponding mounting hole pattern.

The base frame 110 can be mounted on a base plate 190, and base electronics 194 can also be mounted to the base plate 190. A plurality of wheels 195 can be mounted to the base plate 190 or the base electronics 194. The plurality of wheels 195 can be controlled by the base electronics 194, and the base electronics 194 can include a power supply to drive an electric motor or the like. As an example, the plurality of wheels 195 can be driven by an electric motor with a target capacity of about 65 kW to about 75 kW and a power supply for the electric motor can be a battery with a capacity of about 100 kWh. The electric motor and the plurality of wheels can define a traveling device, for example.

The base electronics 194 can also include processor and memory components that are programmed or configured to perform autonomous navigation of the cartesian arm system 100. Furthermore, a LiDAR (light detection and ranging) system 191 and a Global Navigation Satellite System (GNSS) 192 can also be mounted to the base frame 110 or the base plate 190 so that position data of the cartesian arm system 100 can be determined. The LiDAR system 191 and GNSS 192 can be used for obstacle avoidance and navigation when the cartesian arm system 100 is autonomously moved. Preferably, for example, the cartesian arm system 100 can be implemented with a remote control interface, and can communicate via one or more of Ethernet, USB, wireless communications, and GPS RTK (real time kinematics). The remote control interface and communications devices can be included in one or both of the base electronics 194 and imaging electronics 167 (described below). The cartesian arm system 100 can also include, or be communicatively connected with, a display device to display data and/or images obtained by the one or more devices 160 and to display information provided by the base electronics 194 (for example, location, speed, battery life, and the like of the cartesian arm system 100).

Figure 3:
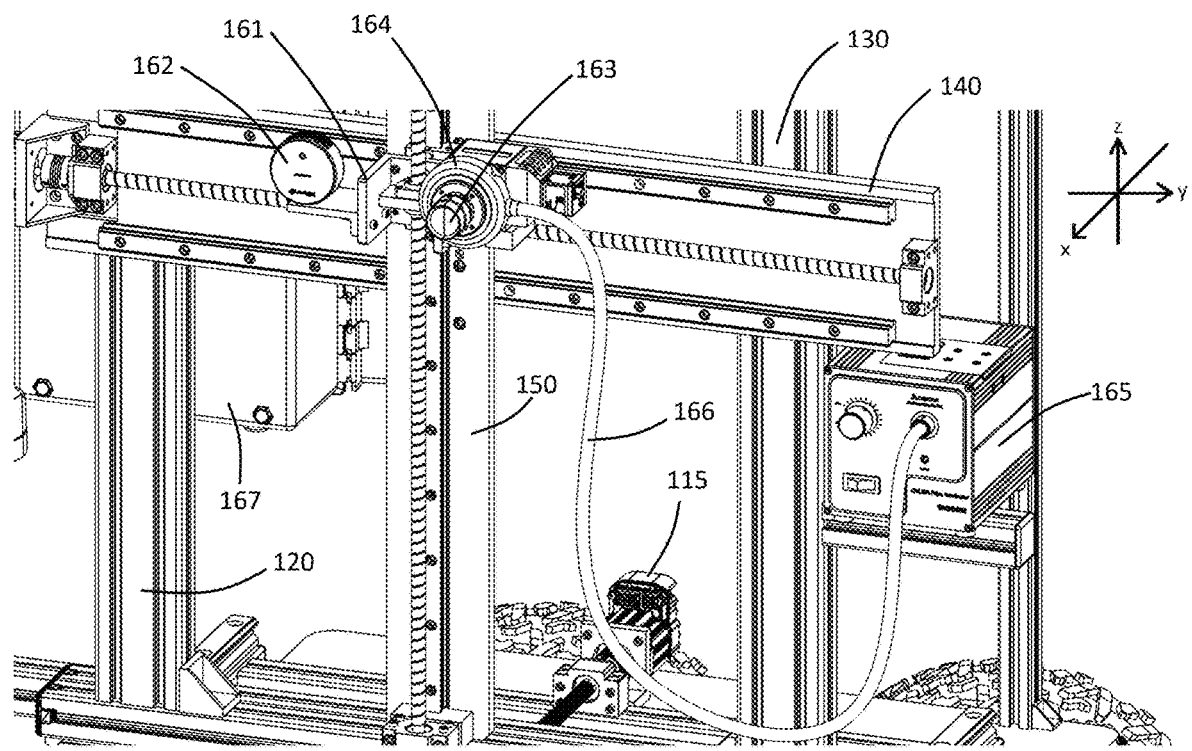
FIG. 3 shows a close-up view of a portion of the cartesian arm system shown in FIG. 1.

FIG. 3 is a close-up view of a portion of the cartesian arm system 100 that includes the one or more devices 160. As shown in FIG. 3, the one or more devices 160 can include a first camera 162, a second camera 163, and a camera light source 164 that are mounted to a bracket 161 attached to the vertical frame 150. Preferably, for example, the first camera 162 and the second camera 163 are mounted on different sides of the bracket 161 along the y-axis shown in FIG. 3 to balance a weight on the bracket 161 with respect to a mounting point on the vertical frame 150. Alternatively, the first camera 162 can be located at a fixed position, for example, on one of the side frames 120 and 130. As another alternative, the first camera 162 can be mounted to the horizontal frame 140 or to a second vertical frame that is separate from the vertical frame 150. That is, the first camera 162 can be mounted to a cartesian arm that is separate from the cartesian arm that moves the second camera 163.

The first camera 162 can be an RGB camera, a depth camera such as a LIDAR camera, a combined RGB camera and depth camera, a stereo camera, and the like. Preferably, for example, the first camera 162 is a camera that can provide both a relatively high resolution RGB image and relatively accurate depth information. The second camera 163 can be an HSI (hyperspectral imaging) camera, and the HSI camera can have a fixed focus length. The second camera 163 including an HSI camera is a non-limiting example of a quality measuring device. For example, a second camera 163 including a multi-spectral camera, an NRI sensor, a UV sensor, and an X-ray sensor are other non-limiting examples of a quality measuring device. The camera light source 164 can be a ring light that surrounds the second camera 163, and is preferably not mounted directly on the second camera 163 in order to prevent excessive warming of the second camera 163 from heat generated by the camera light source 164. Alternatively, the camera light source 164 can be mounted at a side of the second camera 163. The camera light source 164 can be connected to a light source supply 165. The camera light source 164 can include a halogen light source to provide a light spectrum for capturing HSI images, for example, in a range of about 400 nm to about 1000 nm. The light source supply 165 can be mounted to the side frame 130. The light source supply 165 can be connected to the camera light source 164 by a cable 166, and the cable 166 can include a fiber-optic cable. Preferably, for example, the cable 166 has a length of about three feet to provide sufficient length for movement of the one or more devices 160 while also significantly reducing or preventing a loss in the spectrum of the light output by the camera light source 164.

Preferably, for example, the cable 166 is a fiber-optic cable and has a length of about three feet or less to significantly reduce or prevent a loss in the spectrum of light output by the camera light source 164 while providing sufficient slack in the cable 166 to allow the one or more devices 160 full range of movement along each of the base frame 110, the horizontal frame 140, and the vertical frame 150. Preferably, for example, the cable 166 is provided to not be excessively bent or twisted, which may lead to a loss in the spectrum of light output by the camera light source 164.

The cartesian arm system 100 includes imaging electronics 167 that are mounted on side frame 120. The imaging electronics 167 can supply power to and control each of the base frame motor 115, the horizontal frame motor 145, and the vertical frame motor 155. That is, the imaging electronics 167 can include a power source to supply power to each of the base frame motor 115, the horizontal frame motor 145, and the vertical frame motor 155. In addition, the imaging electronics 167 can include processor and memory components that are programmed or configured to control each of the base frame motor 115, the horizontal frame motor 145, and the vertical frame motor 155. The processor and memory components of the imaging electronics 167 can also be configured or programmed to control the one or more devices 160, including the first camera 162, the second camera 163, the camera light source 164, and any light sources mounted on one or both of the side frames 120 and 130. In addition, the processor and memory components of the imaging electronics 167 can be configured or programmed to process image data obtained by the first camera 162 and the second camera 163.

As described above, the imaging electronics 167 and the base electronics 194 can include processors and memory components. The processors may be hardware processors, multipurpose processors, microprocessors, special purpose processors, digital signal processors (DPSs), and/or other types of processing components configured or programmed to process data. The memory components may include one or more of volatile, non-volatile, and/or replaceable data store components. For example, the memory components may include magnetic, optical, and/or flash storage components that may be integrated in whole or in part with the processors. The memory components may store instructions and/or instruction sets or programs that are able to be read and/or executed by the processors.

Preferably, for example, the imaging electronics 167 are mounted on the side arm 120 and the light source supply 165 is mounted on the side arm 130 to balance the overall weight of the cartesian arm system 100 along the y-axis shown in FIG. 1. That is, the imaging electronics 167 and the light source supply 165 are located to set a center of balance of the cartesian arm system 100 at a center portion of the base plate 190.

According to another preferred embodiment of the present invention, the imaging electronics 167 can be partially or completely implemented by the base electronics 194. For example, each of the base frame motor 115, the horizontal frame motor 145, and the vertical frame motor 155 can receive power from and/or be controlled by the base electronics 194 instead of the imaging electronics 167.

According to further preferred embodiments of the present invention, the imaging electronics 167 and the light source supply 165 can be connected to a power supply or power supplies that are separate from the base electronics 194. For example, a power supply can be included in one or both of the imaging electronics 167 and the light source supply 165. In addition, the base frame 110 may be detachably attached to the base plate 190, such that the base frame 110, the side frames 120 and 130, the horizontal frame 140, the vertical frame 150, and the components mounted thereto can be mounted on another vehicle or the like.

The base frame motor 115, the horizontal frame motor 145, and the vertical frame motor 155 are able to move the one or more devices 160 in three separate directions or along three separate axes. However, according to another preferred embodiment of the present invention, only a portion of the one or more devices 160 can be moved by the base frame motor 115, the horizontal frame motor 145, and the vertical frame motor 155, for example, only a second camera 163 or only the second camera 163 and the camera light source 164. Furthermore, the cartesian arm system 100 can be configured to linearly move the second camera 163 along only a single axis while the second camera 163 captures an image. For example, the horizontal frame motor 145 can be configured to linearly move the second camera 163 across a grape bunch while the second camera 163 captures an HSI image of the grape bunch.

A light source can be mounted on one or both of the side frames 120 and 130. For example, a light source 125 can be mounted to an upper portion of the side frame 120, and a light source 135 can be mounted to an upper portion of the side frame 130. The light sources 125 and 135 can include an LED light source that faces a same direction as the one or more devices 160, for example, along the x-axis shown in FIG. 1. The light sources 125 and 135 can provide illumination of an object or objects to be imaged by the first camera 162. For example, the light sources 125 and 135 can operate as a flash during daytime operation to compensate for ambient light when capturing images with the first camera 162. During nighttime operation, the light sources 125 and 135 can operate as either a flash for the first camera, or the light sources 125 and 135 can provide constant illumination for the first camera.

Figure 7A:
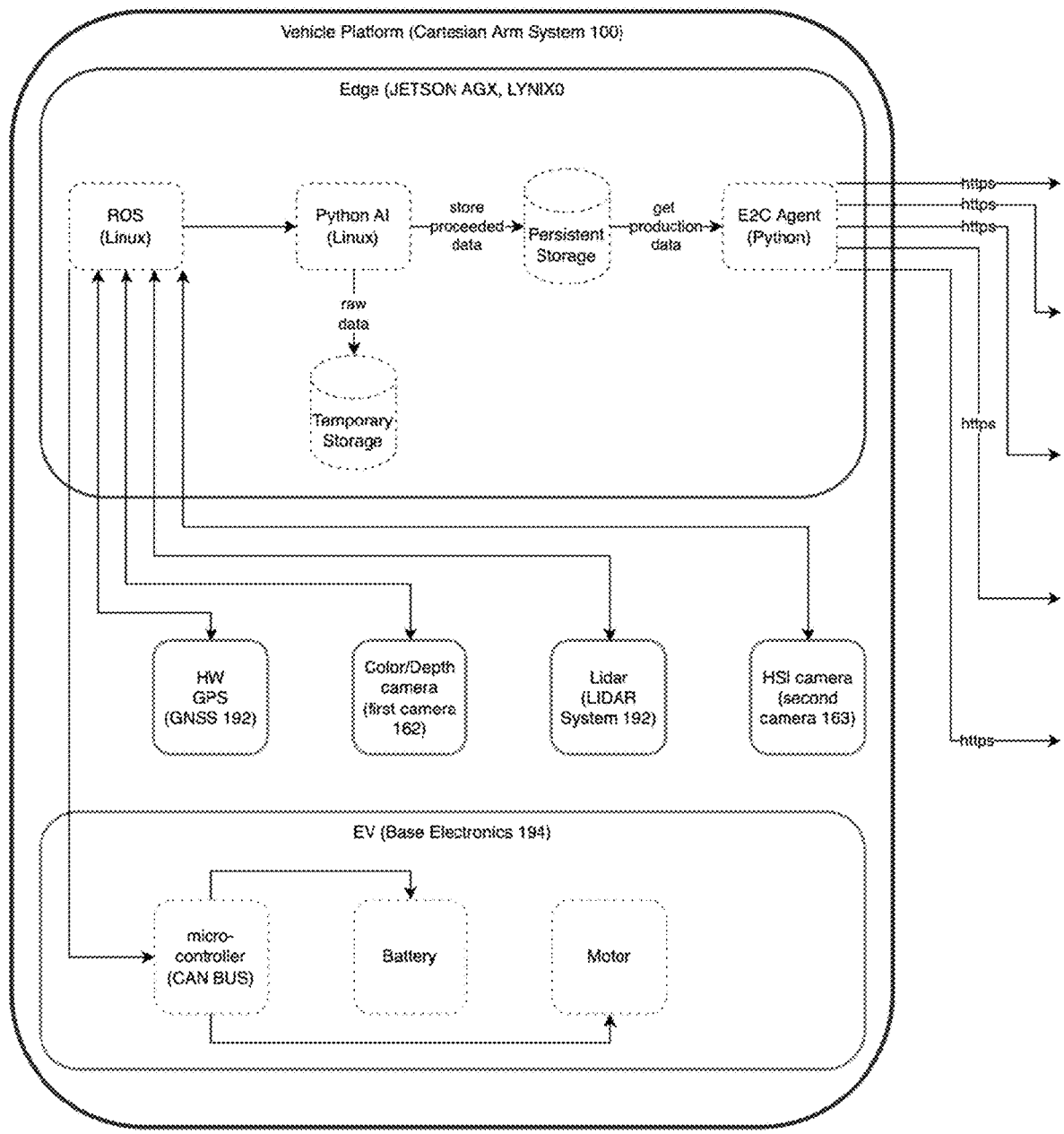
FIGS. 7A and 7B show an example of a block diagram of a cloud system that includes a vehicle platform, a cloud platform, and a user platform according to a preferred embodiment of the present invention.
Figure 7B:
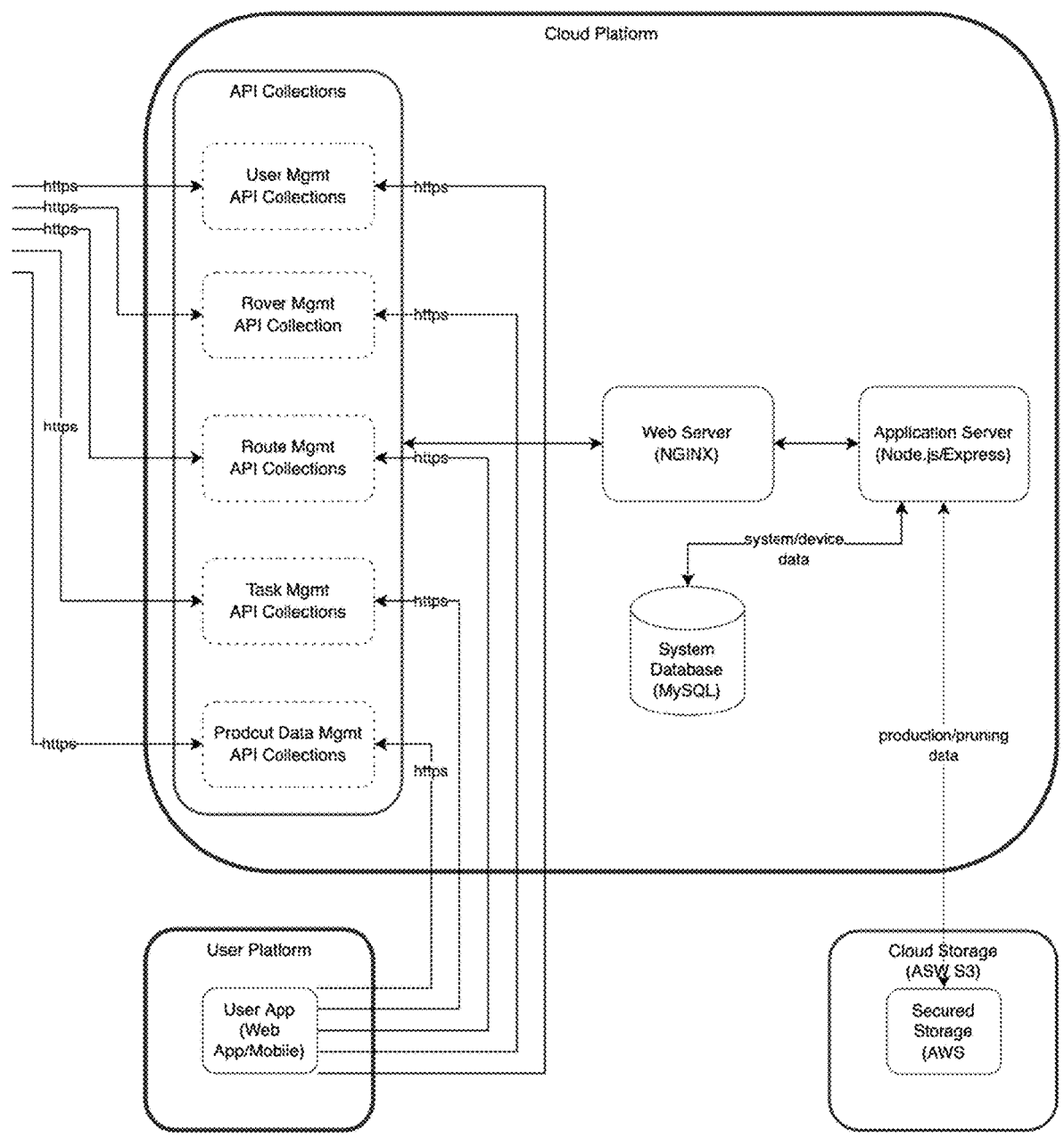

The imaging electronics 167 and the base electronics 194 of the cartesian arm system 100 can each be partially or completely implemented by edge computing to provide a vehicle platform, for example, by an NVIDIA® JETSON™ AGX computer. In a preferred embodiment of the present invention, the edge computing provides all of the computation and communication needs of the cartesian arm system. FIGS. 7A and 7B show an example of a block diagram of a cloud system that includes the vehicle platform and interactions with a cloud platform and a user platform. As shown in FIGS. 7A and 7B, the edge computing of the vehicle platform includes a cloud agent, which is a service-based component that facilitates communication between the vehicle platform and the cloud platform. For example, the cloud agent can receive command and instruction data from the cloud platform (e.g., a web application on the cloud platform), and then transfer the command and instruction data to corresponding components of the vehicle platform. As another example, the cloud agent can transmit operation data and production data to the cloud platform. Preferably, the cloud platform can include software components and data storage to maintain overall operation of the cloud system. The cloud platform preferably provides enterprise-level services with on-demand capacity, fault tolerance, and high availability (for example, AMAZON WEB SERVICES™). The cloud platform includes one or more application programming interfaces (APIs) to communicate with the vehicle platform and with the user platform. Preferably, the APIs are protected with a high level of security and a capacity of each of the APIs can be automatically adjusted to meet computational loads. The user platform provides a dashboard to control the cloud system and to receive data obtained by the vehicle platform and the cloud platform. The dashboard can be implemented by a web-based (e.g., internet browser) application, a mobile application, a desktop application, and the like.

As an example, the edge computing of the vehicle platform shown in FIG. 7A can obtain data from a HW (hardware) GPS (Global Positioning System) (for example, GNSS 192) and LiDAR data (for example, from LiDAR system 191). In addition, the vehicle platform can obtain data from a color/depth camera (for example, first camera 162) and data from an HSI camera (for example, second camera 163). The edge computing of the vehicle platform can include a temporary storage, for example, to store raw data obtained by the HSI camera. The edge computing of the vehicle platform can also include a persistent storage, for example, to store processed data. As a specific example, raw HSI data stored in the temporary storage can be processed by an artificial intelligence (AI) model, the processed HSI data can then be stored in the persistent storage, and the cloud agent can retrieve and transmit the processed HSI data from the persistent storage.

Figure 4A:
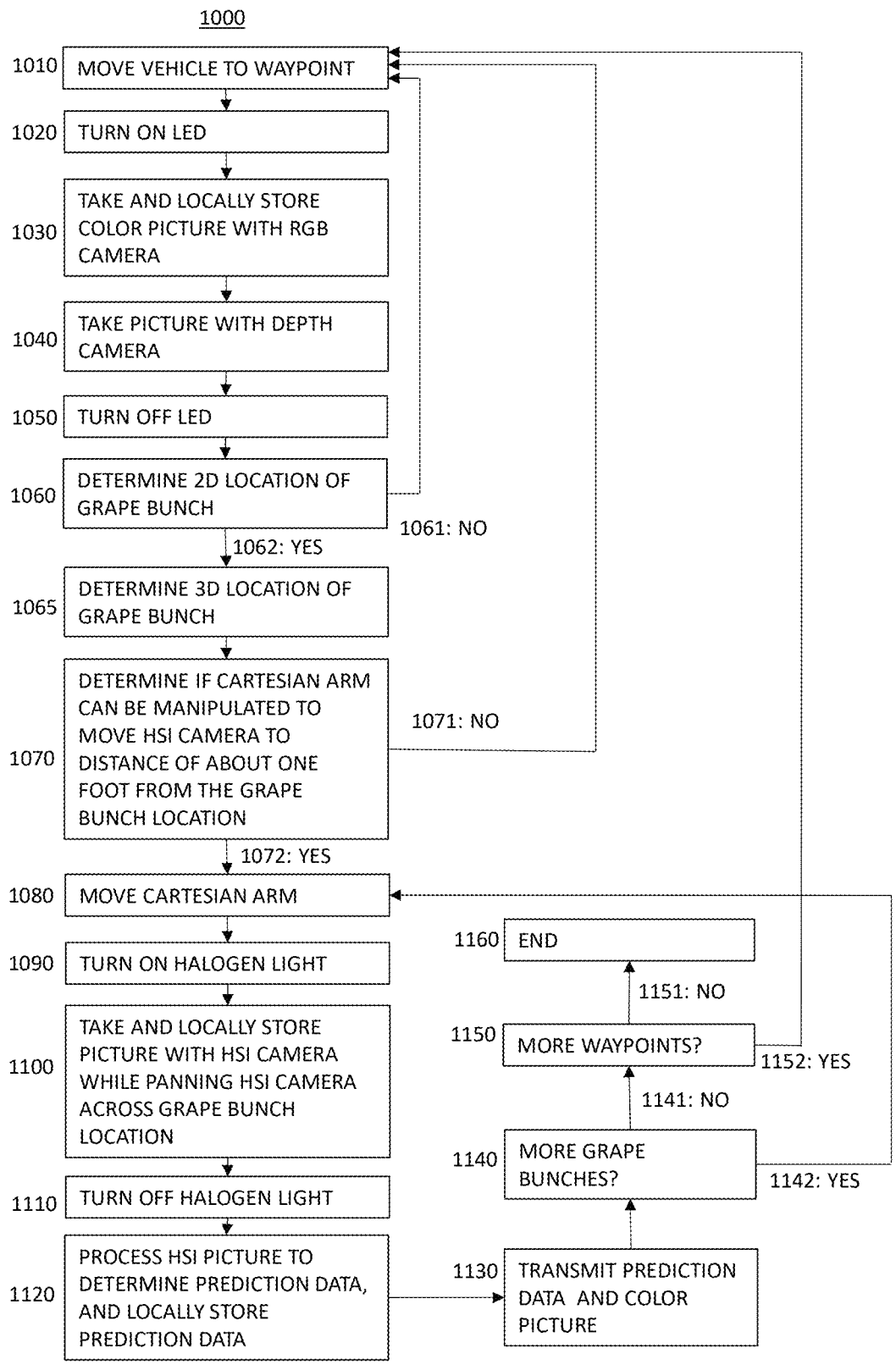
FIG. 4A-4F are flowcharts showing processes performed by a vehicle or the cartesian arm system according to preferred embodiments of the present invention.
Figure 4B:
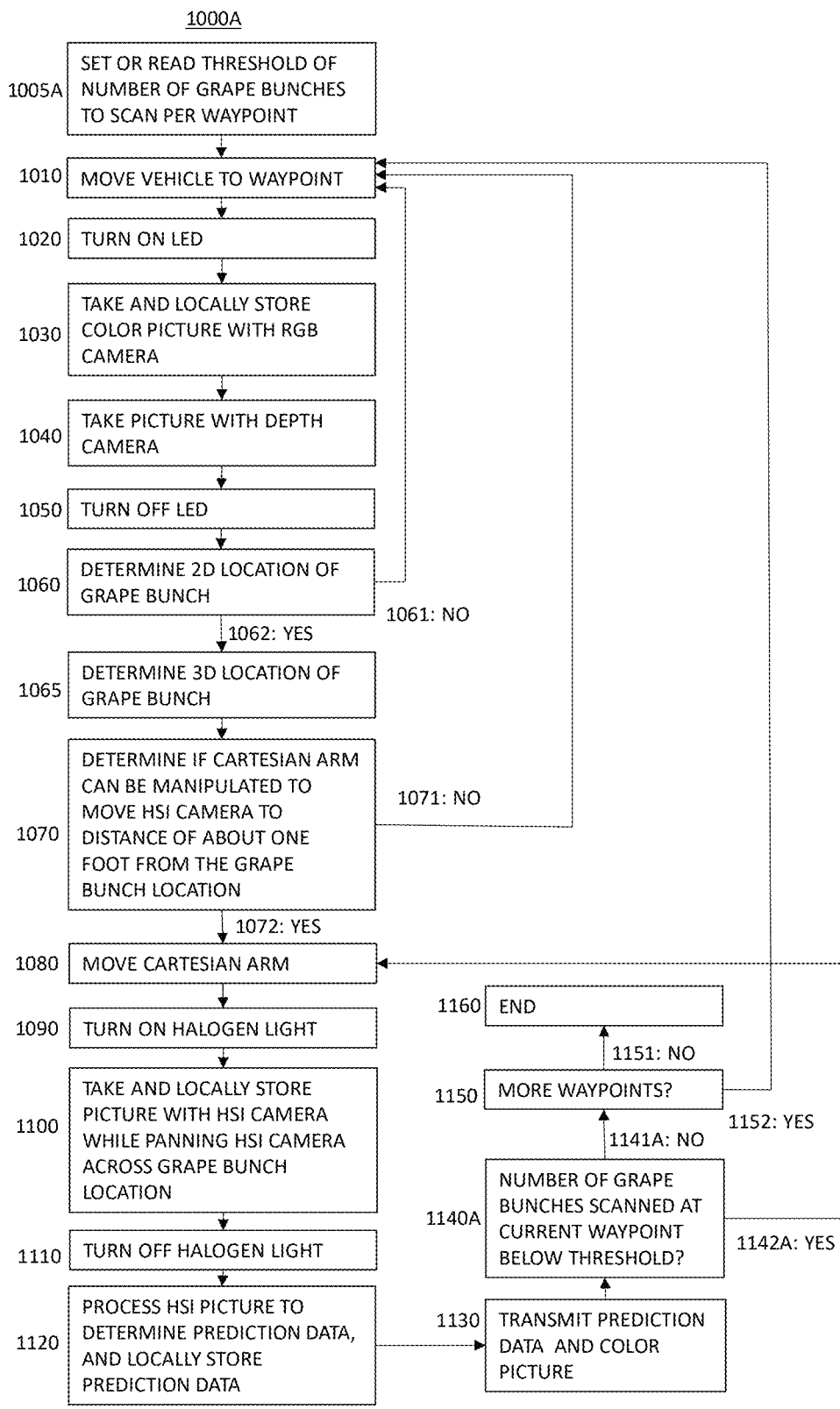
Figure 4C:
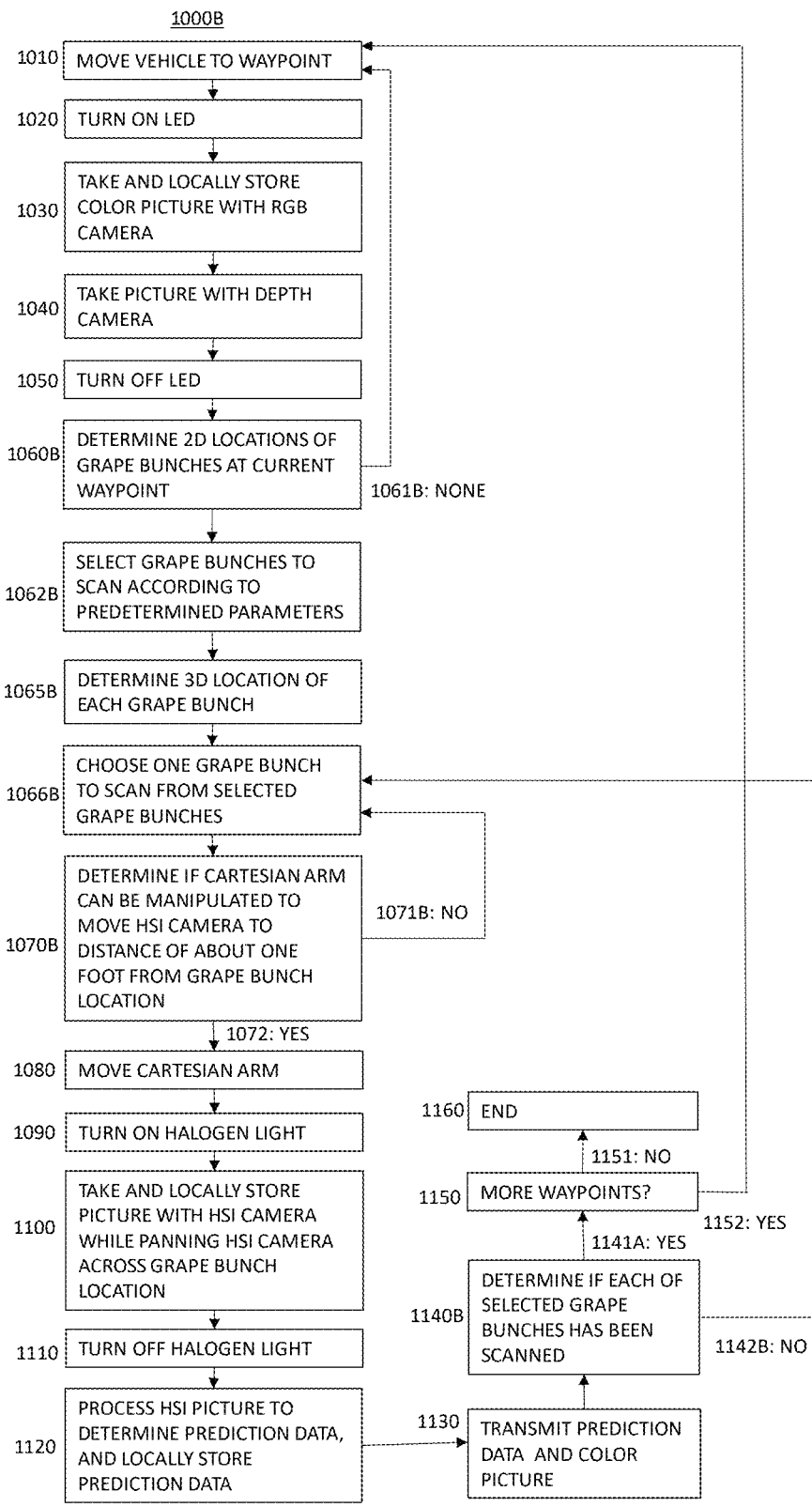
Figure 4D:
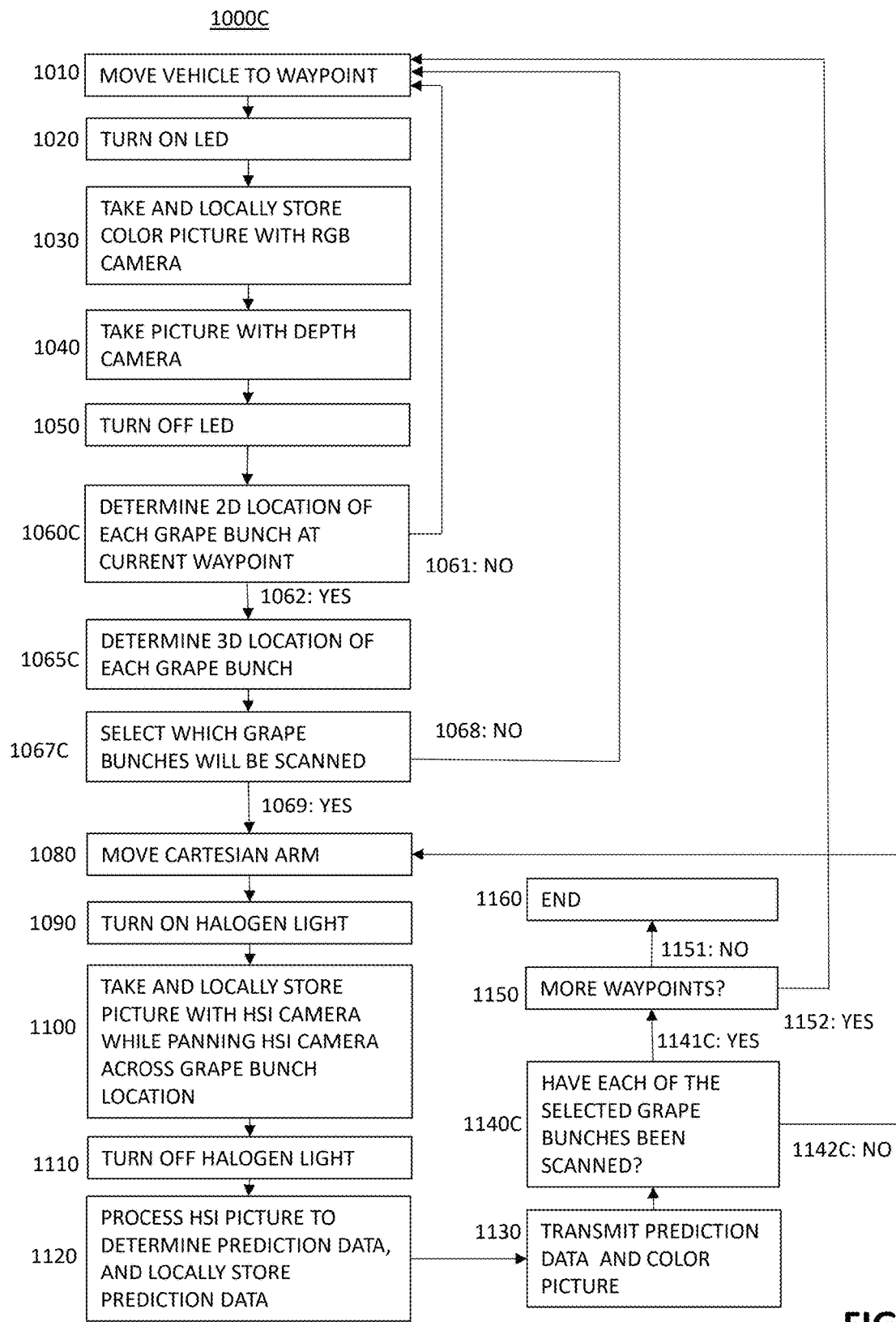

FIG. 4A is a flowchart showing a process 1000 performed according to a preferred embodiment of the present invention. FIGS. 4B, 4C, and 4D described further below, are flowcharts showing modified processes 1000A, 1000B, and 1000C according to additional preferred embodiments of the present invention. In a preferred embodiment, the processor and memory components of the imaging electronics 167 and/or processor and memory components of the base electronics 194 can be configured or programmed to perform the operations discussed in detail below with respect to FIGS. 4A-4F.

As shown in FIG. 4A, a vehicle (for example, the cartesian arm system 100) moves to a waypoint in operation 1010. The waypoint may be set or programmed in advance into an on-board memory of the vehicle, retrieved from a remote storage, determined according to a distance or time from a previous waypoint, or the like.

Upon reaching the waypoint, the vehicle is stopped, and the vehicle turns ON an LED in operation 1020. With the LED turned ON, the vehicle takes a color image (e.g., two-dimensional color image) with an RGB camera in operation 1030. The vehicle can store the color image taken by the RGB camera in a local storage of the vehicle.

After taking the color picture with the RGB camera, the vehicle takes a depth picture with a depth camera in operation 1040. The depth camera can be implemented by a LIDAR (light detection and ranging) camera, a stereo camera, a time-of-flight (TOF) sensor, or another depth sensor that can generate a depth estimation of an agricultural item including a grape bunch. The RGB camera and the depth camera can be implemented by a single camera (for example, the first camera 162). In a preferred embodiment of the present invention in which the RGB camera and the depth camera are implemented by a single camera, step 1030 of taking the color picture and step 1040 of taking the depth picture can be performed simultaneously.

After taking the depth picture with the depth camera, the vehicle turns OFF the LED in operation 1050. The vehicle performs processing in operation 1060 to determine a location of one or more grape bunches within the two-dimensional color image taken in operation 1030. In other words, the color image is used to determine a location of one or more grape bunches in a two-dimensional plane (e.g., Y-Z plane in FIG. 1).

Figure 13:
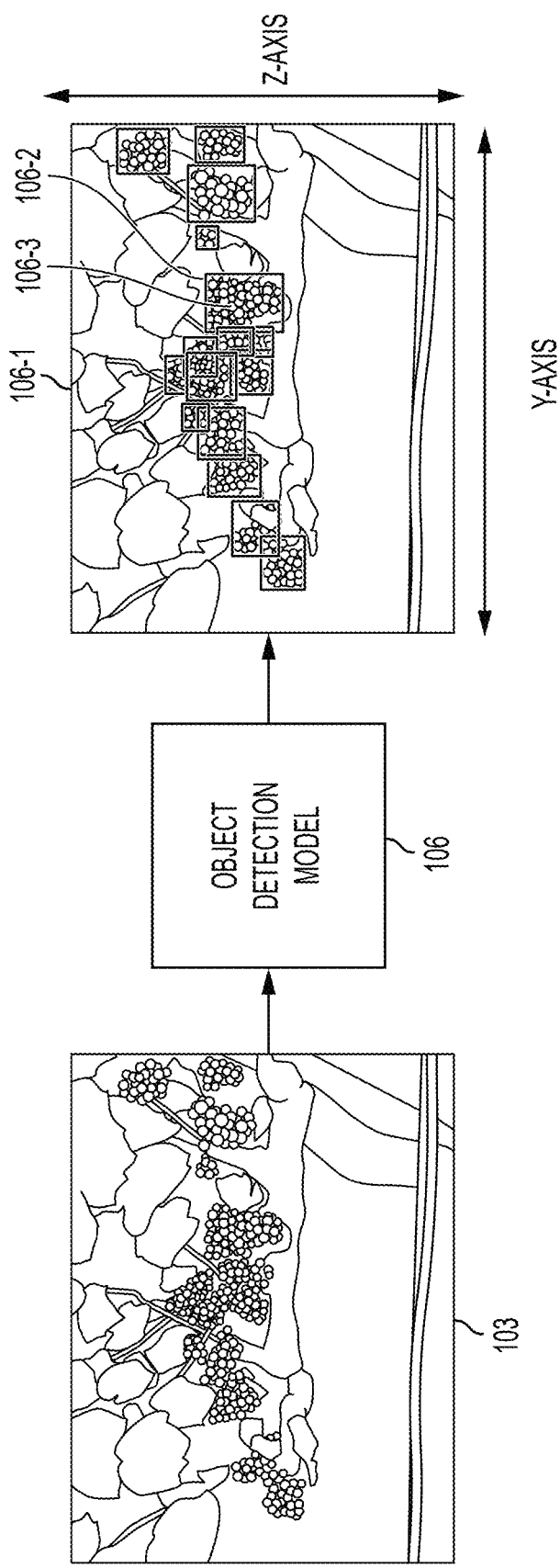
FIG. 13 shows an example of an object detection process according to a preferred embodiment of the present invention.

In a preferred embodiment of the present invention, operation 1060 includes detecting the one or more grape bunches using an object detection model 106, for example, an AI Deep Learning object detection model. FIG. 13 shows an example of operation 1060 in which an object detection model 106 is used to detect/identify the one or more grape bunches. The input to the object detection model 106 includes an image 103 of an agricultural item. For example, as shown in FIG. 13, an input to the object detection model 106 can include an image 103 captured in operation 1030. The object detection model 106 receives the input of the image 103 and outputs a feature image 106-1 that includes bounding boxes 106-2 that surround a particular agricultural feature (e.g., a grape bunch) shown in the image. For example, FIG. 13 shows that the object detection model 106 outputs a feature image 106-1 that includes bounding boxes 106-2 that surround each of the grape bunches included in the image.

In a preferred embodiment of the present invention, a location 106-3 of a particular grape bunch can be defined by a y-coordinate and a z-coordinate of a center point of the bounding box 106-2 that surrounds the grape bunch. For example, the location 106-3 can be defined by the y-coordinate and the z-coordinate of the pixel within the feature image 106-1 that includes the center point of the bounding box 106-2 that surrounds the grape bunch. Alternatively, the y-coordinate and the z-coordinate of another point within or on the bounding box 106-2 (e.g., the bottom left corner, the bottom right corner, the top left corner, or the top right corner of the bounding box 106-2) can be used to define the two-dimensional location of the grape bunch. Thus, a location 106-3 can be determined for each of the grape bunches detected during operation 1060.

In a preferred embodiment, the object detection model 106 can include a model backbone, a model neck, and a model head. The model backbone is primarily used to extract important features from a given input image. In a preferred embodiment, Cross Stage Partial (CSP) Networks can be used as the model backbone to extract informative features from the input image. The model neck is primarily used to generate feature pyramids, which assist the object detection model 106 to be well generalized on object scaling of the grape bunches. The performance of the object detection model 106 is improved by identifying the same object (e.g., a grape bunch) with different scales and sizes. The model head is primarily used to perform the final detection of the grape bunch. The model head applies anchor boxes on the grape bunches included in the image and generates final output vectors with class probabilities, object scores, and the bounding boxes 106-2 of the feature image 106-1.

In a preferred embodiment of the present invention, operation 1060 is performed using an object detection model 106 such as YoloV4, however, other models can be used. The trained object detection model can be converted to a TensorRT optimized engine for faster inference.

In a preferred embodiment, the object detection model 106 can be trained using a detection dataset tailored to an object detection task with respect to a grape bunch. For example, the detection dataset is tailored to a grape bunch. The detection dataset includes a plurality of images that are selected based on factors including whether the images were captured with proper operating conditions and whether the images include an appropriate level of variety. Once the plurality of images to be included in the detection dataset are selected, the images are cleansed and annotated. For example, the images of the detection dataset tailored to an object detection task with respect to a grape bunch can be manually annotated using a computer implemented labeling tool.

Figure 14:
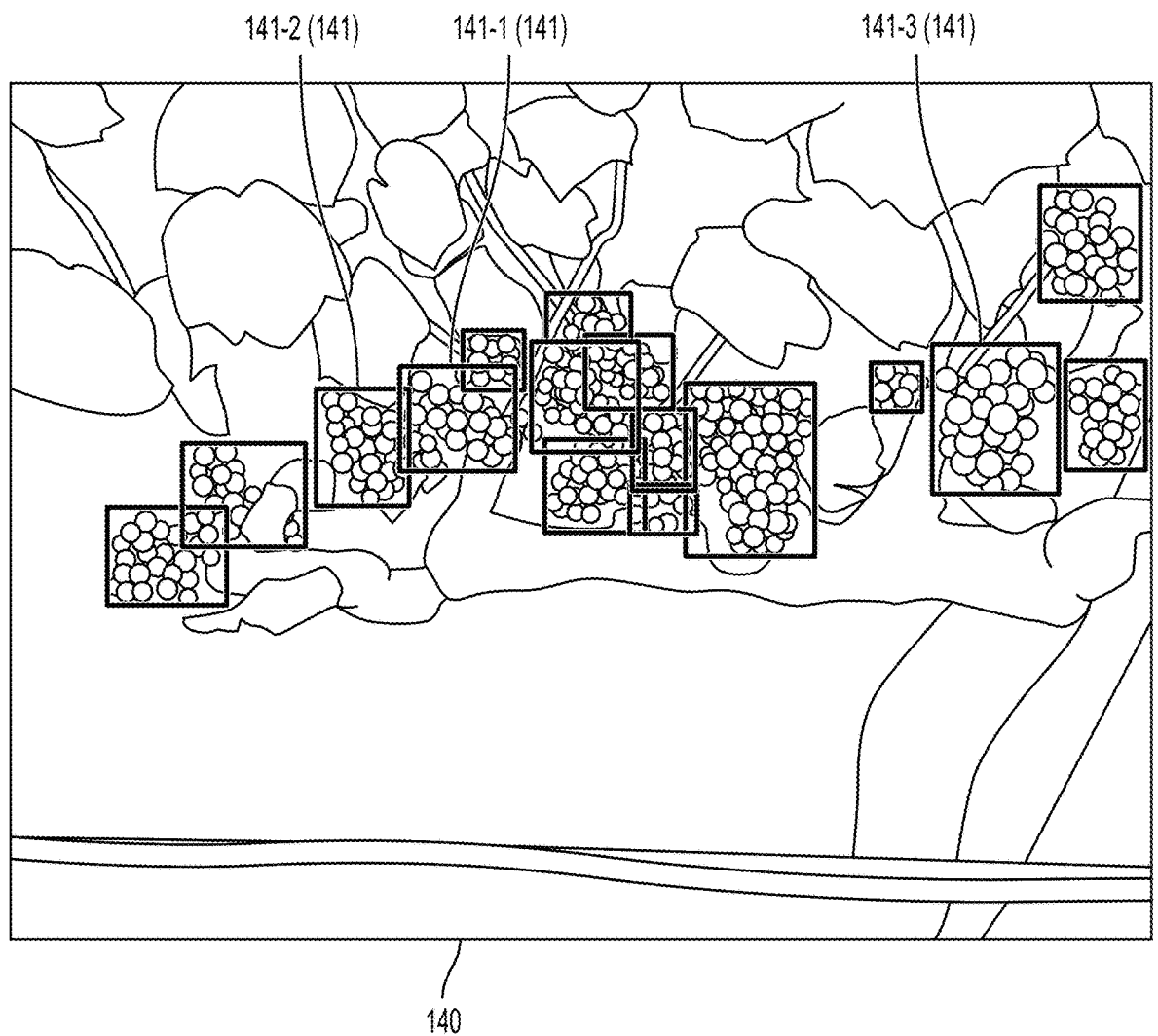
FIG. 14 shows an example of an image annotated using a computer implemented labeling tool according to a preferred embodiment of the present invention.

FIG. 14 shows an example of an image 140 included in the detection dataset which has been annotated using a computer implemented labeling tool. The computer implemented labeling tool includes a user interface that allows polygon masks to be formed around a particular agricultural feature of an agricultural item shown in the image 140. For example, when the agricultural feature is a grape bunch, the user interface of the labeling tool allows a polygon mask 141 to be formed around each grape bunch. In a preferred embodiment, polygon masks 141 of different sizes can be formed around the grape bunches in the image. For example, the size of the polygon mask can be determined based on the size of the particular grape bunch around which the polygon mask 141 is formed. For instance, when a distance between a grape bunch and the camera used to capture the image is larger such that the size of the grape bunch within the image 140 is smaller, then the size of the polygon mask 141 formed around the grape bunch is made smaller.

In a preferred embodiment of the present invention, the computer implemented labeling tool can use different types of polygon masks to classify different types of grape bunches. For example, as shown in FIG. 14, a first type of polygon mask 141-1 formed around a particular grape bunch can be used to classify the particular grape bunch surrounded by the polygon mask as a bunch overlapped grape bunch (a grape bunch that is overlapped by another grape bunch within the image 140), a second type of polygon mask 141-2 formed around a particular grape bunch can be used to classify the particular grape bunch surrounded by the polygon mask as a leaf overlapped grape bunch (a grape bunch that is overlapped by a leaf within the image), and a third type of polygon mask 141-3 formed around a particular grape bunch can be used to classify the particular grape bunch surrounded by the polygon mask as an unobstructed grape bunch (a grape bunch that is not overlapped by another grape bunch or a leaf within the image). In this way, because the image 140 included in the detection dataset has been annotated using the different types of polygon masks including the first type of polygon mask 141-1, the second type of polygon mask 141-2, and the third type of polygon mask 141-3, the object detection model 106 in operation 1060 can be used to detect/identify each of the one or more grape bunches included in the image 103 captured in operation 1030, and whether each of the grape bunches in the image 103 is a bunch overlapped grape bunch, a leaf overlapped grape bunch, or an unobstructed grape bunch.

Returning to FIG. 4A, if a grape bunch location is not determined in operation 1060 (1061: NO), the process 1000 returns to operation 1010 and the vehicle moves to a next waypoint. If a two-dimensional grape bunch location is determined (1062: YES), the vehicle then determines a three-dimensional location of the grape bunch in operation 1065 by adding depth information from the depth picture taken in operation 1040 to the two-dimensional color image taken in operation 1030. For example, if a two-dimensional grape bunch location is defined by the location 106-3 which is the y-coordinate and the z-coordinate of the pixel within the image 103 that includes the center point of the bounding box 106-2 that surrounds the grape bunch, a three-dimensional location of the grape bunch can be determined in operation 1065 by adding the depth information (depth information in the x-direction) of the pixel within the image 103 that includes the center point of the bounding box 106-2 that surrounds the grape bunch. For example, a coordinate (a pixel) of the two-dimensional grape bunch location can be identified, and then a corresponding coordinate can be identified in a depth estimation of the grape bunch. The depth value of the corresponding coordinate from the depth estimation of the grape bunch can be used as the depth value of the two-dimensional grape bunch location. In this way, the two-dimensional grape bunch location can be projected to a three-dimensional grape bunch location that includes X, Y, and Z coordinates. In another preferred embodiment of the present invention, the determined three-dimensional location of the grape bunch can be calculated based on an average depth of a plurality of grapes in the grape bunch.

In a preferred embodiment, the vehicle then determines in operation 1070 if a cartesian arm of the vehicle can be manipulated to move an HSI camera (for example, the second camera 163) to a predetermined distance (e.g., about one foot) from the determined three-dimensional location of the grape bunch. The predetermined distance can be based upon a focus length of the HSI camera (for example, about one foot), which is fixed in a preferred embodiment of the present invention. The cartesian arm can be manipulated by, for example, the base frame motor 115, the horizontal frame motor 145, and the vertical frame motor 155. If the cartesian arm of the vehicle cannot be manipulated to move the HSI camera to the predetermined distance from the determined location of the grape bunch (1071: NO), the process 1000 returns to operation 1010 and the vehicle moves to a next waypoint.

If the cartesian arm of the vehicle can be manipulated to move the HSI camera to the predetermined distance from the determined location of the grape bunch (1072: YES), the vehicle moves the cartesian arm in operation 1080 to the predetermined distance from the determined location of the grape bunch and turns ON a halogen light (for example, camera light source 164) in operation 1090. The halogen light emits a predetermined spectrum of light. After the halogen light has been turned ON, the vehicle takes an HSI picture with the HSI camera while manipulating the cartesian arm to pan the HSI camera across the determined location of the grape bunch in operation 1100. For example, the horizontal frame motor 145 is used to pan the HSI camera in the second direction (along the y-axis) across the grape bunch while the HSI image is being taken. In a preferred embodiment of the present invention, prior to taking the HSI image, the HSI camera may be heated to a predetermined temperature, or for a predetermined prior of time, which can improve stable data acquisition. The vehicle can store the HSI picture taken by the HSI camera in the local storage of the vehicle. Since the halogen light emits a predetermined spectrum of light to illuminate the grape bunch when the HSI camera obtains the HSI data, the HSI data is able to be processed with respect to this predetermined spectrum of light. After the HSI camera images the grape bunch, the vehicle turns OFF the halogen light in operation 1110.

In operation 1120, the vehicle processes an HSI picture taken by the HSI camera to determine prediction data of the grape bunch. The vehicle can store the HSI picture taken by the HSI camera and the prediction data in local storage(s) of the vehicle. For example, the HSI picture taken by the HSI camera can be initially stored in a temporary storage (e.g., a volatile memory), and data obtained by processing the HSI picture can subsequently be stored in a persistent storage (e.g., a non-volatile memory). The processing performed in operation 1120 is described in further detail below with respect to FIGS. 5 and 6.

In operation 1130, the vehicle transmits the prediction data and the color picture taken by the RGB camera, for example, to a remote storage. In addition, the color picture is provided with the prediction data so that a user is able to visually verify the location and suitability of grape bunches identified by the prediction data. However, since HSI pictures and the corresponding prediction data may have relatively large file sizes, only a portion of the prediction data or only selected HSI pictures may be transmitted, for example, to the remote storage. In addition, the vehicle may transmit only a portion of the color picture taken by the RGB camera, for example, to the remote storage. Similarly, the vehicle may transmit only selected color pictures taken by the RGB camera, for example, to the remote storage. According to another preferred embodiment of the present invention, the vehicle can transmit some or all color pictures taken by the RGB camera separately from transmitting the prediction data. That is, the vehicle may transmit some or all color pictures taken by the RGB camera at any point between operations 1040 and 1130. In addition to the above features, the prediction data can be applied to some or all of the color pictures so that a bounding box or the like is included with the color picture(s) to indicate a predicted location of grape bunch(es).

In operation 1140, the vehicle determines if additional grape bunches are to be imaged by the HSI camera at the current waypoint. If no additional grape bunches are to be imaged at the current waypoint (1141: NO), the process 1000 proceeds to operation 1150. However, if additional grape bunches are to be imaged by the HSI camera at the current waypoint (1142: YES), the process 1000 returns to operation 1080. As an example, the process 1000 may perform a sampling of only a portion of grape bunches in a vine or vineyard (e.g., three grape bunches per grape vine).

In a preferred embodiment of the present invention, the processor and memory components of the base electronics 194 can keep the vehicle stationary from when an image is acquired in operation 1030 until after the quality measuring device (e.g., the HSI camera) has measured the quality of the agricultural item in operation 1100.

In operation 1150, the vehicle determines if additional waypoints are to be traveled to by the vehicle. If no further waypoints are stored by the vehicle, able to be retrieved by the vehicle, or the like (1151: NO), the process 1000 ends at operation 1160. However, if further waypoints are stored by the vehicle, able to be retrieved by the vehicle, or the like (1152: YES), the process 1000 returns to operation 1010 and the vehicle moves to a next waypoint. As examples, the AI model can be used to determine a next waypoint, or waypoints can be pre-programmed according to GPS data.

FIG. 4B shows a modified process 1000A in which only a predetermined portion of grape bunches is sampled. Detailed description of operations shown in FIG. 4B that are the same as those shown in FIG. 4A are omitted for conciseness.

As shown in FIG. 4B, the modified process 1000A includes an operation 1005A of setting or reading a predetermined threshold of the number of grape bunches to be scanned per waypoint. For example, the predetermined threshold value can be set in advance by a user, and the vehicle can read the predetermined threshold value when executing the modified process 1000A. Subsequently, in operation 1140A, the vehicle determines if the number of grape bunches scanned at the current waypoint has reached the predetermined threshold. If the number of grape bunches scanned at the current waypoint is below the predetermined threshold (1142A: YES), the process 1000A returns to operation 1080. However, if the number of grape bunches scanned at the current waypoint has reached (is not below) the predetermined threshold (1141A: NO), the process 1000A proceeds to operation 1050.

FIG. 4C shows another modified process 1000B in which grape bunches can be selected for scanning according to the color picture with the RGB camera. Detailed description of operations shown in FIG. 4C that are the same as those shown in FIG. 4A will be omitted for conciseness.

As shown in FIG. 4C, the modified process 1000B includes an operation 1060B of determining two-dimensional locations of grape bunches at a current waypoint. However, if no grape bunch location is determined (1061: NO), the process 1000B returns to operation 1010 and the vehicle moves to a next waypoint. After determining the two-dimensional locations of grape bunches at the current waypoint in operation 1060B, the modified process 1000B then proceeds to operation 1062B to select grape bunches to be scanned from among the grape bunches corresponding to the determined two-dimensional locations. The grape bunches to be scanned can be selected according to various predetermined parameters, including, but not limited to, grape bunches that are least obstructed by obstacles (e.g., sticks, leaves, and the like), grape bunches that have a largest surface area facing the HSI camera, and/or grape bunches according to their color in the color picture (e.g., grape bunches that appear most ripe in the color picture).

Once grape bunches to be scanned have been selected in operation 1062B, a three-dimensional location of each grape bunch is determined in operation 1065B, similar to operation 1065 described above with respect to FIG. 4A. Subsequently, in operation 1066B, one grape bunch from the selected grape bunches is chosen for scanning by the HSI camera. In operation 1070B, the vehicle determines if the cartesian arm of the vehicle can be manipulated to move the HSI camera to a predetermined distance (e.g., about one foot) from the determined three-dimensional location of the chosen grape bunch. If the cartesian arm of the vehicle cannot be manipulated to move the HSI camera to the predetermined distance from the determined location of the grape bunch (1071B: NO), the process 1000B returns to 1066B and another grape bunch from the selected grape bunches is chosen for scanning by the HSI camera. If the cartesian arm of the vehicle cannot be manipulated to move the HSI camera to the predetermined distance from the determined location of any of the selected grape bunches, the modified process 1000B may return to operation 1010.

The modified process 1000B scans and transmits data regarding each of the determined grape bunch in operations 1080 to 1130, similar to the operations described above with respect to FIG. 4A. However, in operation 1140B, the modified process 1000B determines if each of the selected grape bunches has been scanned by the HSI camera. If each of the selected grape bunches has not been scanned (1142B: NO), the modified process 1140B returns to operation 1066B and another grape bunch from the selected grape bunches is chosen for scanning by the HSI camera. However, if each of the selected grape bunches has been scanned by the HSI camera (1141A: YES), the modified process 1000B proceeds to operation 1150, which has been described above with respect to FIG. 4A.

FIG. 4D shows a modified process 1000C in which grape bunches to have their quality measured using a quality measuring device (for example, the second camera 163 such as an HSI camera) can be selected according to an additional selection process. Detailed description of operations shown in FIG. 4D that are the same as those shown in FIG. 4A will be omitted for conciseness.

As shown in FIG. 4D, the modified process 1000C includes an operation 1060C of determining two-dimensional locations of each of the grape bunches at a current waypoint, similarly to operation 1060 discussed above with respect to FIG. 4A. However, if no grape bunch location is determined (1061: NO), the process 1000C returns to operation 1010 and the vehicle moves to a next waypoint. After determining the two-dimensional locations of the grape bunches at the current waypoint in operation 1060C, the modified process 1000C then proceeds to operation 1065C in which a three-dimensional location of each grape bunch is determined, similarly to operation 1065 described above with respect to FIG. 4A. Subsequently, the modified process 1000C proceeds to operation 1067C to select grape bunches to be scanned from among the grape bunches. If in operation 1067C it is determined that none of the grape bunches are suitable to be scanned (1068: NO), the process 1000C returns to operation 1010 and the vehicle moves to a next waypoint.

Figure 4E:
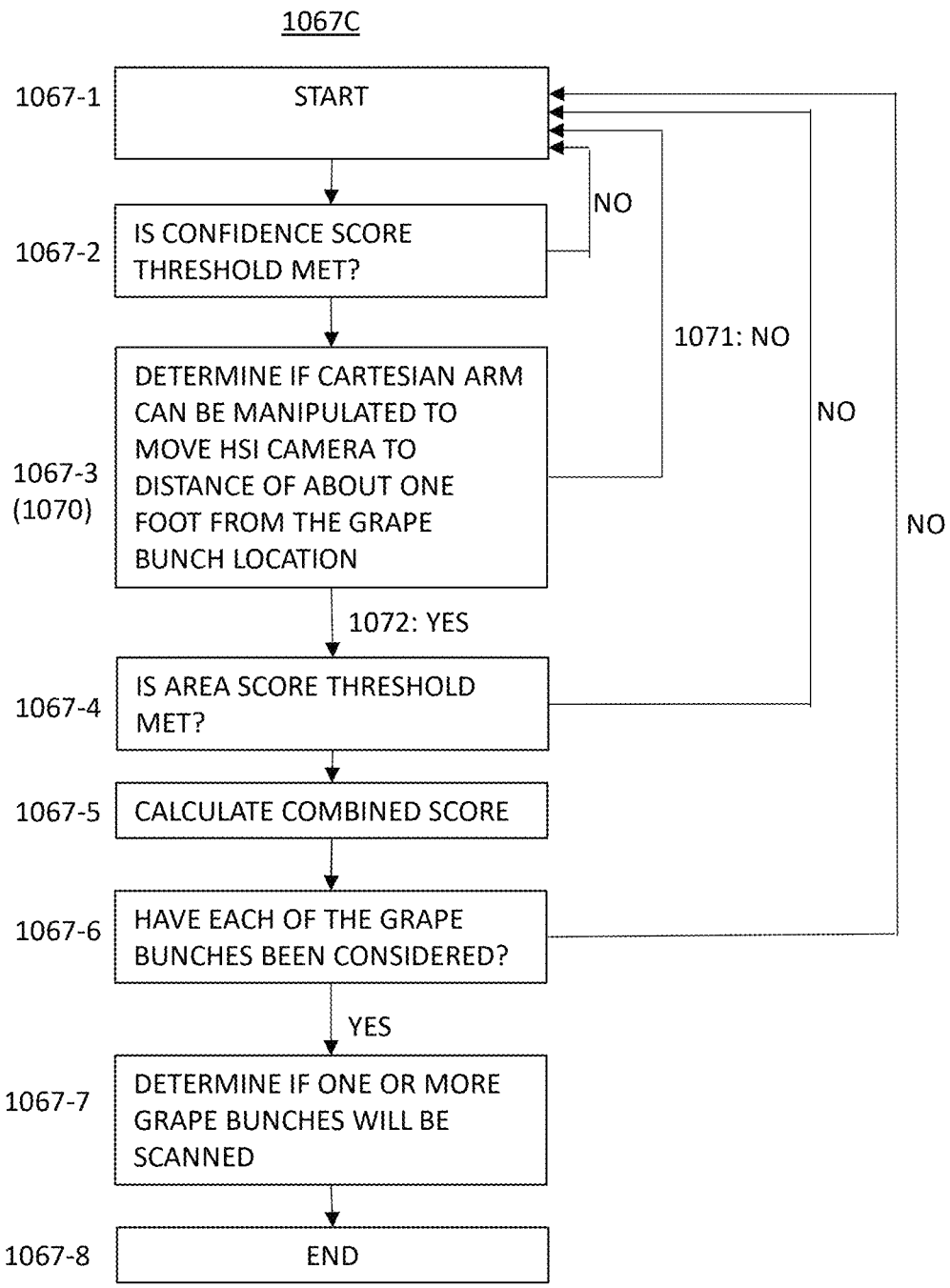

FIG. 4E is a flowchart showing the details of operations 1067-1 through 1067-8 included in operation 1067C. The operation 1067C is performed for each of the grape bunches for which a three-dimensional location of each grape bunch was determined in operation 1065C. In this way, as discussed in more detail below, when an image acquired by a camera (e.g., the first camera 162) in operation 1030 includes a plurality of grape bunches, the operation 1067C determines whether or not it is suitable to measure a quality of each of the plurality of grape bunches.

As shown in FIG. 4E, operation 1067C is started at operation 1067-1 in which one of the grape bunches for which a three-dimensional location of each grape bunch was determined in operation 1065C is selected. In operation 1067-2, it is determined whether or not the grape bunch selected in operation 1067-1 has a confidence score that meets a predetermined confidence score threshold. In a preferred embodiment, the confidence score of a grape bunch is a score based on a level of confidence that the grape bunch identified as a grape bunch in operation 1060C is in fact a grape bunch. In other words, the confidence score is a score based on a level of confidence that the agricultural item identified as a grape bunch in operation 1060C based on the image acquired in operation 1030 matches a predetermined certain type of agricultural item (a grape bunch). For example, the confidence score of a grape bunch can be measured on a scale from 0-1.0, wherein a value of 0 indicates that there is no level of confidence (0% level of confidence) that the grape bunch (object) identified as a grape bunch in operation 1060C is in fact a grape bunch, and a value of 1 indicates that there is a complete/certain level of confidence (100% level of confidence) that the grape bunch (object) identified as a grape bunch in operation 1060C is in fact a grape bunch. The confidence score of a grape bunch is an example of machine-learned-related data of the grape bunch, for example, because the confidence score is generated by the object detection model 106 (e.g., the AI Deep Learning object detection model) used to detect the one or more grape bunches in operation 1060, and as discussed above, the object detection model 106 is a machine trained model trained using a detection dataset.

In a preferred embodiment, the predetermined confidence score threshold can be set to a value of 0.6, for example, however, the predetermined confidence score threshold can be set to a value other than 0.6. In operation 1067-2, if it is determined that the grape bunch has a confidence score that meets the predetermined confidence score threshold, then the process 1067C proceeds to operation 1067-3. On the other hand, if in operation 1067-2 it is determined that grape bunch does not have a confidence score that meets the predetermined confidence score threshold, then the process 1067C returns to operation 1067-1 and a next one of the grape bunches for which a three-dimensional location of each grape bunch was determined in operation 1065C is selected. In this way, based on the confidence score generated using the image acquired by a camera (e.g., the first camera 162) in operation 1030, it can be determined whether or not it is suitable to measure a quality of the grape bunch using a quality measuring device (for example, the second camera 163 such as an HSI camera).

In operation 1067-3, it is determined whether or not the cartesian arm of the vehicle can be manipulated to move an HSI camera (for example, second camera 163) to a predetermined distance (e.g., about one foot) from the determined three-dimensional location of the grape bunch selected in operation 1067-1. As discussed above, in a preferred embodiment of the present invention, the determined three-dimensional location of the grape bunch can be calculated based on the two-dimensional grape bunch location defined by the location 106-3 and adding the depth information (depth information in the x-direction). The predetermined distance can be based upon a focus length of the HSI camera (for example, about one foot), which is fixed in a preferred embodiment of the present invention, and the cartesian arm can be manipulated by, for example, the base frame motor 115, the horizontal frame motor 145, and the vertical frame motor 155.

In a preferred embodiment of the present invention, the operation 1067-3 can include determining whether or not the three-dimensional location of the grape bunch selected in operation 1067-1 includes a depth value (e.g., a distance between the HSI camera and the determined three-dimensional location of the grape bunch in the x-direction shown in FIG. 1) that meets a predetermined acceptable depth range. The depth value of the grape bunch is a non-limiting example of detection data of the grape bunch generated using the image acquired by a camera (e.g., the first camera 162) in operation 1040.

In a preferred embodiment of the present invention, the depth value of the grape bunch (e.g., a distance between the HSI camera and the determined three-dimensional location of the grape bunch in the x-direction shown in FIG. 1) can be determined based on the three-dimensional location of the grape bunch and the three-dimensional location of the HSI camera. In a preferred embodiment, the first camera 162 (e.g., the depth camera) and the second camera 163 (e.g., the HSI camera) have a fixed relationship to one another such that a depth distance between the first camera 162 (e.g., the depth camera) and the three-dimensional location of the grape bunch in the x-direction shown in FIG. 1 can be determined, and then the fixed relationship between the first camera 162 (e.g., the depth camera) and the second camera 163 (e.g., the HSI camera) can be used to determine a distance between the HSI camera and the determined three-dimensional location of the grape bunch in the x-direction shown in FIG. 1.

In a preferred embodiment, the operation 1067-3 includes determining whether or not the three-dimensional location of the grape bunch selected in operation 1067-1 includes a depth value that allows the cartesian arm of the vehicle to be manipulated to move an HSI camera (for example, second camera 163) to an optimal depth distance (e.g., about one foot) from the determined three-dimensional location of the grape bunch selected in operation 1067-1. For example, if the optimal depth distance from the HSI camera to the determined three-dimensional location of the grape bunch is set at 1.0 feet, then the predetermined acceptable depth range can be set to 0.75 feet to 1.25 feet. If the three-dimensional location of the grape bunch includes a depth value (e.g., a distance between the HSI camera and the determined three-dimensional location of the grape bunch in the x-direction shown in FIG. 1) of 0.75 feet to 1.25 feet, then the three-dimensional location of the grape bunch includes a depth value that meets the predetermined acceptable depth range. On the other hand, if the three-dimensional location of the grape bunch includes a depth value less than 0.75 feet or greater than 1.25 feet, then the three-dimensional location of the grape bunch includes a depth value that does not meets the predetermined acceptable depth range. In this way, based on the depth value generated using the image acquired by a camera (e.g., the first camera 162) in operation 1040, it can be determined whether or not it is suitable to measure a quality of the grape bunch using a quality measuring device (for example, the second camera 163 such as an HSI camera).

In a preferred embodiment of the present invention, if the three-dimensional location of the grape bunch selected in operation 1067-1 includes a depth value that meets the predetermined acceptable depth range, the operation 1067-3 can also include determining a depth score for the grape bunch selected in operation 1067-1. In a preferred embodiment, the depth score for the grape bunch can be based on the depth value of the grape bunch (e.g., a distance between the HSI camera and the determined three-dimensional location of the grape bunch in the x-direction shown in FIG. 1).

For example, the depth score can be based on the depth value of the grape bunch such that the depth score is best when the depth value is a minimum value, and the depth score is worst when the depth value is at a maximum value. For instance, in the example discussed above in which the predetermined acceptable depth range is set to 0.75 feet to 1.25 feet, the depth score is best when the depth value is 0.75 feet, and the depth score is worst when the depth value is 1.25 ft.

In another example, the depth score can be based on a degree to which the depth value matches the optimal depth distance from the HSI camera to the determined three-dimensional location of the grape bunch. For instance, in the example discussed above in which the optimal depth distance from the HSI camera to the determined three-dimensional location of the grape bunch is 1.0 feet, the depth score is best when the depth value is 1.0 feet, and the depth score is worst when the depth value is 0.75 ft or 1.25 ft (depth values farthest from the optimal depth distance of 1.0 feet).

In operation 1067-3, if it is determined that the cartesian arm of the vehicle can be manipulated to move the HSI camera to the predetermined distance from the determined location of the grape bunch (1072: YES), then the process 1067C proceeds to operation 1067-4. On the other hand, if in operation 1067-3 it is determined that the cartesian arm of the vehicle cannot be manipulated to move the HSI camera to the predetermined distance from the determined location of the grape bunch (1071: NO), then the process 1067C returns to operation 1067-1 and a next one of the grape bunches for which a three-dimensional location of each grape bunch was determined in operation 1065C is selected.

In operation 1067-4, it is determined whether or not the grape bunch selected in operation 1067-1 has an area score that meets an area score threshold. In a preferred embodiment, the area score of a grape bunch is a score based on an area value (e.g., a normalized area value) of the grape bunch within the two-dimensional image taken in operation 1030 such that the area score is based on a size of the grape bunch. For example, the area score of a grape bunch can be determined based on a normalized area value of the bounding box 106-2 that surrounds the grape bunch in the feature image 106-1. The area score of the grape bunch is a non-limiting example of detection data of the grape bunch generated using the image acquired by a camera (e.g., the first camera 162) in operation 1030.

In operation 1067-4, if it is determined that the grape bunch has an area score that meets the predetermined area score threshold, then the process 1067C proceeds to operation 1067-5. On the other hand, if in operation 1067-4 it is determined that grape bunch does not have an area score that meets the predetermined area score threshold, then the process 1067C returns to operation 1067-1 and a next one of the grape bunches for which a three-dimensional location of each grape bunch was determined in operation 1065C is selected. In this way, based on the area score generated using the image acquired by a camera (e.g., the first camera 162) in operation 1030, it can be determined whether or not it is suitable to measure a quality of the grape bunch using a quality measuring device (for example, the second camera 163 such as an HSI camera).

In operation 1067-5, a combined score is calculated for the grape bunch selected in operation 1067-1. In a preferred embodiment, the combined score can be based on one or more of the confidence score (e.g., a first score) determined in operation 1067-2, the depth score (e.g., a second score) determined in operation 1067-3, and the area score (e.g., a third score) determined in operation 1067-4. In a preferred embodiment, the combined score can represent how suitable it is to measure the quality of a certain grape bunch using a quality measuring device (for example, the second camera 163 such as an HSI camera). For example, the combined score can be calculated by adding the confidence score, the depth score, and the area score as shown in the following equation (1).

$$\text{combined score} = \text{confidence score} + \text{depth score} + \text{area score} \tag{1}$$

However, this is a non-limiting example of how the combined score is calculated. For example, the combined score can be calculated by adding the confidence score and the depth score, or by adding the confidence score and the area score.

In a preferred embodiment of the present invention, one or more of the confidence score, the depth score, and the area score can be weighted when the combined score is calculated. For example, the combined score can be calculated by weighting the confidence score by a first weight variable w1, weighting the depth score by a second weight variable w2, and weighting the area score by a third weight variable w3, as shown in the following equation (2).

$$\text{combined score} = (w1 * \text{confidence score} + (-w2) * \text{depth score} + w3 * \text{area score}) / (w1 + w2 + w3) \tag{2}$$

In a preferred embodiment, the first weight variable w1 used to weight the confidence score can be greater than each of the second weight variable w2 used to weight the depth score and the third weight variable w3 used to weight the area score. In this way, among the confidence score, the depth score, and the area score, the most weight is given to the confidence score when calculating the combined score.

In a preferred embodiment, the first weight variable w1 used to weight the confidence score can be greater than each of the second weight variable w2 used to weight the depth score and the third weight variable w3 used to weight the area score, and the second weight variable w2 used to weight the depth score can be greater than the third weight variable w3 used to weight the area score. In this way, among the confidence score, the depth score, and the area score, the most weight is given to the confidence score and the least weight is given to the area score. For example, the first weight variable w1 used to weight the confidence score can be assigned a value of 0.4, the second weight variable w2 used to weight the depth score can be assigned a value of 0.25, and the third weight variable w3 used to weight the area score can be assigned a value of 0.1. However, these values are a non-limiting example, and the first weight variable w1, the second weight variable w2, and the third weight variable w3 can be assigned different values.

As discussed above, in a preferred embodiment, the depth score is best when the depth value is a minimum value, and the depth score is worst when the depth value is at a maximum value. In such a case, the second weight variable w2 used to weight the depth score can be assigned a negative value (e.g., −0.25). For instance, if the predetermined acceptable depth range is set to 0.75 feet to 1.25 feet, the depth score is best when the depth value is 0.75 ft (i.e., the depth score=0.75×−0.25=−0.1875), and the depth score is worst when the depth value is 1.25 ft (i.e., the depth score=1.25×−0.25=−0.3125). In this case, the depth score of −0.1875 when the depth value is 0.75 ft is better than the depth score of −0.3125 when the depth value is 1.25 ft because the depth score of −0.1875 when the depth value is 0.75 ft results in a higher combined score.

As discussed above, in another example, the depth score can be based on a degree to which the depth value matches the optimal depth distance from the HSI camera to the determined three-dimensional location of the grape bunch (a difference between the depth value and the optimal depth distance from the HSI camera to the determined three-dimensional location of the grape bunch). For instance, in the example discussed above in which the optimal depth distance from the HSI camera to the determined three-dimensional location of the grape bunch is 1 foot, the depth score is best when the depth value is 1 foot, and the depth score is worst when the depth value is 0.75 ft or 1.25 ft (depth values farthest from the optimal depth distance of 1 foot). In such a case, the second weight variable w2 used to weight the depth score can be assigned a negative value (e.g., −0.25). For instance, in this example in which the optimal depth distance from the HSI camera to the determined three-dimensional location of the grape bunch is 1.0 feet, the depth score is best when the depth value is 1.0 feet (i.e., the depth score=0 (the difference between the depth value and the optimal depth distance from the HSI camera to the determined three-dimensional location of the grape bunch)×−0.25=0), and the depth score is worst when the depth value is 0.75 ft (i.e., the depth score=0.25 (the difference between the depth value of 0.75 and the optimal depth distance of 1 ft)×−0.25=−0.0625) or the depth value is 1.25 ft (i.e., the depth score=0.25 (the difference between the depth value of 1.25 and the optimal depth distance of 1 ft)×−0.25=−0.0625). In this case, the depth score of 0 when the depth value is 1 ft is better than the depth score of −0.0625 when the depth value is 0.75 ft or 1.25 ft because the depth score of 0 when the depth value is 1 ft results in a higher combined score.

In a preferred embodiment, after the combined score is calculated for the grape bunch in operation 1067-5, the process 1067C proceeds to operation 1067-6. In operation 1067-6, it is determined whether or not each of the grape bunches for which a three-dimensional location of each grape bunch was determined in operation 1065C have been considered in operation 1067C. In operation 1067-6, if it is determined that each of the grape bunches for which a three-dimensional location was determined in operation 1065C have been considered in operation 1067C, then the process 1067C proceeds to operation 1067-7. On the other hand, if in operation 1067-6 it is determined that each of the grape bunches for which a three-dimensional location was determined in operation 1065C have not been considered in operation 1067C, then the process 1067C returns to operation 1067-1 and a next one of the grape bunches for which a three-dimensional location of each grape bunch was determined in operation 1065C is selected to be considered in operation 1067C.

In operation 1067-7, it is determined if one or more of the grape bunches for which a combined score was calculated in operation 1067-5 is selected to be scanned. In a preferred embodiment, operation 1067-7 can include ranking the grape bunches for which a combined score was calculated in operation 1067-5 from the grape bunch with the greatest combined score to the grape bunch with the lowest combined score. In other words, operation 1067-7 can include ranking the grape bunches for which a combined score was calculated in operation 1067-5 from the grape bunch most suitable to have its quality measured using a quality measuring device (for example, the second camera 163 such as an HSI camera) to the grape bunch least suitable to have its quality measured using the quality measuring device.

In a preferred embodiment, the grape bunch with the highest combined score among the grape bunches for which a combined score was calculated in operation 1067-5 can be selected as the single grape bunch to be scanned at the current waypoint. In another preferred embodiment, a predetermined number of the grape bunches with the highest combined scores among the grape bunches for which a combined score was calculated in operation 1067-5 can be selected as the grape bunches to be scanned at the current waypoint. For example, if there are six (6) grape bunches for which a combined score was calculated, the two (2) grape bunches with the highest combined scores among the six (6) grape bunches for which a combined score was calculated can be selected as the two (2) grape bunches to be scanned at the current waypoint. However, this is a non-limiting example, and the predetermined number of the grape bunches with the highest combined scores to be selected as the grape bunches to be scanned at the current waypoint can be set to a value other than two (2).

In another preferred embodiment, each grape bunch with a combined score greater than a combined score threshold among the grape bunches for which a combined score was calculated can be selected as a grape bunch to be scanned at the current waypoint. For example, if there are six (6) grape bunches for which a combined score was calculated, and three (3) of these grape bunches have combined score greater than the combined score threshold among, then each of these three (3) grape bunches can be selected as grape bunches to be scanned (to have its quality measured) at the current waypoint.

In a preferred embodiment, after it is determined if one or more of the grape bunches for which a combined score was calculated in operation 1067-5 is selected to be scanned in operation 1067-7, the process 1067C proceeds to operation 1067-8 at which the process 1067C ends and the process 1000C proceeds to 1080 in which the cartesian arm is moved to a predetermined distance from a determined location of a grape bunch selected to be scanned in process 1067C.

Figure 4F:
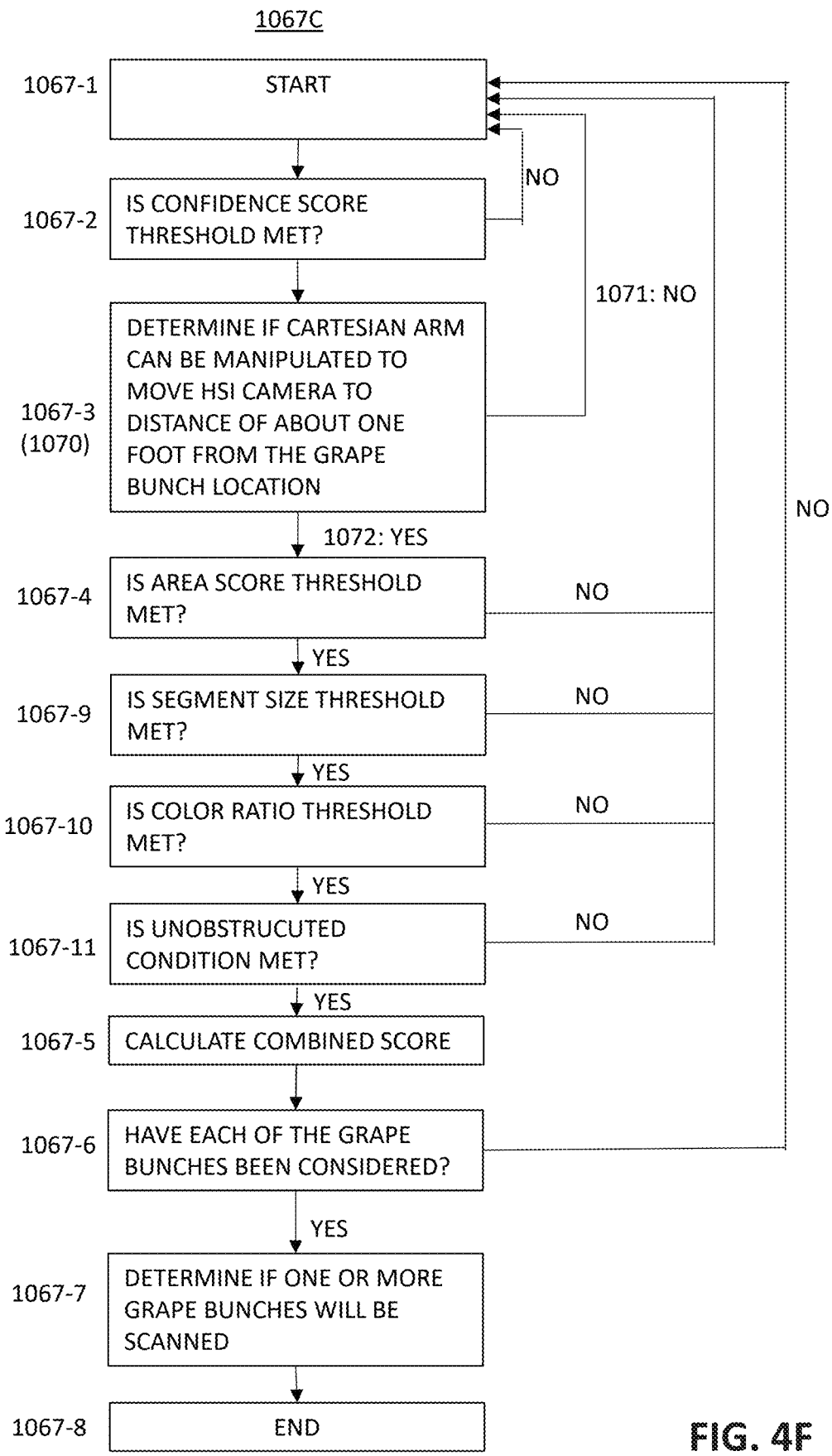

As shown in the flowchart of FIG. 4F, operation 1067C can include one or more additional operations including operation 1067-9, operation 1067-10, and operation 1067-11.

In operation 1067-9, it is determined whether or not the grape bunch selected in operation 1067-1 meets a segment size threshold. In a preferred embodiment, a segment size of a grape bunch can be determined based on an average size of a particular segment of the grape bunch. For example, the segment size of a grape bunch can be determined based on an average size of the grapes/berries within the grape bunch. In this case, the size of each of the individual grapes/berries within the grape bunch is detected, and then an average size of the grapes/berries within the grape bunch is determined. In a preferred embodiment, each individual grape/berry within the grape bunch can be detected using an AI-trained instance segmentation model such as Yolov4 or Mask-RCNN, and the size of each individual grape/berry can be determined based on the area of the individual grape/berry using the image acquired by a camera (e.g., the first camera 162) in operation 1030 and depth values of the individual grape/berry. Once the average size of the grapes/berries within the grape bunch is determined, the average size of the grapes/berries is compared to a segment size threshold (e.g., a predetermined and set size value) to determine whether or not the grape bunch meets the segment size threshold. For example, if the average size of the grapes/berries within the grape bunch is equal to or greater than the segment size threshold, then the grape bunch meets the segment size threshold. On the other hand, if the average size of the grapes/berries within the grape bunch is less than the segment size threshold, then the grape bunch does not meet the segment size threshold. While a segment size of a grape bunch is determined based on an average size of a particular segment of the grape bunch in the example discussed above, this is non-limiting, and the segment size of the grape bunch can instead be determined based on a median size of a particular segment of the grape bunch instead (e.g., a median size of the grapes/berries within a grape bunch), for example. The segment size of a grape bunch is a non-limiting example of detection data of the grape bunch generated using the image acquired by a camera (e.g., the first camera 162) in operations 1030 and 1040.

In operation 1067-9, if it is determined that the grape bunch meets the segment size threshold, then the process 1067C proceeds to operation 1067-10. On the other hand, if in operation 1067-9 it is determined that the grape bunch does not meet the segment size threshold, then the process 1067C returns to operation 1067-1 and a next one of the grape bunches for which a three-dimensional location of each grape bunch was determined in operation 1065C is selected. In this way, based on the segment size of the grape bunch, it can be determined whether or not it is suitable to measure a quality of the grape bunch using a quality measuring device (for example, the second camera 163 such as an HSI camera).

In operation 1067-10, it is determined whether or not the grape bunch selected in operation 1067-1 meets a color ratio threshold. In a preferred embodiment, a color ratio of a grape bunch can be determined based on a ratio of the colors of the grape bunch included in the image acquired by a camera (e.g., the first camera 162) in operation 1030. For example, if the first camera 162 is an RGB camera, then the color ratio of a grape bunch can be determined based on a ratio of the red pixels, the green pixels, and the blue pixels within the bounding box 106-2 that surrounds the grape bunch within the feature image 106-1 that is based on the image acquired by the camera (e.g., the first camera 162) in operation 1030. Once the color ratio of the grape bunch is determined, the color ratio is compared to an optimal color ratio (e.g., a predetermined and set optimal color ratio) to determine whether or not the grape bunch meets the color ratio threshold. For example, if the color ratio of the grape bunch is within a certain predetermined range of the optimal color ratio, then the grape bunch meets the color ratio threshold. On the other hand, if the color ratio of the grape bunch is not within the certain predetermined range of the optimal color ratio, then the grape bunch does not meet the color ratio threshold. In a preferred embodiment, the optimal color ratio can be set, for example, based on a certain variety of grape. For example, an optimal color ratio for a red grape can be set differently from an optimal color ratio for a green grape. The color ratio of a grape bunch is a non-limiting example of detection data of the grape bunch generated using the image acquired by a camera (e.g., the first camera 162) in operation 1030.

In operation 1067-10, if it is determined that the grape bunch meets the color ratio threshold, then the process 1067C proceeds to operation 1067-11. On the other hand, if in operation 1067-10 it is determined that the grape bunch does not meet the color ratio threshold, then the process 1067C returns to operation 1067-1 and a next one of the grape bunches for which a three-dimensional location of each grape bunch was determined in operation 1065C is selected. In this way, based on the color ratio of the grape bunch, it can be determined whether or not it is suitable to measure a quality of the grape bunch using a quality measuring device (for example, the second camera 163 such as an HSI camera).

Figure 15:
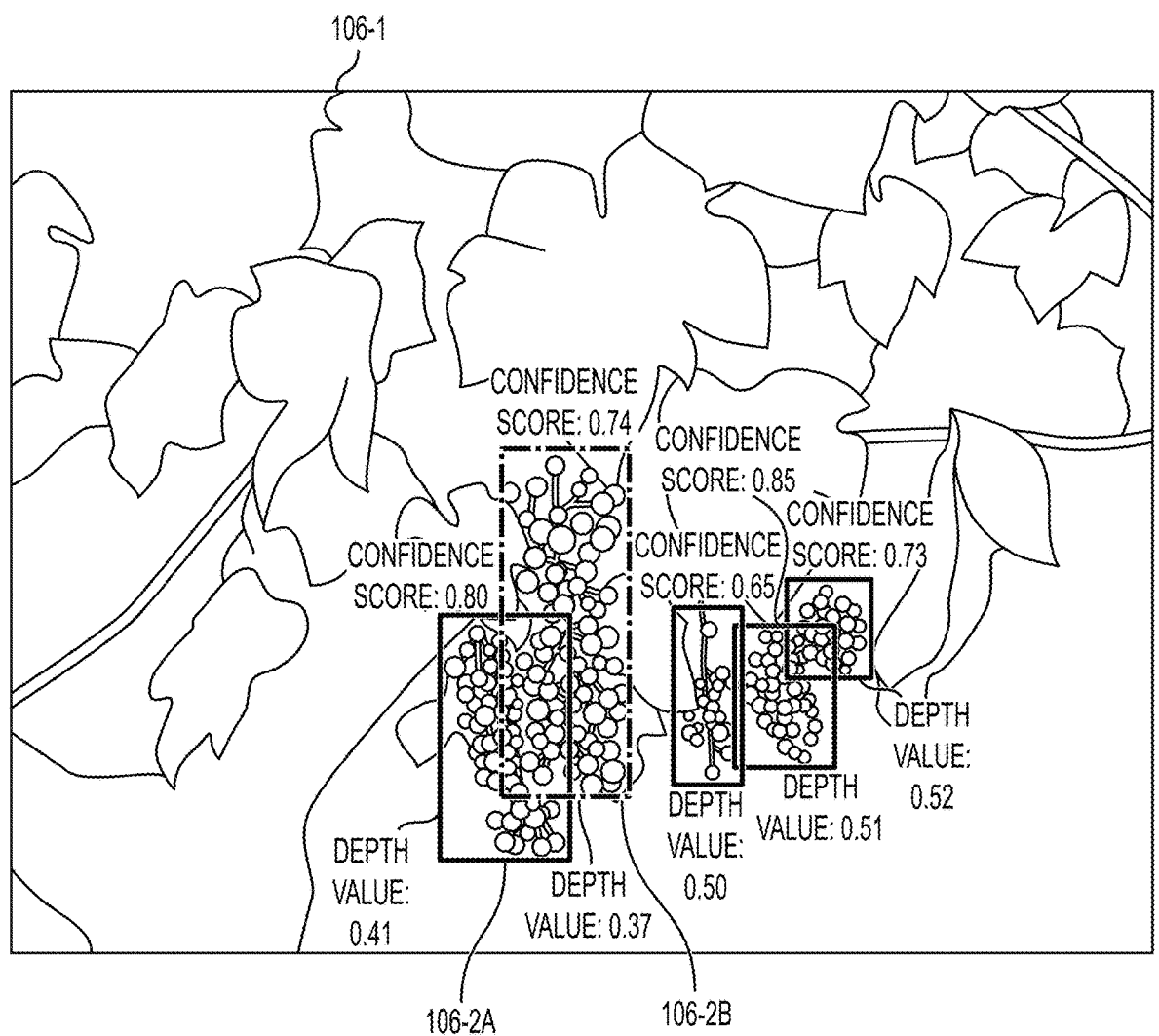
FIG. 15 shows an example of a feature image according to a preferred embodiment of the present invention.

In operation 1067-11, it is determined whether or not the grape bunch selected in operation 1067-1 meets an unobstructed condition. In a preferred embodiment, if the grape bunch is not obstructed by another grape bunch, then the unobstructed condition is met. On the other hand, if the grape bunch is obstructed by another grape bunch, then the unobstructed condition is not met. In a preferred embodiment, it can be determined whether or not a grape bunch is obstructed by another grape bunch based on the depth values of the respective grape bunches and the feature image 106-1 that includes bounding boxes 106-2 that surround each of the grape bunches included in the feature image 106-1. For example, as shown in FIG. 15, when the feature image 106-1 includes a first bounding box 106-2A that surrounds a first grape bunch and a second bounding box 106-2B that surrounds a second grape bunch, and the first bounding box 106-2A and the second bounding box 106-2B overlap within the feature image 106-1, then the bounding box among the first bounding box 106-2A and the second bounding box 106-2B that has a greater depth value (that surrounds the grape bunch with the greater depth value) is determined to surround a grape bunch that is obstructed. For instance, in the example shown in FIG. 15, the first bounding box 106-2A and the second bounding box 106-2B overlap within the feature image 106-1, and a depth value of the first bounding box 106-2A (0.41 feet) is greater than a depth value of the second bounding box 106-2B (0.37 feet), such that the first bounding box 106-2A is determined to surround a grape bunch that is obstructed (obstructed by the grape bunch surrounded by the second bounding box 106-2B which has a smaller depth value). In this case, the grape bunch surrounded by the first bounding box 106-2A would not meet the unobstructed condition, and the grape bunch surrounded by the second bounding box 106-2B would meet the unobstructed condition. The unobstructed condition of a grape bunch is a non-limiting example of detection data of the grape bunch generated using the image acquired by a camera (e.g., the first camera 162) in operation 1030.

In operation 1067-11, if it is determined that the grape bunch meets an unobstructed condition, then the process 1067C proceeds to operation 1067-5. On the other hand, if in operation 1067-11 it is determined that the grape bunch does not meet the unobstructed condition, then the process 1067C returns to operation 1067-1 and a next one of the grape bunches for which a three-dimensional location of each grape bunch was determined in operation 1065C is selected. In this way, based on whether or not a grape bunch is obstructed by another grape bunch, it can be determined whether or not it is suitable to measure a quality of the grape bunch using a quality measuring device (for example, the second camera 163 such as an HSI camera).

In a preferred embodiment, the modified process 1000C scans and transmits data regarding each of the determined grape bunch in operations 1080 to 1130, similar to the operations described above with respect to FIG. 4A. However, in operation 1140C, the modified process 1140C determines if each of the selected grape bunches (selected in operation 1067C) has been scanned by the HSI camera. If each of the selected grape bunches has not been scanned (1142C: NO), the modified process 1000C returns to operation 1080 and another grape bunch from the selected grape bunches is chosen for scanning by the HSI camera. However, if each of the selected grape bunches has been scanned by the HSI camera (1141C: YES), the modified process 1000C proceeds to operation 1150, which has been described above with respect to FIG. 4A.

In preferred embodiments discussed above, operation 1030 includes taking a color image (two-dimensional color image) with an RGB camera. However, operation 1030 is not limited in this way, and operation 1030 can alternatively include taking a grayscale image (image 103) with a camera (for example, the first camera 162). In a preferred embodiment, if operation 1030 includes taking a grayscale image (image 103) with a camera, the object detection model 106 is trained using a detection dataset that includes a plurality of grayscale images which has been annotated using the computer implemented labeling tool.

Figure 5:
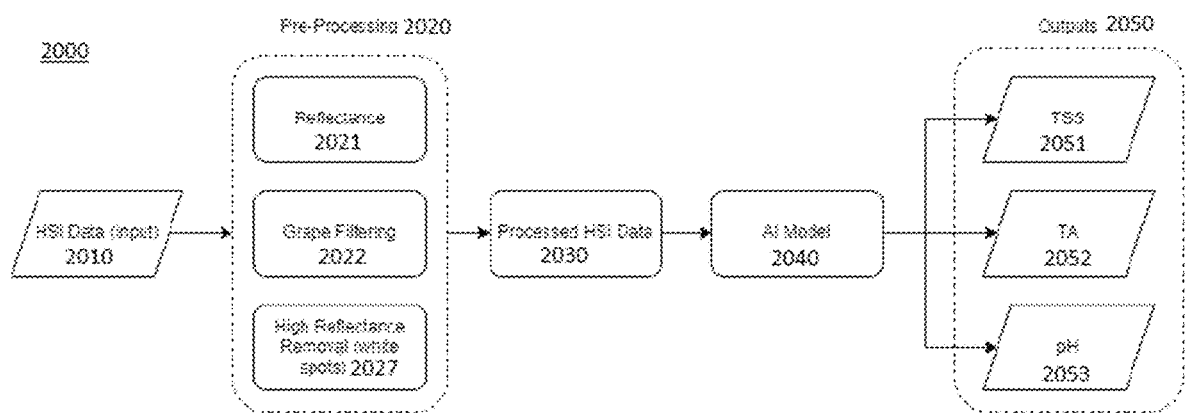
FIG. 5 is a flowchart showing an image processing process performed according to a preferred embodiment of the present invention.

FIG. 5 is a flowchart showing an image processing process 2000 performed according to a preferred embodiment of the present invention.

In the image processing process 2000, HSI data is input in operation 2010. Operation 2010 in FIG. 5 can include data from operation 1100 described above with respect to FIGS. 4A-4F. The data captured by the HSI camera is raw image data that includes all reflections and a full wavelength spectrum, and this raw image data is captured for each grape bunch, for example. The raw image data includes background data, for example, leaves or vines, and this background data has a spectra that is different from the spectra of the grapes of the grape bunch. In operation 2020, pre-processing is performed on the raw image data.

Prior to performing further processing, the raw image data is first converted to reflectance data in operation 2021. The reflectance data provides a meaningful measurement of the image data. Operation 2021 includes illumination compensation, which is performed on the reflectance data according to a white reference and a dark reference. The white reference can be a predetermined reference that is obtained by taking a picture with the HSI camera of a white object with known reflectance values before performing the processes shown in FIGS. 4A-4D. Alternatively, the white reference can be determined for each grape bunch by including a white object with known reflectance values in each image generated by the HSI camera, for example, a rectangular-shaped white object included in a bottom portion of some or all images generated by the HSI camera. An average spectrum of the white reference can be used. Variations in the dark reference generally only introduce a negligible amount of noise, and thus a constant dark reference value can be applied. The corrected data generated by the reflectance processing in operation 2021 can be used to further train an AI model, for example.

Figure 6:
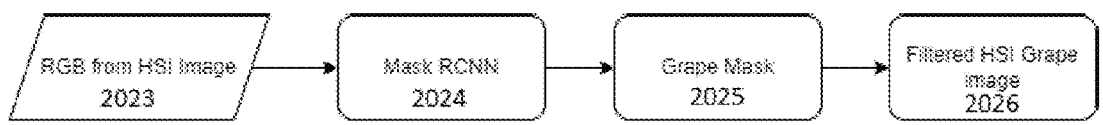
FIG. 6 shows sub-operations that are performed in a grape filtering operation of FIG. 5.

The HSI data, which is captured per grape bunch as described above with respect to FIGS. 4A-4F, includes background data. Accordingly, in operation 2022, grape filtering is performed to eliminate the background data and preserve only the spectra data of the grape bunch. FIG. 6 shows sub-operations that are performed in the grape filtering operation 2022. First, in operation 2023, an RGB image is derived from the HSI data and transmitted to an AI based network. As an example, the AI based network that performs the grape filtering can include an Instance Segmentation network, which is a robust Deep Learning model that is trained on grape images. In a preferred embodiment of the present invention, an instance segmentation model of the Instance Segmentation network can include a Mask RCNN (Region Based Convolutional Neural Network), shown in operation 2024. The AI based network then outputs, in operation 2025, a mask of the grape bunch alone (not including the background) for the RGB image derived from the HSI data. This mask can be applied to the HSI image corresponding to the HSI data to filter out the background from the grape bunch, as shown in operation 2026. For example, the mask can be applied to the HSI image corresponding to the HSI data to remove any data that does not correspond to the detected grape bunch. As a specific example, the mask can be applied to generate a grape berry mask that filters out non-berry regions, such as leaves, stems, and the like.

Due to the spheroidal shape and generally glossy texture which provide grapes with a highly reflective surface, an HSI image of a grape bunch may include high reflectance regions that appear as white spots in the HSI image. These high reflectance regions have relatively high spectra values and can appear as white spots in the HSI image. Accordingly, in operation 2027, high reflectance spectra removal (white spot removal) is performed on the HSI data corresponding to the HSI data. To detect and then remove white spots from the HSI image, a robust algorithm known as adaptive thresholding is applied in operation 2027. The adaptive thresholding algorithm calculates the threshold values for smaller regions with respect to the surrounding regions of these smaller regions, and then the adaptive thresholding algorithm applies the calculated threshold values to detect and remove high reflectance values. Accordingly, spectra that lie outside of a range for grape detection are able to be removed from the HSI image corresponding to the HSI data.

As shown in operation 2030, the above processes provide processed HSI data. The processed HSI data can then be applied to an AI model to predict the quality attributes of grapes, in operation 2040. To predict grape quality attributes, a partial least squares (PLS) regressor model can be implemented. The PLS regressor model is a regression technique that reduces predictors to a smaller set of uncorrelated components and performs a least squares regression on these components, instead of on the original data. The PLS regressor model can perform simultaneous decomposition of predictor variables and target variables such that the covariance between the two is maximum. The AI model then provides one or more outputs as shown in operation 2050. The PLS regressor model is able to predict one or more attributes of grapes, including Total Soluble Solids (TSS) 2051, Titratable Acidity (TA) 2052, and pH attributes 2053. The outputs provided in operation 2050 are able to provide predictions regarding grape quality and/or ripeness. In operation 1130 of FIGS. 4A-4C, these predictions (prediction data) can be transmitted with the color picture.

Figure 8:
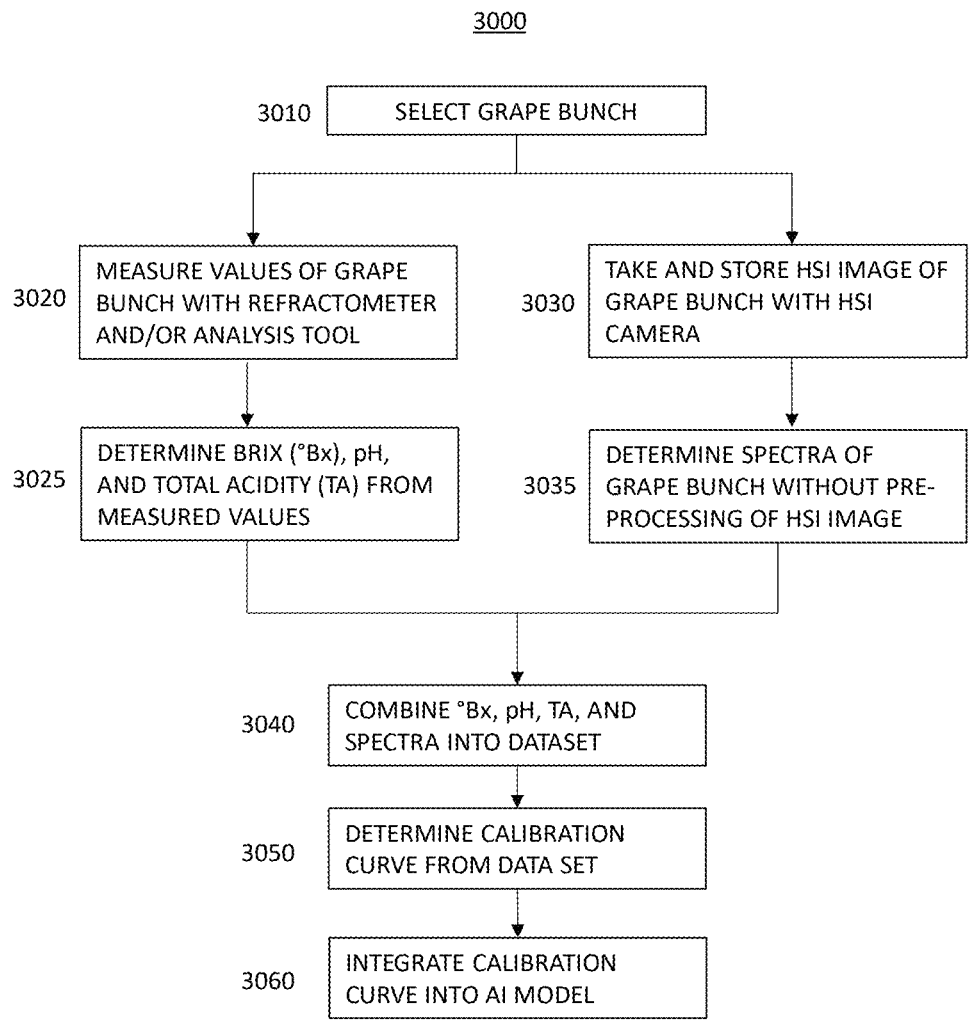
FIG. 8 is a flowchart showing a process of constructing a calibration curve to train an AI model according to a preferred embodiment of the present invention.

FIG. 8 is a flowchart showing a process 3000 of constructing a calibration curve to train an AI model according to a preferred embodiment of the present invention. As described below, the process 3000 can train an AI model (for example, the PLS regressor model) by using only HSI data and empirical measurements.

As shown in FIG. 8, a grape bunch is selected in operation 3010. In operation 3020, values of the grape bunch are measured. For example, a refractometer and other analysis tools can be used to measure values of the grape bunch. As specific examples, the refractometer can be a digital Brix refractometer that is able to measure a dissolved sugar content of a liquid sample, and other analysis tools can include a single digital instrument or meter that is able to measure one or more of sulfite ($SO_2$), pH, and TA levels. The refractometer and other analysis tools can respectively include receptacles that receive a sample to be measured and/or electrodes that are insertable into a sample to be measured. The sample can be titrated prior to measurement, depending upon the specific refractometer and other analysis tools used. The TA level can be measured in units of g/L Tartaric Acid.

According to the values measured in operation 3020, the overall Brix (° Bx), pH, and TA of the grape bunch can be determined, as shown in operation 3025.

Furthermore, an HSI image of the grape bunch is captured with an HSI camera in operation 3030. In operation 3035, spectra of the grape bunch is determined from the HSI image. Preferably, for example, the spectra of the grape bunch is determined without pre-processing of the HSI image, in contrast to the pre-processing performed in operation 2020 of FIG. 5. However, the process of determining the spectra of the grape bunch in operation 3035 may include other processing, such as smoothing or determining the second derivative of the data.

In operation 3040, the ° Bx, pH, and TA determined in operation 3025 are combined with the spectra determined in operation 3040 to provide a data set. According to the data set provide by operation 3040, a calibration curve can be determined in operation 3050. The calibration curve can then be integrated into an AI model (for example, the PLS regressor model), as shown in operation 3060, to train the AI model.

The PLS regressor model can be adapted to vary based upon different variables and conditions. For example, the PLS regressor model can vary according to the region and climate where the grapes are grown, the time of day and temperature when the grapes are imaged, the specific type of grapes (e.g., color, size, and/or variety of grape), and the like. Furthermore, vision-based deep-learning algorithms can be applied to train and refine the AI model. For example, a Mask RCNN can be used to pre-process HSI data before using the HSI data to train the PLS regressor model. AI processing of tested data can be used to determine the effectiveness of the AI model in determining prediction data from HSI images. For example, as described above, a Mask RCNN can be used to pre-process HSI data before using the HSI data to test a trained PLS regressor model.

The processes 1000 and 2000 described above are able to provide data identifying a wavelength that provides the most significant data regarding the imaged grape bunches.

A cartesian arm according to a preferred embodiment of the present invention is able to move a device, for example, a camera, along three axes. The three axes may correspond to an x-axis, a y-axis, and a z-axis. However, the present invention is not limited to three axes, and the cartesian arm can be implemented to move a device along any number of axes. In addition, the cartesian arm can be implemented to collectively move a plurality of devices, for example, a light source and a camera. As specific examples, the cartesian arm can move an HSI (hyperspectral imaging) camera, an RGB camera, a depth camera, a halogen light, and/or an LED light. The depth camera can be implemented by a LiDAR (light detection and ranging) camera or a stereo camera. As an example, the RGB camera and the depth camera can be both implemented by an INTEL® REALSENSE™ LIDAR Camera L515. As an example, the HSI camera can be a Pika L made by RESONON. In a preferred embodiment, the HSI camera can include a lens implemented by a SCHNEIDER-KREUZNACH XENOPLAN 1.4/17-0903. As further examples, the halogen light can be implemented by a THORLABS OSL2IR or a THORLABS FRI61F50. In addition, the refractometer to measure the Brix ('Bx) can be a MILWAUKEE MA871 DIGITAL BRIX REFRACTOMETER, and other analysis tools can include a VINMETRICA SC-300 SO2 & pH/TA WINE ANALYZER.

Figure 9A:
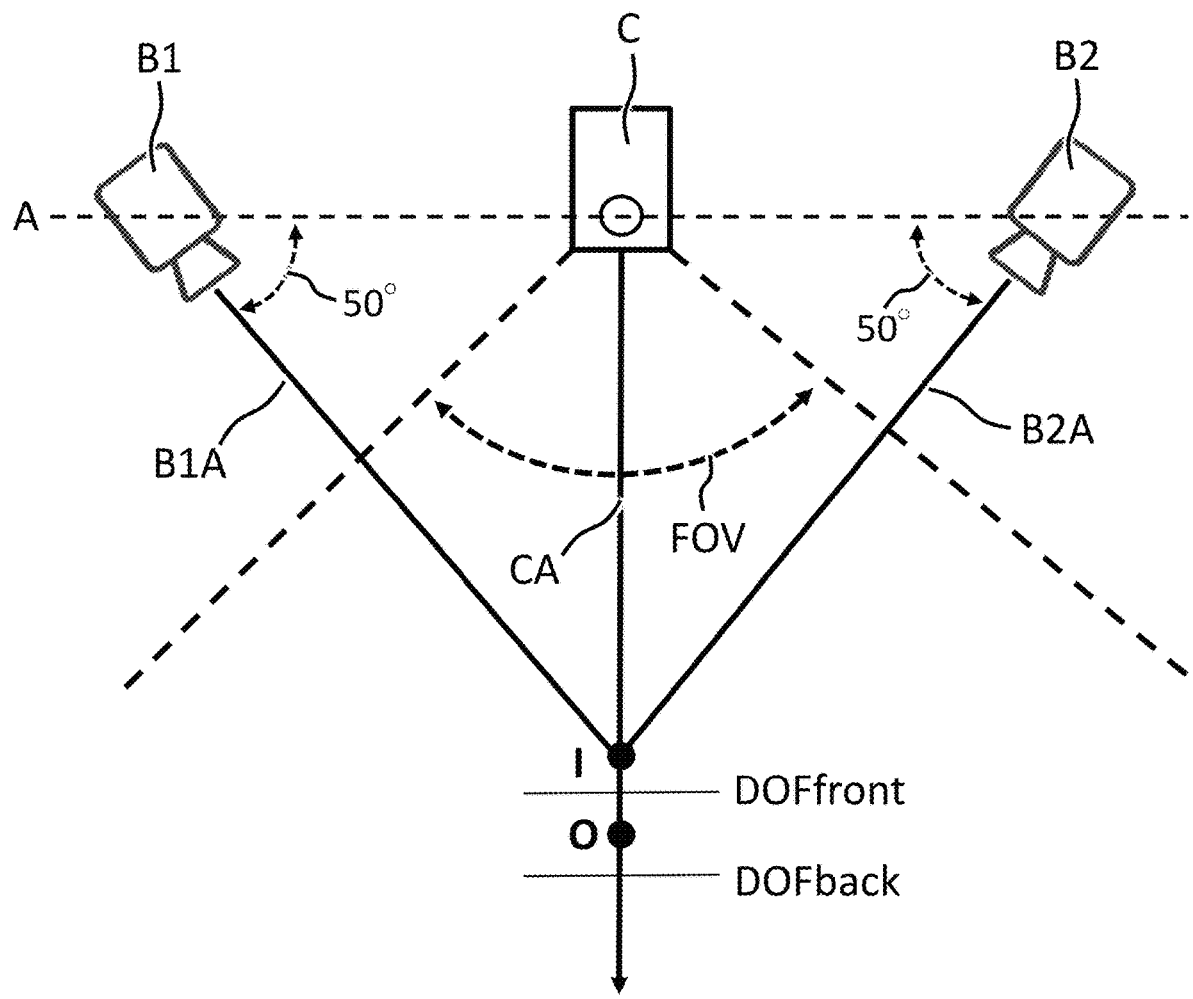
FIGS. 9A-9C show plan views of a camera system according to a preferred embodiment of the present invention.
Figure 9B:
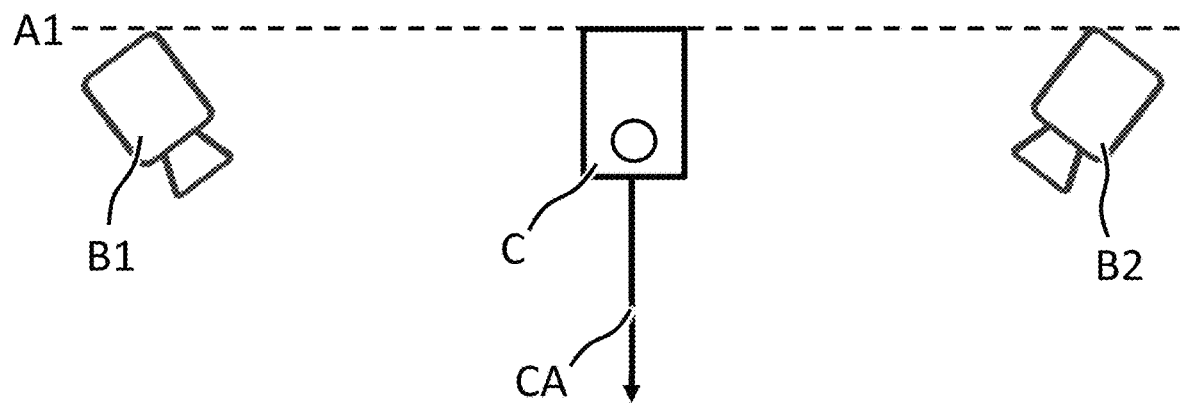
Figure 9C:
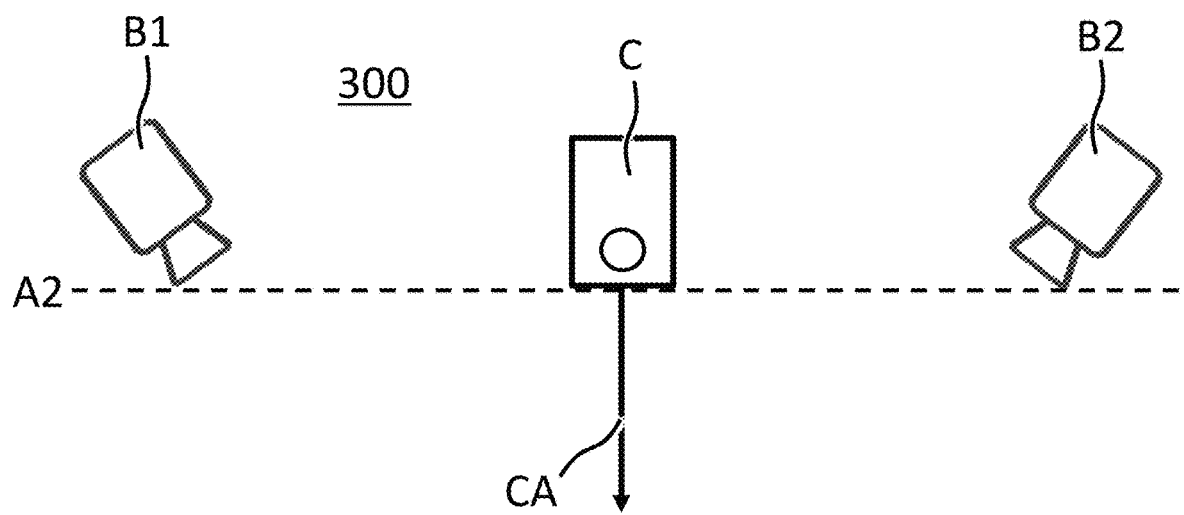

FIGS. 9A-9C show plan views of a camera system 300 according to a preferred embodiment of the present invention. As shown in FIG. 9A, the camera system 300 can detect an object O. The object O can be, for example, a grape bunch.

The camera system 300 includes a camera C and at least a first light source B1 and a second light source B2. The camera C can be, for example, an HSI camera such as the second camera 163. Each of the first light source B1 and the second light source B2 can be, for example, a halogen light source. However, the camera system 300 is not limited to an HSI camera and halogen light sources, and other types of cameras and light sources may be used.

The camera C, the first light source B1, and the second light source B2 can all be linearly or substantially linearly arranged along an axis A, as shown in FIG. 9A. The camera C can be located at or substantially at a center point between the first light source B1 and the second light source B2. That is, the camera C can be equidistant or substantially equidistant from the first light source B1 and the second light source B2.

The camera C, the first light source B1, and the second light source B2 can be arranged to ensure structural stability of the camera system 300. For example, as shown in FIG. 9B, a rearmost edge of each of the camera C, the first light source B1, and the second light source B2 can be arranged along an axis A1. The rearmost edge can be defined as a point or surface of each of the camera C, the first light source B1, and the second light source B2 that is farthest away from a main optical axis CA of the camera C. As another example, as shown in FIG. 9C, a foremost edge of each of the camera C, the first light source B1, and the second light source B2 can be arranged along an axis A2. The foremost edge can be defined as a point or surface of each of the camera C, the first light source B1, and the second light source B2 that is closest to the main optical axis CA of the camera C. According to other preferred embodiments of the present invention, the camera C, the first light source B1, and the second light source B2 can be arranged so that each of their structural midpoints or centers of gravity, in plan view, are arranged or substantially arranged along a single axis.

Preferably, for example, the camera C, the first light source B1, and the second light source B2 are arranged so that the first light source B1 and the second light source B2 are not within a field of view FOV of the camera C. Further preferably, for example, the camera C, the first light source B1, and the second light source B2 are arranged so that light emitted from each of the first light source B1 and the second light source B2 does not cast a shadow of the camera C within the field of view FOV of the camera C.

The camera C is preferably, for example, a line scan camera that is able to move along a scanning direction, as described below with respect to FIGS. 10 and 11. The scanning direction can be aligned with the axis A. The scanning direction can be a horizontal direction.

The first light source B1 and the second light source B2 are arranged so that a main optical axis B1A of the first light source B1 intersects with a main optical axis B2A of the second light source at an intersection point I. The main optical axis CA of the camera C can also intersect with or approximately intersect with the intersection point I. An angle between the main optical axis B1A of the first light source B1 and the axis A can be about 50°, and an angle between the main optical axis B2A of the second light source B2 and the axis A can also be about 50°.

Preferably, for example, the intersection point I is not located within a depth of field of the camera C. In particular, the intersection point I can be located closer to the camera C than the depth of field of the camera C. That is, the intersection point I can be located closer to the camera C than an entirety of the depth of field of the camera C.

The depth of field of the camera C is a distance between a nearest point and a furthest point from the camera C at which the object O is able to be imaged by the camera C with an acceptably sharp focus. For example, an acceptably sharp focus can be experimentally determined and/or can be set to optimize particular parameters such as brightness or intensity. In particular, an acceptably sharp focus for the depth of field of the camera C can be determined or set by a user according to a predetermined circle of confusion δ, as explained below.

The nearest point at which objects are able to be imaged by the camera C with an acceptably sharp focus ($DOF_{Front}$) can be determined by the following equation (1), and the farthest point at which objects are able to be imaged by the camera C with an acceptably sharp focus ($DOF_{Back}$) can be set by the following equation (2).

$$DOF_{Front} = \frac{\delta \times F \times WD^2}{FL^2 + \delta \times F \times WD} \quad (1)$$

$$DOF_{Back} = \frac{\delta \times F \times WD^2}{FL^2 - \delta \times F \times WD} \quad (2)$$

In the above equations (1) and (2), δ is the predetermined circle of confusion, F is the aperture of the camera C, WD is a working distance, and FL is the focal length of the camera C. The predetermined circle of confusion δ can be experimentally determined by a user or set by the user according to predetermined parameters. For example, the predetermined circle of confusion δ can be determined or set according to a size of a sensor of the camera C or a lens shape of the camera C. Preferably, for example, the predetermined circle of confusion δ can be determined or set to be approximately equal to a pixel size of the sensor of the camera C, such as a side length or a diagonal length of an individual pixel of the sensor of the camera C. The aperture F is a physical parameter for the diameter of a diaphragm opening in the camera C. The aperture F can be calculated by dividing the focal length FL by a predetermined effective aperture. The working distance WD is the length between the object O and the center of the lens of the camera C. For example, the camera C can be configured to image the object O at a constant or substantially constant working distance WD based on the measurement results with an RGB camera, a depth camera, a combined RGB camera and depth camera, a stereo camera, or the like.

Figure 10:
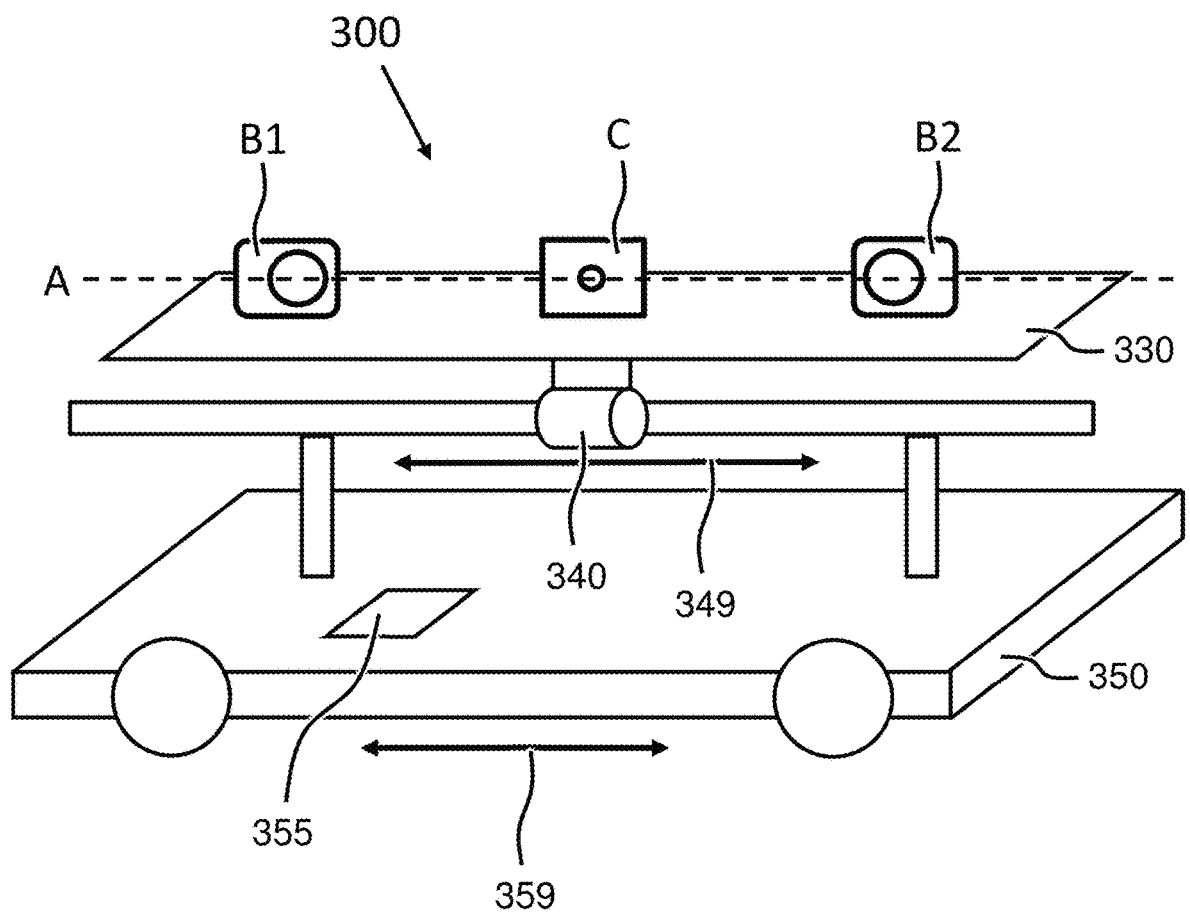
FIG. 10 shows a perspective view of the camera system shown in FIG. 9A mounted to a plate and a travel unit.

FIG. 10 shows an example of the camera system 300 shown in FIG. 9A mounted to a plate 330 and a travel unit 350.

Each of the camera C, the first light source B1, and the second light source B2 can be fixed to the plate 330 or a similar element. The camera C can be fixed to a center portion of the plate 330, the first light source B1 can be fixed to a first end of the plate 330, and the second light source B2 can be fixed to a second end of the plate 330. The plate 330 can be movable along a scanning direction 349 or the axis A.

According to a preferred embodiment of the present invention, as shown in FIG. 10, the plate can be directly fixed to a slider 340 that is able to move along the scanning direction 349 or the axis A, and the slider 340 can be configured to control a horizontal position of the camera C during imaging by the camera C, such as line scanning. The slider 340 can be a horizontal cartesian arm that is able to move along a single axis. The horizontal cartesian arm can be implemented by a cartesian arm included in the cartesian arm system 100 described above with respect to FIGS. 1-3. The horizontal cartesian arm can be mounted to one or more further cartesian arms that are able to move along one or more additional axes, and the one or more further cartesian arms can be configured to set an initial position of the camera C in front of an object O to be imaged.

According to another preferred embodiment of the present invention, the camera C, the first light source B1, and the second light source B2 can be fixed to separate plates or the like. FIG. 11 shows an example of the camera system 300 shown in FIG. 9A with components of the camera system mounted to individual plates and to the travel unit 350.

Figure 11:
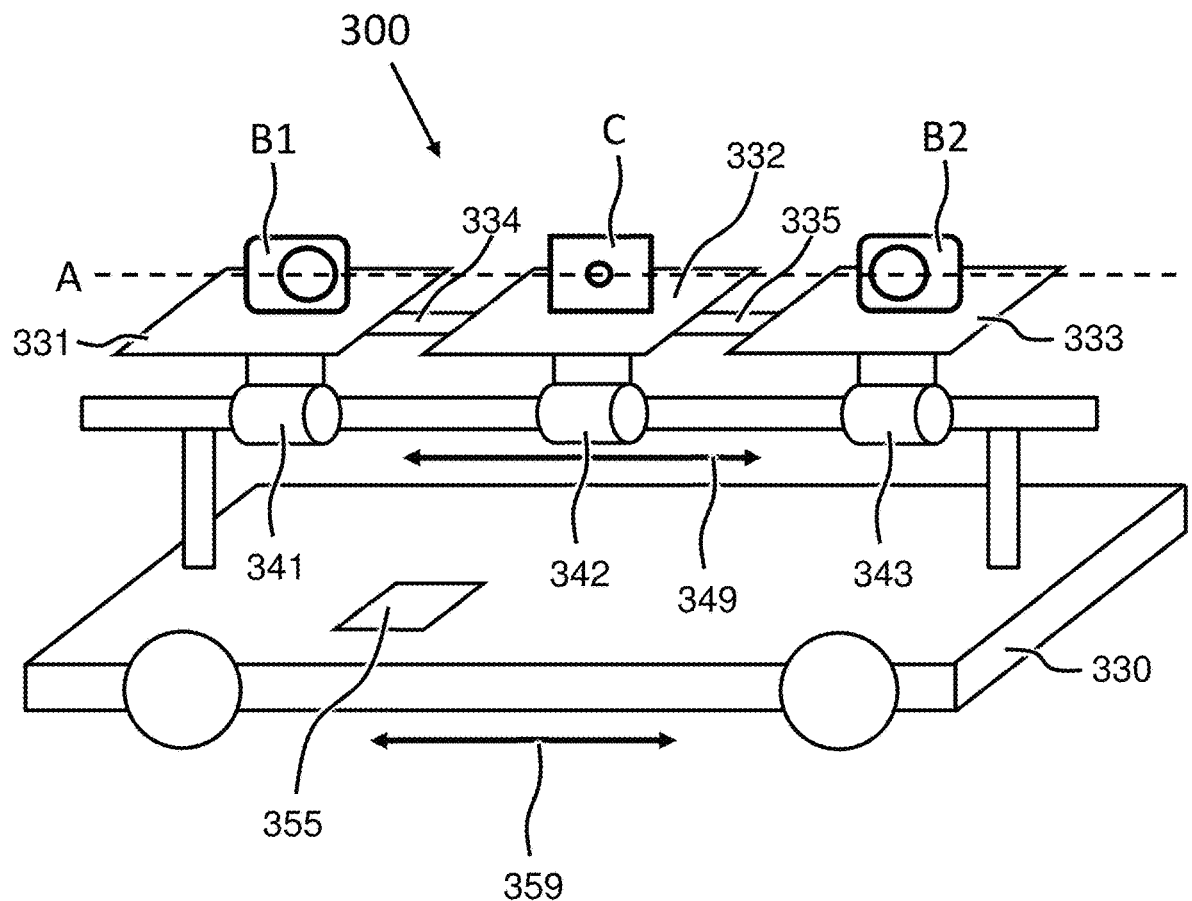
FIG. 11 shows a perspective view of the camera system shown in FIG. 9A with components mounted to separate plates.

As shown in FIG. 11, the first light source B1 can be fixed to a first plate 331, the camera C can be fixed to a second plate 332, and the second light source B2 can be fixed to a third plate 333. The first plate 331 and the second plate 332 can be connected to each other by a first support structure 334, and the first support structure 334 can fix the first plate 331 at a predetermined distance from the second plate 332. Similarly, the second plate 332 and the third plate 333 can be connected to each other by a second support structure 335, and the second support structure 335 can fix the third plate 333 at a predetermined distance from the second plate 332.

As further shown in FIG. 11, each of the first to third plates 331 to 333 can include a respective slider 341 to 343. However, a slider is not required for each of the first to third plates 331 to 333. For example, only one or two sliders may be provided, such that at least one of the first to third plates 331 to 333 is not directly connected to a slider.

According to other preferred embodiments of the present invention, the first plate 331 can be physically connected to one or both of the second plate 332 and the third plate 333.

The components of the above-described preferred embodiments can be directly or indirectly mounted on the travel unit 350, and a travelling direction 359 of the travel unit 350 can be parallel or substantially parallel to the scanning direction 349 or the axis A. Alternatively, the plate 330, or any of the first to third plates 331 to 333, can be directly mounted on the travel unit 350. The plate 330 and the first to third plates 331 to 333 can be parallel or substantially parallel to the ground upon which the vehicle travels. The travel unit 350 can be, for example, a vehicle such as an electric vehicle.

Figure 12:
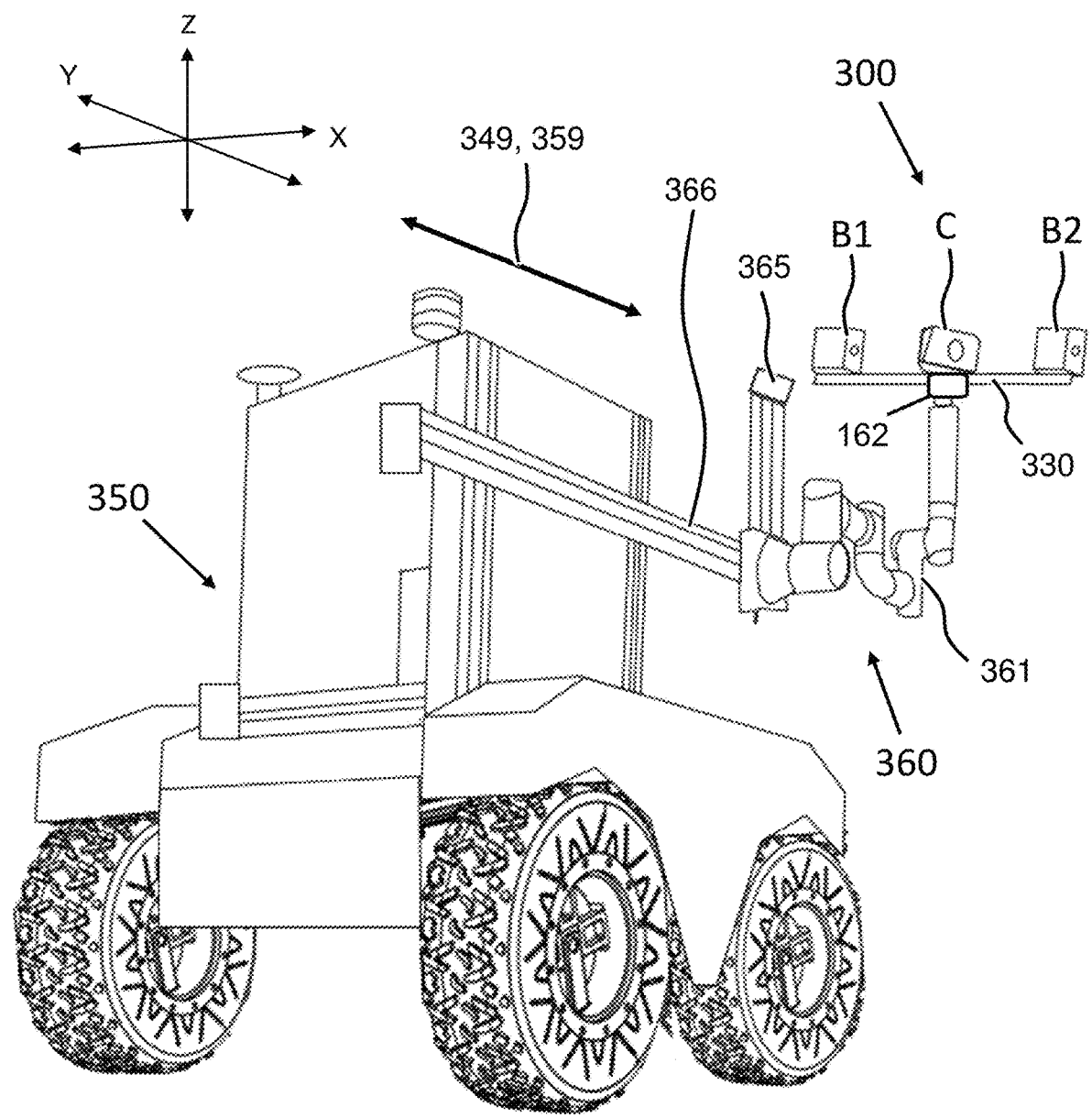
FIG. 12 shows a perspective view of the camera system shown in FIG. 9A mounted to a plate that is attached to a robotic arm.

FIG. 12 shows a perspective view of the camera system 300 shown in FIG. 9A mounted to the plate 330 and connected to the travel unit 350. FIG. 12 shows a preferred embodiment of the present invention in which the camera system 300 is connected to the travel unit 350 by at least one robotic arm and/or cartesian arm (arm system 360). The arm system 360 can be configured to set an initial position of the camera C in front of an object to be imaged.

As shown in FIG. 12, the plate 330 can be fixed to a robotic arm 361 that is movable along at least one axis. However, for example, the robotic arm 361 may be configured to move along two axes or along three axes. The robotic arm 361 can be directly connected to the travel unit 350, or the robotic arm 361 can be connected to the travel unit 350 via one or more cartesian arms 365, 366. Each of the one or more cartesian arms 365, 366 can be configured to move along a single axis. For example, as shown in FIG. 12, a first cartesian arm 365 can be configured to move along a vertical axis (the Z-axis shown in FIG. 12), and a second cartesian arm 366 can be configured to move along a horizontal axis (the Y-axis shown in FIG. 12). The movement of the second cartesian arm 366 along the horizontal axis can be parallel or substantially parallel to the scanning direction 349 and the travelling direction 359.

The robotic arm 361 can include a robotic arm known to a person of ordinary skill in the art, such the Universal Robot 3 e-series robotic arm, the Universal Robot 5 e-series robotic arm, and the Universal Robot 10 e-series robotic arm. The robotic arm 361, also known as an articulated robotic arm, can include a plurality of joints that act as axes that enable a degree of movement, wherein the higher number of rotary joints the robotic arm 361 includes, the more freedom of movement the robotic arm 361 has. For example, the robotic arm 361 can include four to six joints, which provide the same number of axes of rotation for movement. The robotic arm 361 can be controlled to move the camera C (a quality measuring device such as the second camera 163 including an HSI camera) to a predetermined position relative to an object (e.g., a grape bunch). In a preferred embodiment, the first camera 162 can also be mounted to the plate 330 such that the robotic arm 361 can be controlled to move the first camera 162 along with the camera C. However, this is non-limiting and the first camera 162 can be mounted to another portion of the camera system 300, the travel unit 350, or the arm system 360, for example.

According to a further preferred embodiment of the present invention, the arm system 360 can be fixed to one or more sliders that are able to move along the scanning direction 349, and the sliders can be configured to control a horizontal position of the camera C and the light sources B1, B2 during imaging by the camera C, such as line scanning. That is, features of the preferred embodiments of the present invention may be combined with or may replace one another, including the elements shown in FIGS. 10-12.

In the above-described preferred embodiments, a controller 355 can be configured or programmed to control movement of the travel unit 350 and to stop the travel unit 350 when the object O is within the depth of field of the camera C. According to another preferred embodiment of the present invention, the controller 355 can be configured or programmed to control movement of the travel unit 350 and to stop the travel unit 350 when the object O is within a range of motion of a robotic arm or a cartesian arm to adjust a position of the camera C such that the object O within the depth of field of the camera C.

Furthermore, the controller 355, or a separate controller, can be configured or programed to control movement of the arm system 360. For example, the controller 355 or the separate controller can be configured or programed to control the movement of the arm system 360 to position of the camera C in front of an object to be imaged.

In the above-described preferred embodiments, the controller 355 or the separate controller can be configured or programmed to control movement of the travel unit 350 and/or to control movement of the arm system 360 to maintain a constant or substantially constant working distance WD. That is, the controller 355 or the separate controller can be configured or programmed to maintain a length between the object O and the center of the lens of the camera C that is constant or substantially constant.

As shown in FIGS. 10 and 11, the travel unit 350 can include the controller 355 (not shown in FIG. 12). The controller 355 can include one or more processors and memory components, and the controller 355 can be configured or programmed to control operations of at least one of the camera system 300 and the travel unit 350. According to other preferred embodiments of the present invention, in addition to or alternatively to the controller 355 of the travel unit 350, the camera system 300 can include one or more processors and memory components that define a controller, and the controller of the camera system 300 can be configured or programmed to control operations of at least one of the camera system 300 and the travel unit 350. For example, the controller 355 of the travel unit 350 and/or the controller of the camera system 300 can be configured or programmed to control the travel unit 350 to travel in a direction that is parallel or substantially parallel to a scanning direction 349 of the camera C. Further, the controller 355 of the travel unit 350 and/or the controller of the camera system 300 can be configured or programmed to control movement of the travel unit 350 and to stop the travel unit 350 when the object O is within the depth of field of the camera C.

Figure 16:
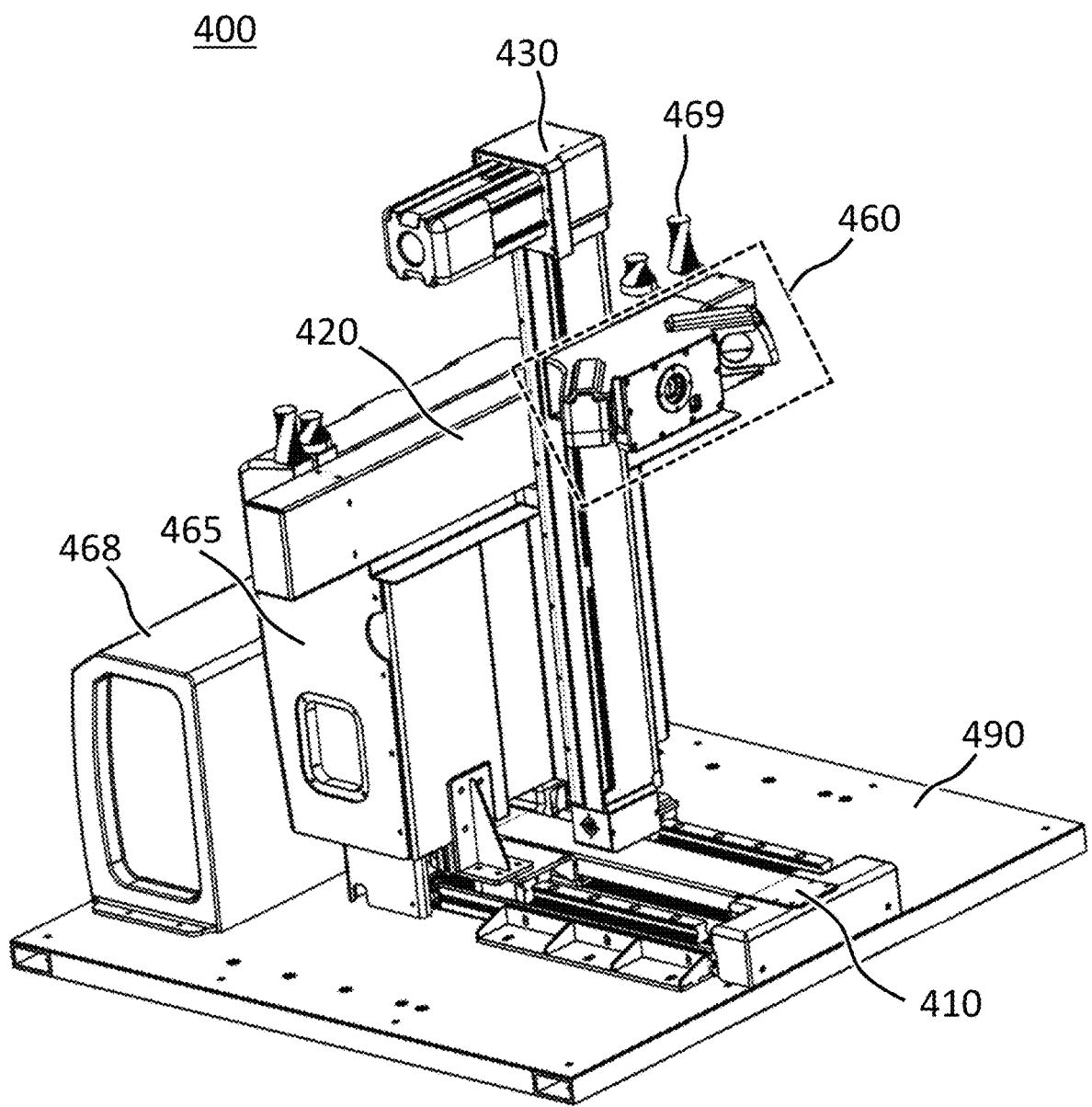
FIG. 16 shows a front perspective view of a camera system according to a preferred embodiment of the present invention.
Figure 17:
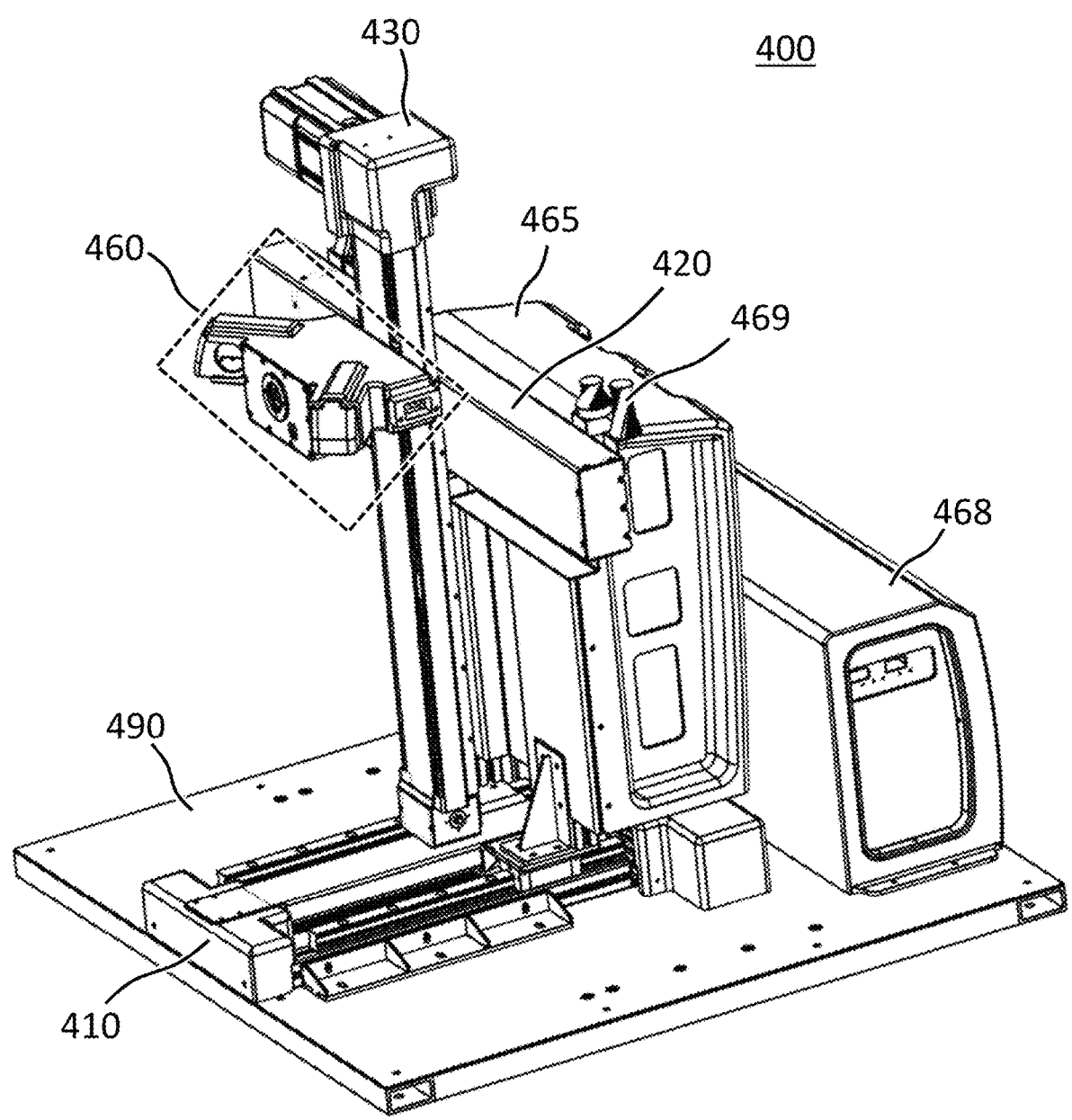
FIG. 17 shows a rear perspective view of the camera system of FIG. 16.

FIG. 16 shows a front perspective view of a camera system 400 according to a preferred embodiment of the present invention. FIG. 17 shows a rear perspective view of the camera system 400 of FIG. 16.

As shown in FIGS. 16 and 17, the camera system 400 includes a base (forward/backward) slider 410, a horizontal (scan direction) slider 420, and a vertical sider 430. The vertical slider 430 can be mounted to the horizontal slider 420, and the horizontal slider 420 can be mounted to the base slider 410. One or more devices 460, such as one or more cameras and/or light sources, can be mounted to the vertical slider 430. The base slider 410 can be mounted to a base plate 490. The base plate 490 can be fixed to a vehicle or the like, or the base plate 490 can be defined by a portion of a vehicle or the like.

Figure 18:
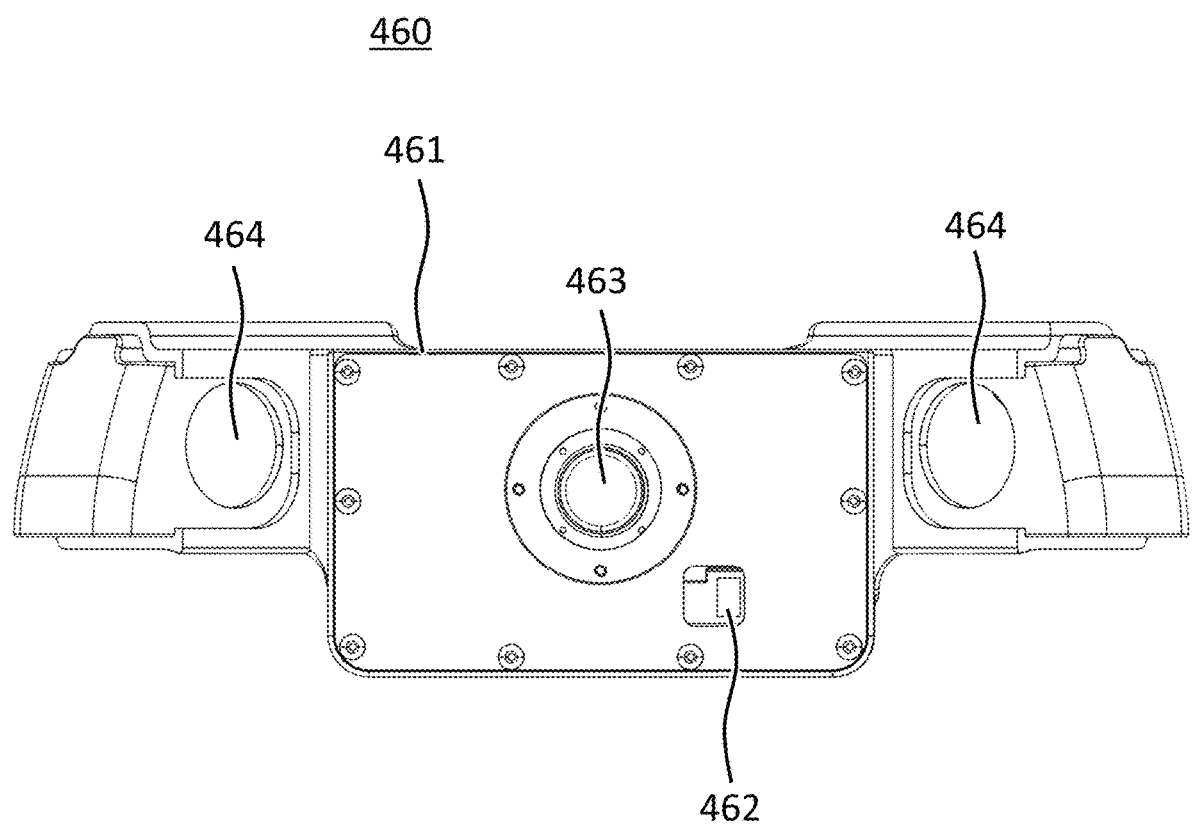
FIG. 18 shows a front view of devices included in the camera system of FIG. 16.

FIG. 18 shows a front view of the one or more devices 460 shown in FIG. 16.

As shown in FIG. 18, the one or more devices 460 can include a first camera 462, a second camera 463, and camera light sources 464 that are mounted to a bracket or housing 461 attached to the vertical slider 430. The first camera 462 can be a time-of-flight (ToF) camera, a depth camera such as a LIDAR camera, a combined RGB camera and depth camera, a stereo camera, and the like. The second camera 463 can be an HSI (hyperspectral imaging) camera. The second camera 463 including an HSI camera is a non-limiting example of a quality measuring device. For example, a second camera 463 including a multi-spectral camera, an NRI sensor, a UV sensor, and an X-ray sensor are other non-limiting examples of a quality measuring device.

The camera light sources 464 can include two light sources that are mounted on opposing sides of the bracket or housing 461, with the first camera 462 and the second camera 463 located between the camera light sources 464. The camera light sources 464 can include a halogen light source to provide a light spectrum for capturing HSI images, for example, in a range of about 400 nm to about 1000 nm.

The camera system 400 can include an electrical unit 465, which can include control electronics for one or more of the base slider 410, the horizontal slider 420, the vertical sider 430, the first camera 462, the second camera 463, and the camera light sources 464. As shown in FIGS. 16 and 17, the electrical unit 465 can be provided one or more antennas 469 for wireless communication. The camera system 400 can also include a power source 468 to provide power to one or more of the base slider 410, the horizontal slider 420, the vertical sider 430, the first camera 462, the second camera 463, and the camera light sources 464.

The electrical unit 465 can be configured or programmed to control a supply of power from the power source 468 to one or more of the base slider 410, the horizontal slider 420, the vertical sider 430, the first camera 462, the second camera 463, and the camera light sources 464. The electrical unit 465 include processor and memory components that are programmed or configured to control one or more of the base slider 410, the horizontal slider 420, the vertical sider 430, the first camera 462, the second camera 463, and the camera light sources 464. In addition, the processor and memory components of the electrical unit 465 can be configured or programmed to process image data obtained by the first camera 462 and the second camera 463.

As described above, the imaging electronics 467 and the base electronics 494 can include processors and memory components. The processors may be hardware processors, multipurpose processors, microprocessors, special purpose processors, digital signal processors (DPSs), and/or other types of processing components configured or programmed to process data. The memory components may include one or more of volatile, non-volatile, and/or replaceable data store components. For example, the memory components may include magnetic, optical, and/or flash storage components that may be integrated in whole or in part with the processors. The memory components may store instructions and/or instruction sets or programs that are able to be read and/or executed by the processors.

The base slider 410, the horizontal slider 420, and the vertical sider 430 are able to move the one or more devices 460 in three separate directions or along three separate axes. However, according to another preferred embodiment of the present invention, only a portion of the one or more devices 460 can be moved by the base slider 410, the horizontal slider 420, and the vertical sider 430, for example, only a second camera 463 or only the second camera 463 and the camera light source 464. Furthermore, the camera system 400 can be configured to linearly move the second camera 463 along only a single axis while the second camera 463 captures an image. For example, the horizontal slider 420 can be configured to linearly move the second camera 463 across a grape bunch while the second camera 463 captures an HSI image of the grape bunch.

As explained above, the electrical unit 465 can be provided one or more antennas 469 for wireless communication, and the electrical unit 465 include processor and memory components that are programmed or configured to process image data obtained by the first camera 462 and the second camera 463 and to control one or more of the base slider 410, the horizontal slider 420, the vertical sider 430, the first camera 462, the second camera 463, and the camera light sources 464. Accordingly, the electrical unit 465 can transmit and receive data with an external device, for example, a computer or a mobile phone.

The camera system 400 can be mounted to a travel unit or traveling device, for example, a vehicle or a cart. In particular, the camera system 400 can be mounted to the vehicle shown in FIG. 1 (e.g., mounted to the base frame 110 shown in FIG. 1) or to the travel unit 350 shown in FIG. 10.

Figure 19A:
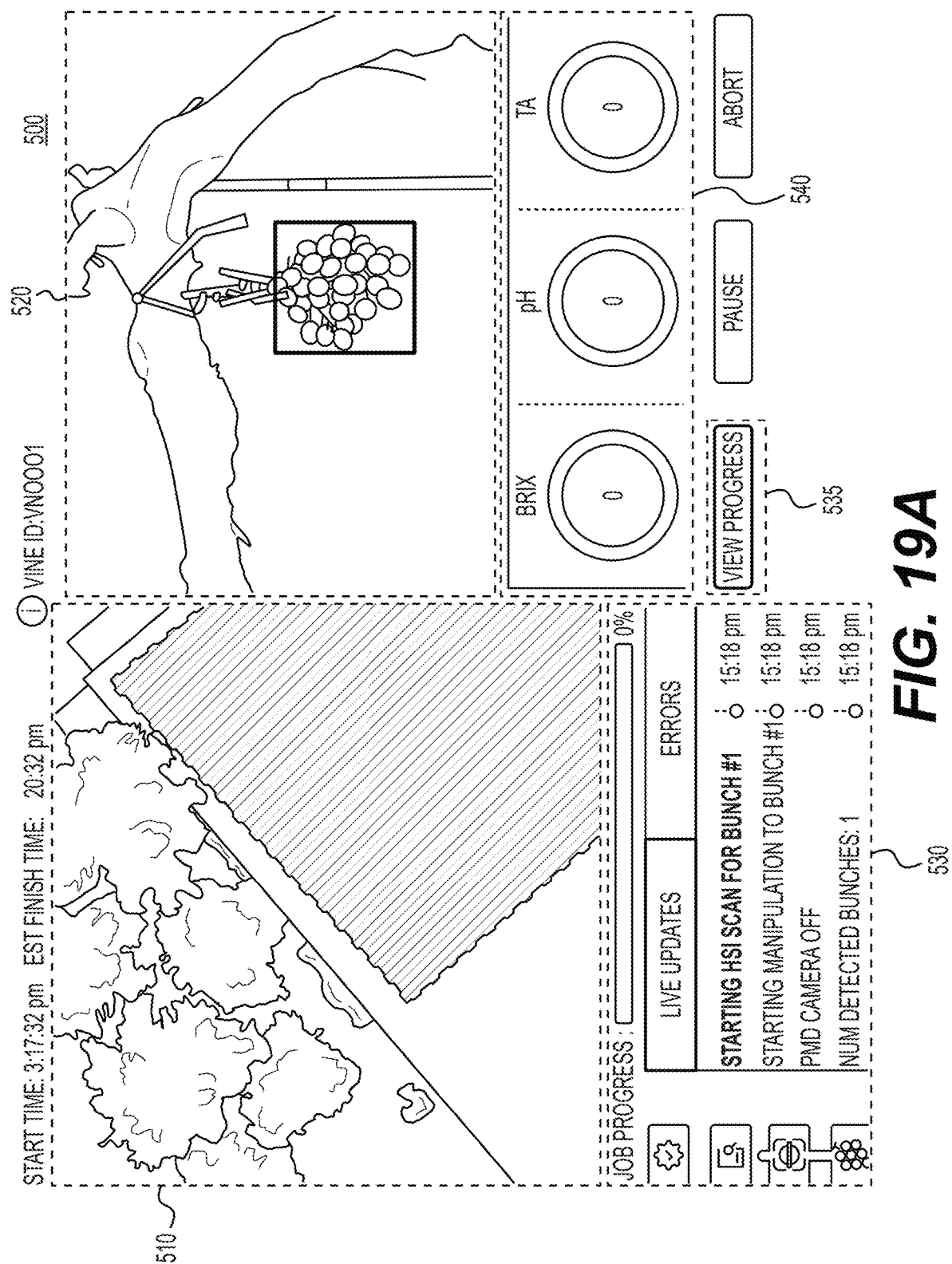
FIGS. 19A and 19B show an application display according to a preferred embodiment of the present invention.
Figure 19B:
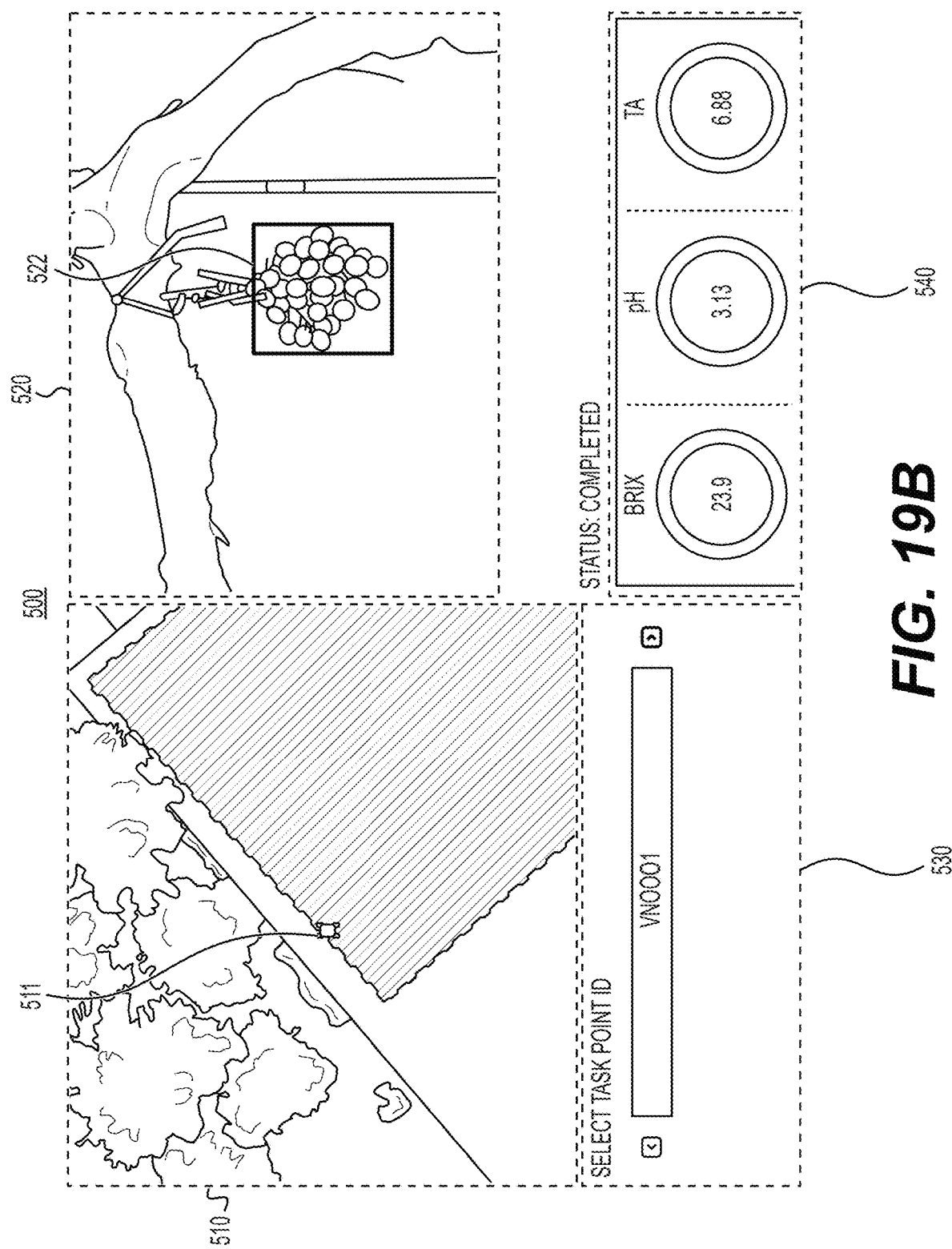

FIGS. 19A and 19B show an example of an application display 500 associated with one or more of the cartesian arm system 100 shown in FIG. 1, the camera system 300 shown in FIGS. 9A-9C, and the camera system 400 shown in FIG. 16. The application display 500 can be provided as a user interface for a user to control the operations of, and receive data from, one or more of the cartesian arm system 100, the camera system 300, and the camera system 400. As explained below, the application display 500 can include a first region 510, a second region 520, a third region 530, and a fourth region 540.

As shown in FIGS. 19A and 19B, the display includes the first region 510 that can display an aerial image. In the first region 510, a work area can be shown in a representative view. For example, as shown in FIGS. 19A and 19B, a work area can be represented by one or more areas in solid color(s) or greyscale. In the first region 510, an icon 511 can indicate a particular agricultural item or task point can be selected by a user. When a particular agricultural item or task point is selected, other regions of the application display 500 can be updated, as discussed below with respect to the third region 530 and the fourth region 540.

FIGS. 20A and 20B show example views of the first region 510 of the application display 500. As shown in FIGS. 20A and 20B, the work area can be represented by polygons that define an irregular grid, and a color or greyscale value of each of the polygons can represent a particular value, such as a quality score, of agricultural items in different sections of the work area. For example, a color or greyscale value of each of the polygons can represent Brix values of grape bunches within the work area. The first region 510 can hide items that are not associated with the work area, for example, trees that may obscure the view the information of the agricultural items in the work area.

As shown in FIGS. 20A and 20B, representative samples of agricultural items can be identified by dots in the first region 510. Each of the polygons can define a portion of the work area that is closest to a particular sample point according distance between each agricultural item and the sample points. For example, the polygons can be determined according to a Euclidean distance from each of the sample points as shown in FIG. 20A or a Manhattan distance from each of the sample points as shown in FIG. 20B. According to another preferred embodiment of the present invention, each of the polygons can be determined to each have an equal or substantially equal number of agricultural items.

Figure 21A:
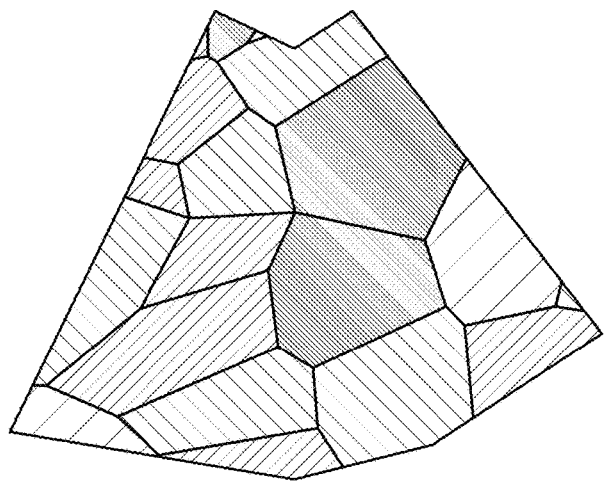
FIGS. 21A-21C show modifications to the example view in FIG. 20A of the first region of the application display of FIGS. 19A and 19B.
Figure 21B:
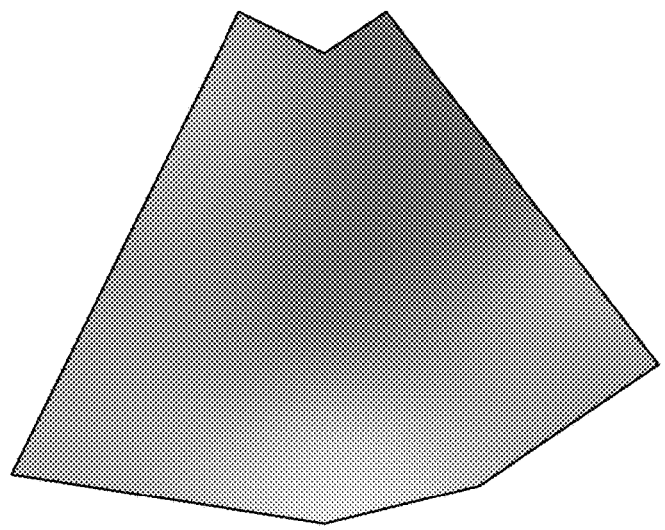
Figure 21C:
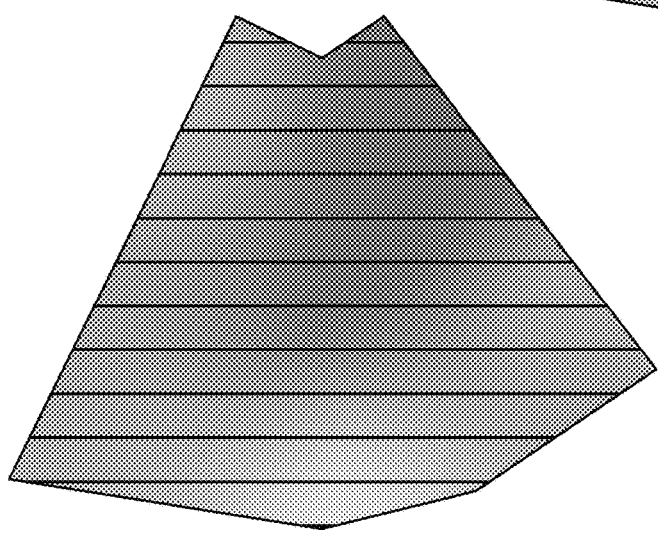

FIGS. 21A-21C show modifications to the example view in FIG. 20A of the first region of the display of FIGS. 19A and 19B. As shown in FIG. 21A, an irregular grid including polygons with varying color or greyscale values can be generated to represent the work area. As shown in FIG. 21B, a heatmap with varying color or greyscale values can be generated to represent the work area. For example, the heatmap shown in FIG. 21B can be determined or generated based upon the irregular grid shown in FIG. 21A to provide a view that is able to be more readily understood by a user. As shown in FIG. 21C, lines representing rows of agricultural items can be displayed on the heatmap shown in FIG. 21B to further facilitate a user's understanding of the status of the work area.

The first region 510 can also display icon(s) to indicate portion(s) of the work area that have significantly lower quality score than an overall average value of the work area, for example, portion(s) that have a quality score that is more than one standard deviation less than the overall average.

The first region 510 can also display icon(s) to indicate agricultural items that may not receive sufficient sun exposure. For example, a determination of insufficient sun exposure may be based upon a density of agricultural items, or based upon a determination that agricultural items may be crowded and have overlapping leaves.

Accordingly, the first region 510 is able to display the work area as a representative image for easy understanding by a user.

As shown in FIGS. 19A and 19B, the display includes the second region 520 that can display a crop image. The crop image displayed in the second image can include an image of one or more agricultural items and polygon mask(s) 522 formed around each of the one or more agricultural items. The polygon mask(s) can be similar to the polygon masks 141 shown in FIG. 14.

As shown in FIG. 19A, the display includes the third region 530 that can display step and progress information of an autonomous vehicle. The third region 530 can be a selectable region in which a user can select agricultural items or task points.

As shown in FIG. 19B, when a particular agricultural item or task point is selected by a user in the first region, the third region 530 can instead display information regarding the selected agricultural item or task point, for example, a unique alphanumeric identifier of the selected agricultural item or task point. Alternatively or in addition, the third region 530 can display information regarding an agricultural item or task point when a button is selected by a user in a different region of the application display 500, for example, a view progress button as shown in FIG. 19A. Furthermore, as shown in FIG. 19B, the third region 530 can include an input selector that enables the user to select another agricultural item or task point.

Figure 22:
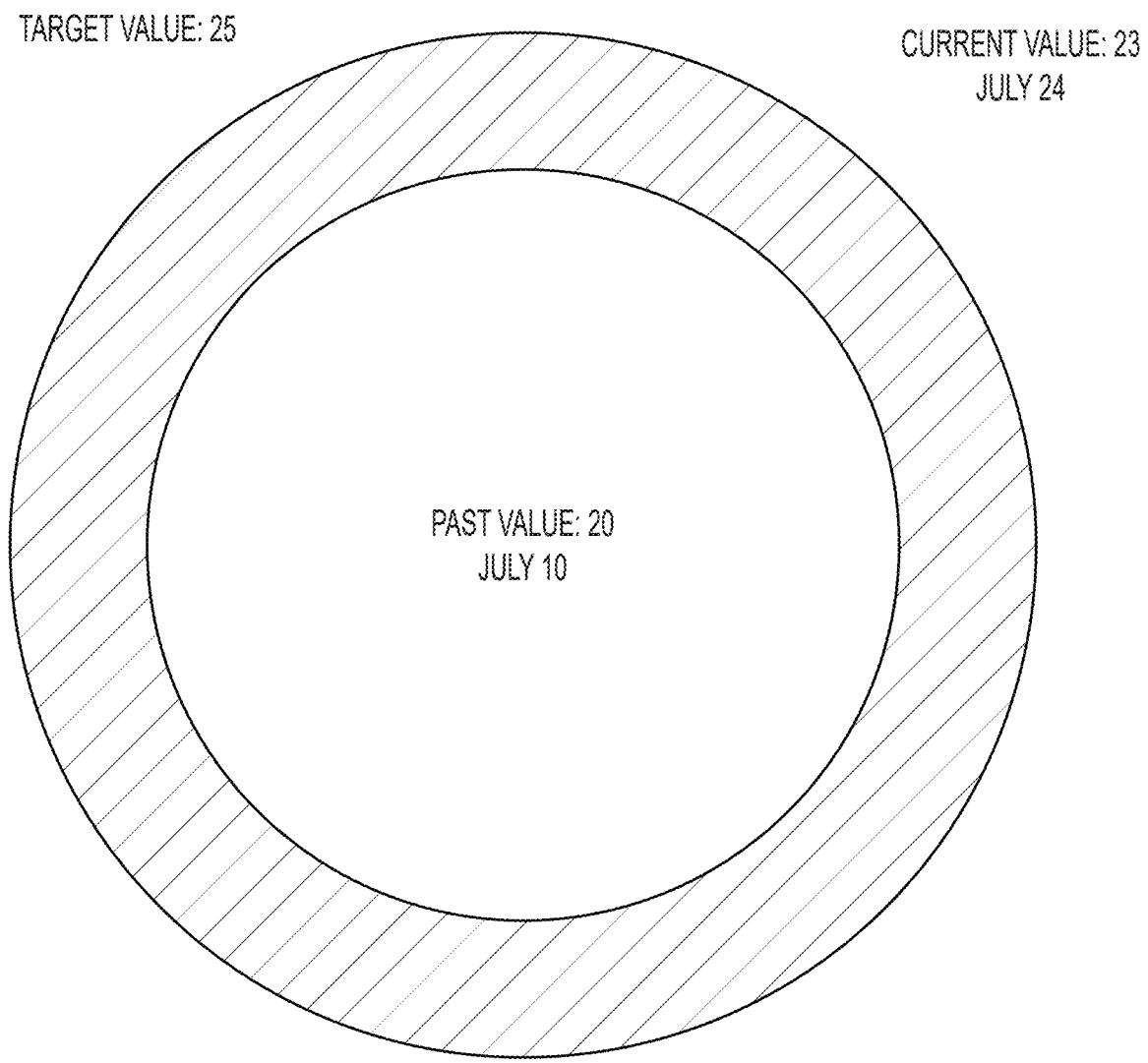
FIG. 22 shows an example view of a portion of a fourth region of the application display of FIGS. 19A and 19B.

As shown in FIGS. 19A and 19B, the display includes the fourth region 540 that can display quality score(s). For example, the fourth region 540 can display Brix, pH, and TA levels as values for quality scores. FIG. 22 shows an example view of a portion of the fourth region 540 of the application display 500. As shown in FIG. 22, the fourth region 540 can display detailed information regarding the quality score(s), such as historical value(s), a current value, and a target value for Brix.

As shown in FIG. 19B, when a particular agricultural item or task point is selected by a user in the first region, the fourth region 540 can display the quality score(s) for the selected agricultural item or task point.

Figure 23:
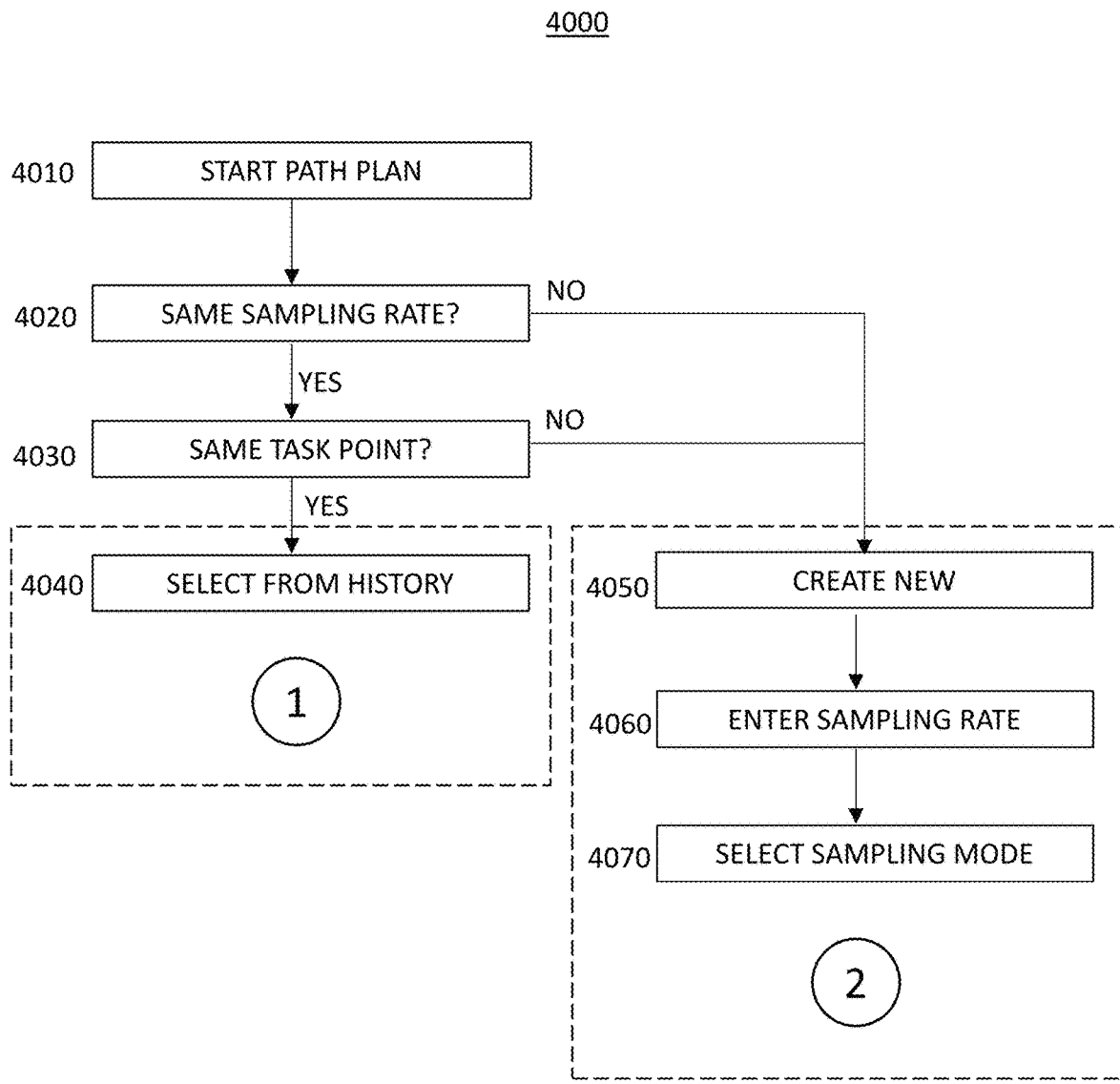
FIG. 23 is a flowchart showing a process of path planning according to a preferred embodiment of the present invention.

FIG. 23 is a flowchart showing a process 4000 of path planning according to a preferred embodiment of the present invention. The process 4000 shown in FIG. 23 can be implemented with one or more of the cartesian arm system 100 shown in FIG. 1, the camera system 300 shown in FIGS. 9A-9C, and the camera system 400 shown in FIG. 16.

As shown in FIG. 23, the process 4000 is started at operation 4010 to select a path plan and proceeds to operation 4020. In operation 4020, the process 4000 determines if a previous sampling rate is to be applied as the next sampling rate. That is, the process 4000 determines if the same sampling rate is to be applied. For example, the sampling rate can be set as a predetermined number of agricultural items to be sampled, or as a predetermined proportion (e.g., percentage) of agricultural items to be sampled. The sampling rate can be associated with a sampling mode, for example, a uniform sampling mode to sample agricultural items at regular intervals, a speed sampling mode to quickly and efficiently sample agricultural items (e.g., sampling only a portion of rows of agricultural items), a random sampling mode, and the like.

If the same sampling rate is to be applied (YES in operation 4020), the process 4000 proceeds to operation 4030. In operation 4030, the process 4000 determines if a previous task point is to be applied as the next task point. That is, the process 4000 determines if the same task point is to be applied. For example, the process 4000 can determine if an autonomous vehicle that will execute a determined path is to begin at the same starting point or will travel along a previously determined path of task points.

If the same task point is to be applied (YES in operation 4030), the process 4000 proceeds to operation 4040. In operation 4040, a path plan can be selected from a history of path plan(s). As a result of operation 4040, (1) a same grid size and shape, or a same heatmap, can be applied for path planning. For example, a size and shape of the polygons in the irregular grids shown in FIGS. 20A, 20B, and 21C can be maintained.

If the same sampling rate is not applied (NO in operation 4020), or if the same task point is not applied (NO in operation 4030), the process 4000 proceeds to operations 4050, 4060, and 4070. In operation 4050, a new path plan is created. In operation 4060, a sampling rate is determined for the new path plan. In operation 4070, a sampling mode is determined for the new path plan. As described above, the sampling mode can be, for example, one of a uniform sampling mode, a speed sampling mode, a random sampling mode, and the like. As a result of operations 4050, 4060, and 4070, (2) a new grid size and shape, or a new heatmap, can be applied to path planning for the new path. For example, a size and shape of the polygons in the irregular grids shown in FIGS. 20A, 20B, and 21C can be changed according to the sampling rate, sampling mode, or task point(s) of the new path.

Figure 24:
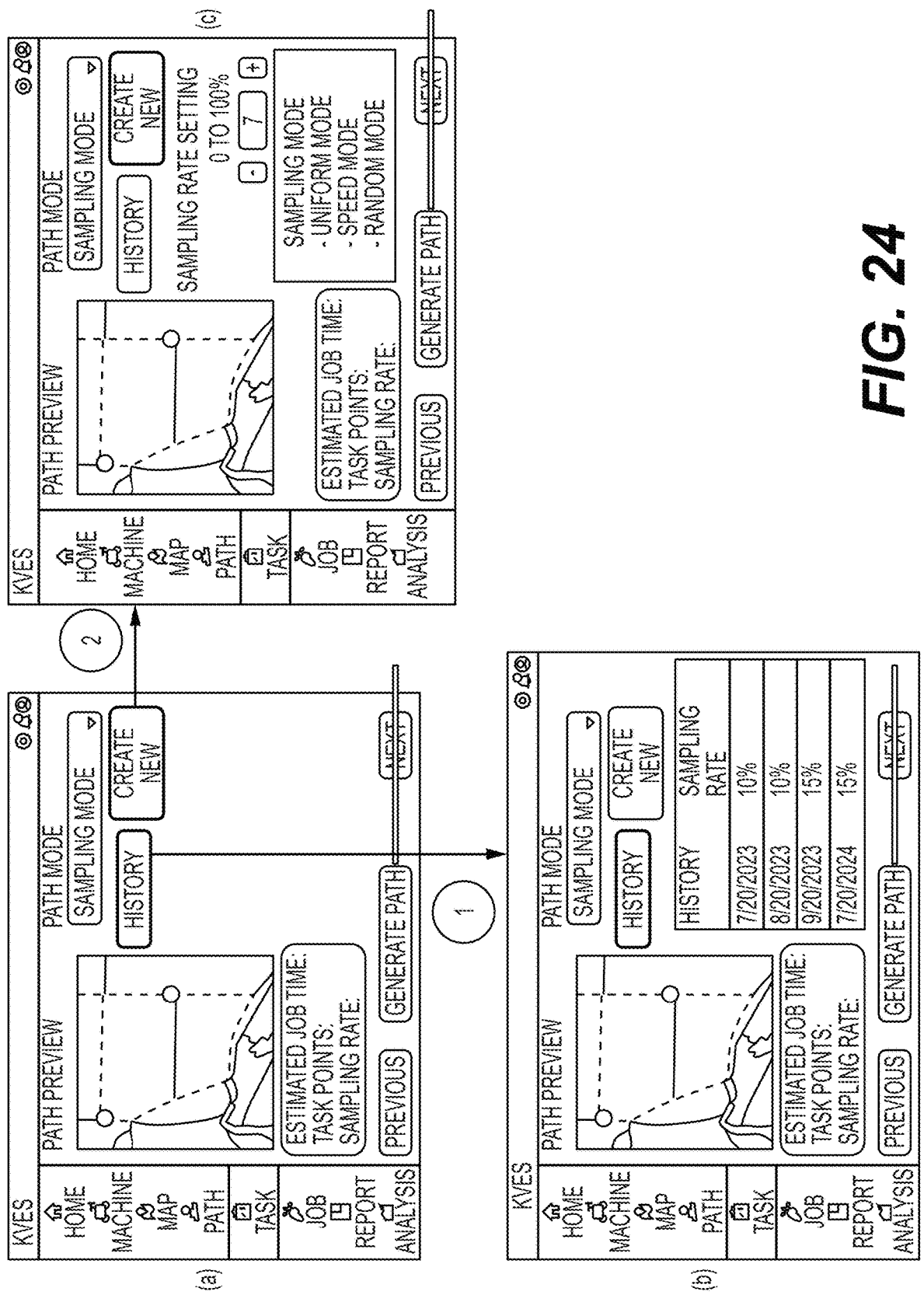
FIG. 24 shows an application display associated with the process of path planning shown in FIG. 23.

FIG. 24 shows an application display associated with the process of path planning shown in FIG. 23. The application display shown in FIG. 24 can be implemented with one or more of the cartesian arm system 100 shown in FIG. 1, the camera system 300 shown in FIGS. 9A-9C, and the camera system 400 shown in FIG. 16.

As shown in (a) of FIG. 24, a path plan can be selected from a history of path plans, either by the operations shown in the process 4000 of FIG. 24 or by a user manually selecting a "History" button or the like. As shown in (b) of FIG. 24, historical path plans can be displayed along with corresponding sampling rates, and the historical path plans can be selected, either by the operations shown in the process 4000 of FIG. 24 or by a user's input. As shown in (c) of FIG. 24, a new path plan can be created and a sampling rate and a sampling mode can be selected, either by the operations shown in the process 4000 of FIG. 24 or by a user's input.

Figure 25A:
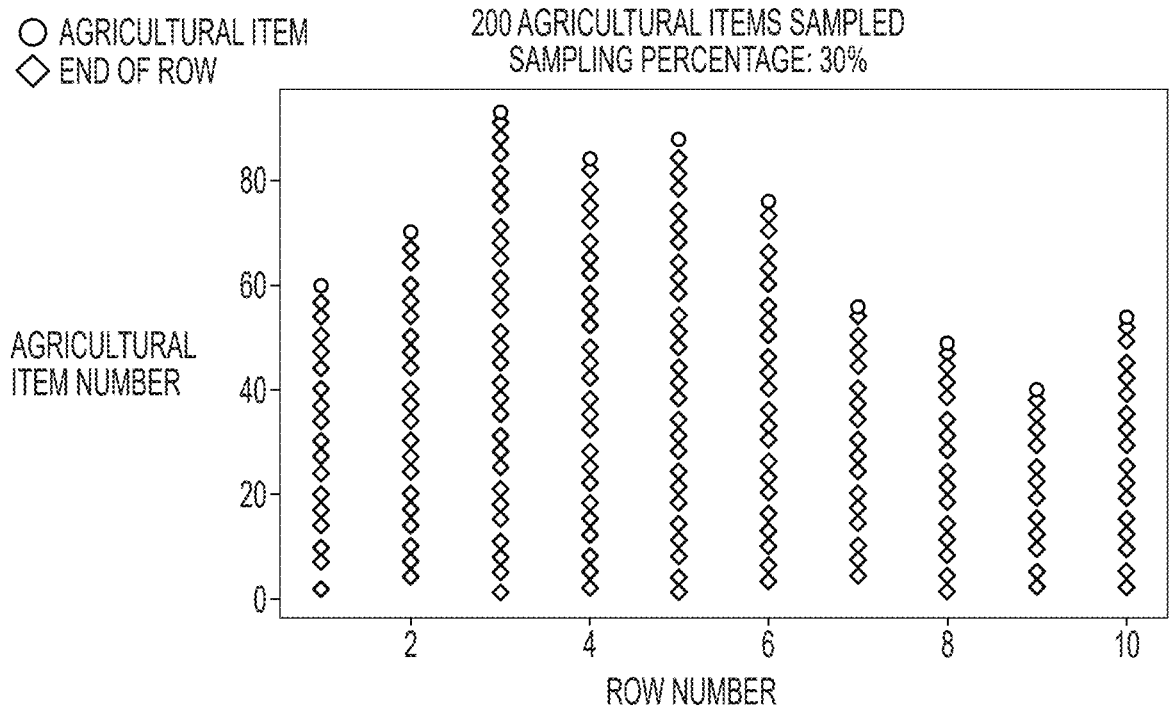
FIGS. 25A and 25B show examples of a uniform sampling mode and a speed sampling mode according to a preferred embodiment of the present invention.
Figure 25B:
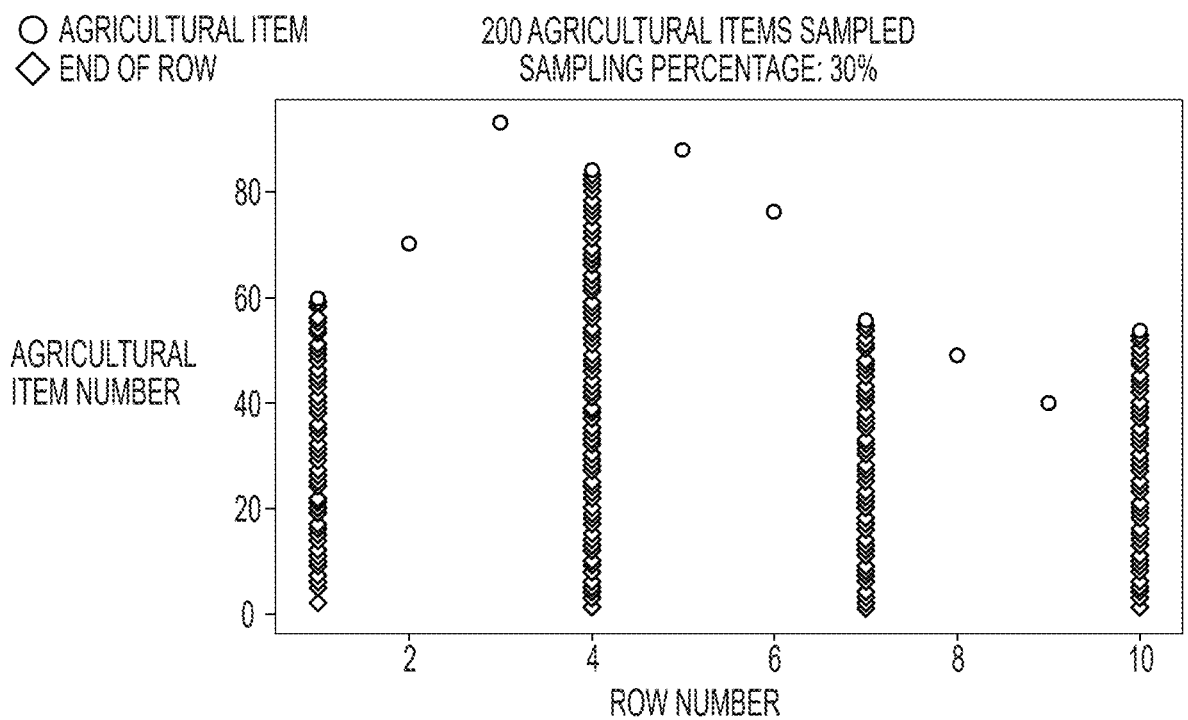

FIG. 25A shows an example of a uniform sampling mode according to a preferred embodiment of the present invention, and FIG. 25B shows an example of a speed sampling mode according to a preferred embodiment of the present invention.

As shown in FIGS. 25A and 25B, the same number of agricultural items (e.g., 200) in a target area can be sampled in both the uniform sampling mode and the speed sampling mode, and the sample proportion of agricultural items (e.g., 30%) can be sampled in both the uniform sampling mode and the speed sampling mode. In the uniform sampling mode shown in FIG. 25A, target agricultural items are selected from every row. In the speed sampling mode shown in FIG. 25B, target agricultural items are selected from every other row.

However, the uniform sampling mode and the speed sampling mode are not limited to the above features as long as the speed sampling mode samples fewer rows than the uniform sampling mode. For example, agricultural items may be sampled from every other row, every third row, every fourth row, etc. in the uniform sampling mode and sampled from every third row, every fourth row, every fifth row, etc. in the speed sampling mode.

According to a preferred embodiment of the present invention, a controller of an autonomous vehicle can be configured or programmed to automatically change between the uniform sampling mode and the speed sampling mode. For example, if the autonomous vehicle is performing uniform sampling and the controller determines that available energy to complete the uniform sampling is insufficient (e.g., due to low battery charge), the controller can be configured or programmed to automatically change to speed sampling mode.

Figure 26A:
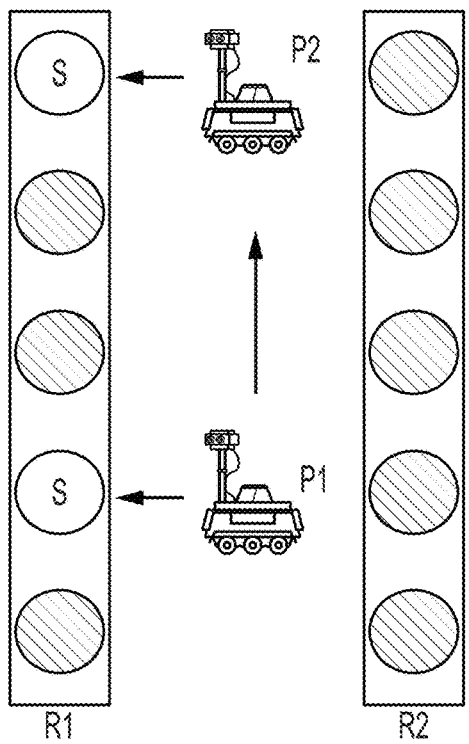
FIGS. 26A-26C show examples of autonomous vehicle control for agricultural item sampling according to preferred embodiments of the present invention.
Figure 26B:
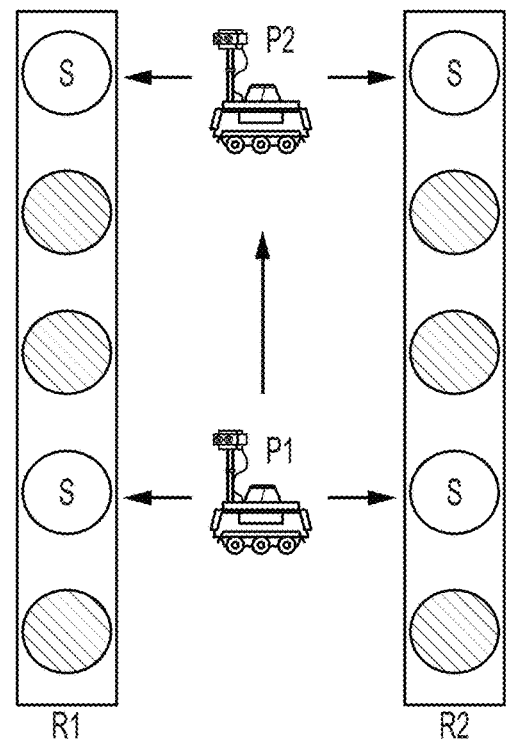
Figure 26C:
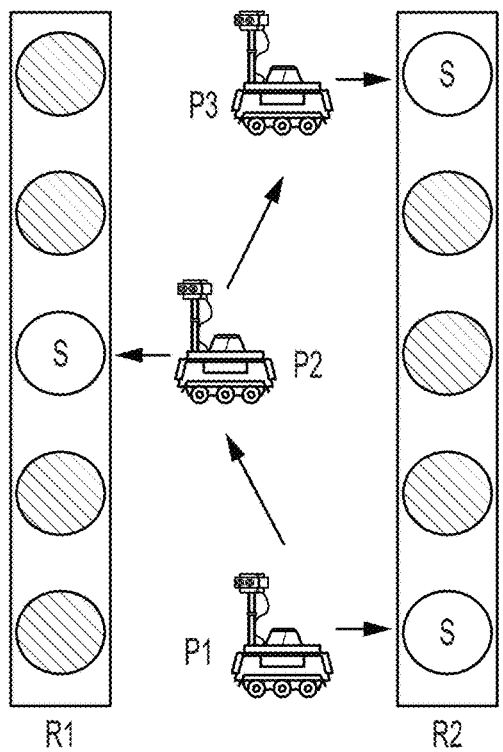

FIGS. 26A-26C show examples of autonomous vehicle control for agricultural item sampling according to preferred embodiments of the present invention. The examples shown in FIGS. 26A-26C can be applied to any of the uniform sampling mode, the speed sampling mode, and the random sampling mode.

As shown in FIG. 26A, an autonomous vehicle can be controlled to sample specific agricultural items S along only a first row R1 and not a second row R2 while the vehicle travels between two rows R1 and R2. That is, FIG. 26A shows that the autonomous vehicle stops and samples a single agricultural item S of the first row R1 at a first position P1, and then stops and samples another single agricultural item S of the first row R1 at a second position P1. However, as shown in FIGS. 26B and 26C, an autonomous vehicle can be controlled to sample specific agricultural items S along both the first row R1 and the second row R2 while the vehicle travels between two rows R1 and R2.

FIG. 26B shows that an autonomous vehicle can be controlled to stop at specific positions between the two rows R1 and R2 to sample an agricultural item S in each of the first row R1 and the second row R2. That is, FIG. 26B shows that the autonomous vehicle stops and samples an agricultural item S of each the first row R1 and the second row R2 at a first position P1, and then stops and samples another agricultural item S of each of the first row R1 and the second row R2 at a second position P1. The agricultural items S in each of the first row R1 and the second row R2 can be simultaneously sampled, for example, if the autonomous vehicle is equipped with two HSI cameras that respectively face each of the two rows R1 and R2. As another example, if the autonomous vehicle is equipped with only a single HSI camera, the single HSI camera can be rotated to sequentially sample agricultural items S in each of the first row R1 and the second row R2. The single HSI camera can be rotated, for example, by a rotation of the entire autonomous vehicle or by rotating a camera system mounted to the autonomous vehicle.

FIG. 26C shows that an autonomous vehicle can be controlled to stop at specific positions between the two rows R1 and R2 to alternatingly sample an agricultural item S in each of the first row R1 and the second row R2. That is, FIG. 26C shows that the autonomous vehicle stops and samples a single agricultural item S of the first row R1 at a first position P1, stops and samples another single agricultural item S of the second row R2 at a second position P2, and then stops and samples a further single agricultural item S of the first row R1 at a third position P3. The autonomous vehicle can be controlled to move in a zig-zag path as shown in FIG. 26C, for example, to maintain a distance of about 30 cm between an HSI camera of the autonomous vehicle and the agricultural item S to be sampled in each of the two rows R1 and R2.

The autonomous vehicle operations shown in FIGS. 26B and 26C can be implemented to reduce an overall distance that the autonomous vehicle travels to sample agricultural items in a target area, thereby providing a reduction in time spent to sample the target area. Furthermore, the autonomous vehicle operations shown in FIGS. 26B and 26C can be implemented, for example, if an autonomous vehicle is unable to turn between each row and implement the operations shown in FIG. 26A but is able to turn between every other row.

FIG. 27 shows an application display 600 according to a preferred embodiment of the present invention that includes task parameters for sampling agricultural items. The application display shown in FIG. 24 can be implemented with one or more of the cartesian arm system 100 shown in FIG. 1, the camera system 300 shown in FIGS. 9A-9C, and the camera system 400 shown in FIG. 16.

As shown in FIG. 27, the application display 600 can include a first region 610 indicating a particular agricultural item to be sampled, for example, a specific variety of grape. The particular agricultural item to be sampled can be set by a user, can be automatically set based upon previous sampling operation(s), or can be automatically determined based upon other information regarding the agricultural items to be sampled (e.g., quality score(s)).

As shown in FIG. 27, the application display 600 can further include a second region 620 in which sampling parameters can be set. The sampling parameters can be set by a user, can be automatically set based upon previous sampling operation(s), or can be automatically determined based upon other information regarding the agricultural items to be sampled (e.g., quality score(s)). The sampling parameters set in the second region 620 can be binary (e.g., "on" or "off") or can be set according to a threshold value or the like.

As shown in FIG. 27, the application display 600 can also include a third region 630 in which a sampling rate and a sampling mode can be set. For example, described above with respect to FIGS. 23 to 26C, the sampling mode can be set as a uniform sampling mode, a speed sampling mode, or a random sampling mode. The sampling rate and the sampling mode can be set by a user, can be automatically set based upon previous sampling operation(s), or can be automatically determined based upon other information regarding the agricultural items to be sampled (e.g., quality score (s)).

Figure 28:
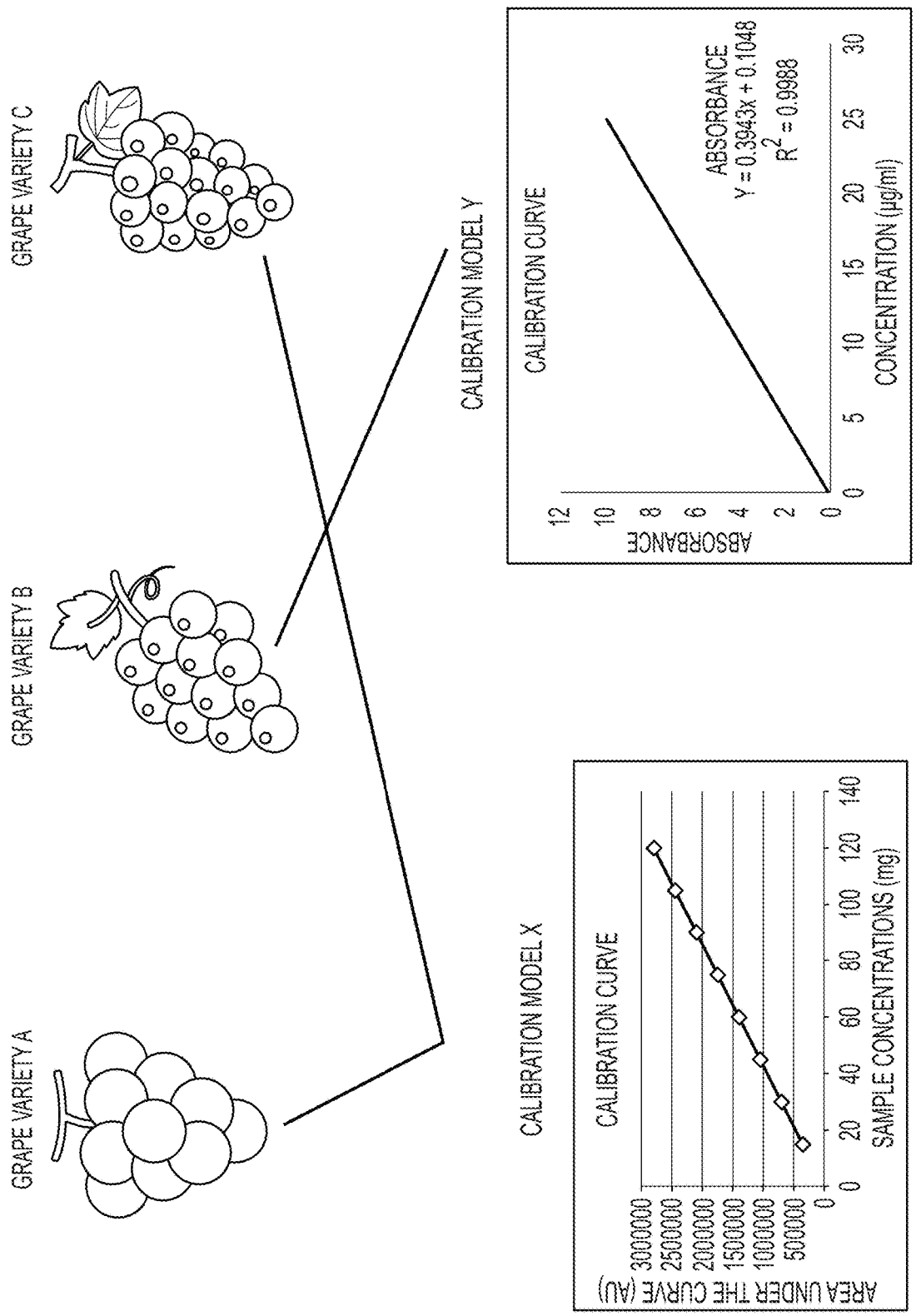
FIG. 28 shows an example of selecting calibration curves for grape varieties according to a preferred embodiment of the present invention.

FIG. 28 shows an example of selecting calibration curves for grape varieties according to a preferred embodiment of the present invention.

Different varieties of agricultural items can require different calibration curves to accurately determine quality scores. For example, as shown in FIG. 28, a grape variety A and a grape variety C may share a same calibration curve provided by a calibration model X, whereas a grape variety B may require a different calibration curve provided by a calibration model Y. Accordingly, by setting a particular agricultural item to be sampled in the first region 610 of the display 600, for example, a specific variety of grape, a calibration curve can be selected.

However, calibration curves can be selected according to additional factors. For example, the sampling parameters set in the second region 620 the application display 600 can be used by a controller or the like to select a calibration curve.

In addition, calibration curves may be selected according to a geographic region, for example, a country, state, or province in which the grapes are grown (e.g., California Zinfandel and Italian Zinfandel may have different calibration curves). Furthermore, calibration curves can be selected according to more specific geographic locations, for example, a particular city or county, or even a particular field.

The calibration curves can be constructed according to the process 3000 described above with respect to FIG. 8.

Figure 29:
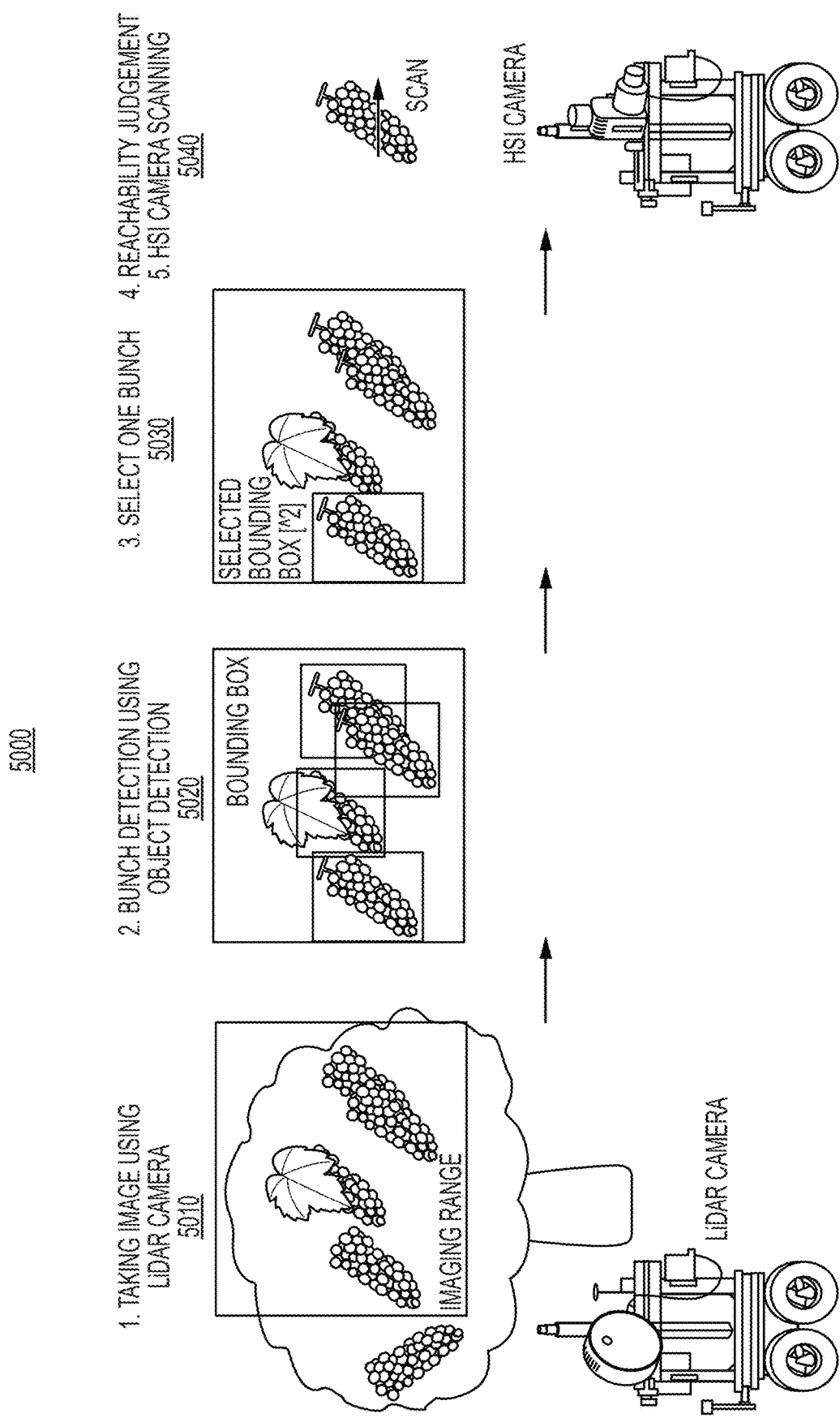
FIG. 29 shows a process of determining a grape bunch for quality measurement according to a preferred embodiment of the present invention.

FIG. 29 shows a process 5000 of determining a grape bunch for quality measurement according to a preferred embodiment of the present invention. The process 5000 shown in FIG. 29 can be implemented with one or more of the cartesian arm system 100 shown in FIG. 1, the camera system 300 shown in FIGS. 9A-9C, and the camera system 400 shown in FIG. 16.

As shown in FIG. 29, the process 5000 begins with a first operation 5010 of capturing a first image of one or more grape bunches. The first image can be captured by a depth camera such as a LIDAR camera as shown in FIG. 29, or can be captured by an RGB camera, a combined RGB camera and depth camera, a stereo camera, and the like.

After capturing the first image, the process 5000 proceeds to operation 5020 in which bunch detection is performed using object detection. For example, operation 5020 can use the object detection model 106 described above with respect to FIG. 13 to detect/identify the one or more grape bunches. Accordingly, operation 5020 can output a feature image that includes bounding boxes that surround the grape bunches shown in the first image.

After detecting the grape bunches in the first image, the process 5000 proceeds to operation 5030 in which one of the grape bunches detected/identified in the first image is selected. The selected grape bunch can be determined according to a combined score that is calculated for each of the one or more grape bunches based upon a confidence score, a depth score, a the area score. The combined score can be determined according to the process described above with respect to FIG. 4E.

In addition to using the combined score, operation 5030 can also consider sampling parameters, for example, the sampling parameters set in the second region 620 of the application display 600 shown in FIG. 27. That is, the operation 5030 to detect/identify one of the group bunches in the first image can select a grape bunch that does not have undesirable characteristics, for example, dryness, spider webs, mold, sunburn, and the like.

After selecting a grape bunch from the first image, the process 5000 proceeds to operation 5040 in which a second image of the selected grape bunch is captured if the selected grape bunch is reachable by an HSI camera.

Figure 30:
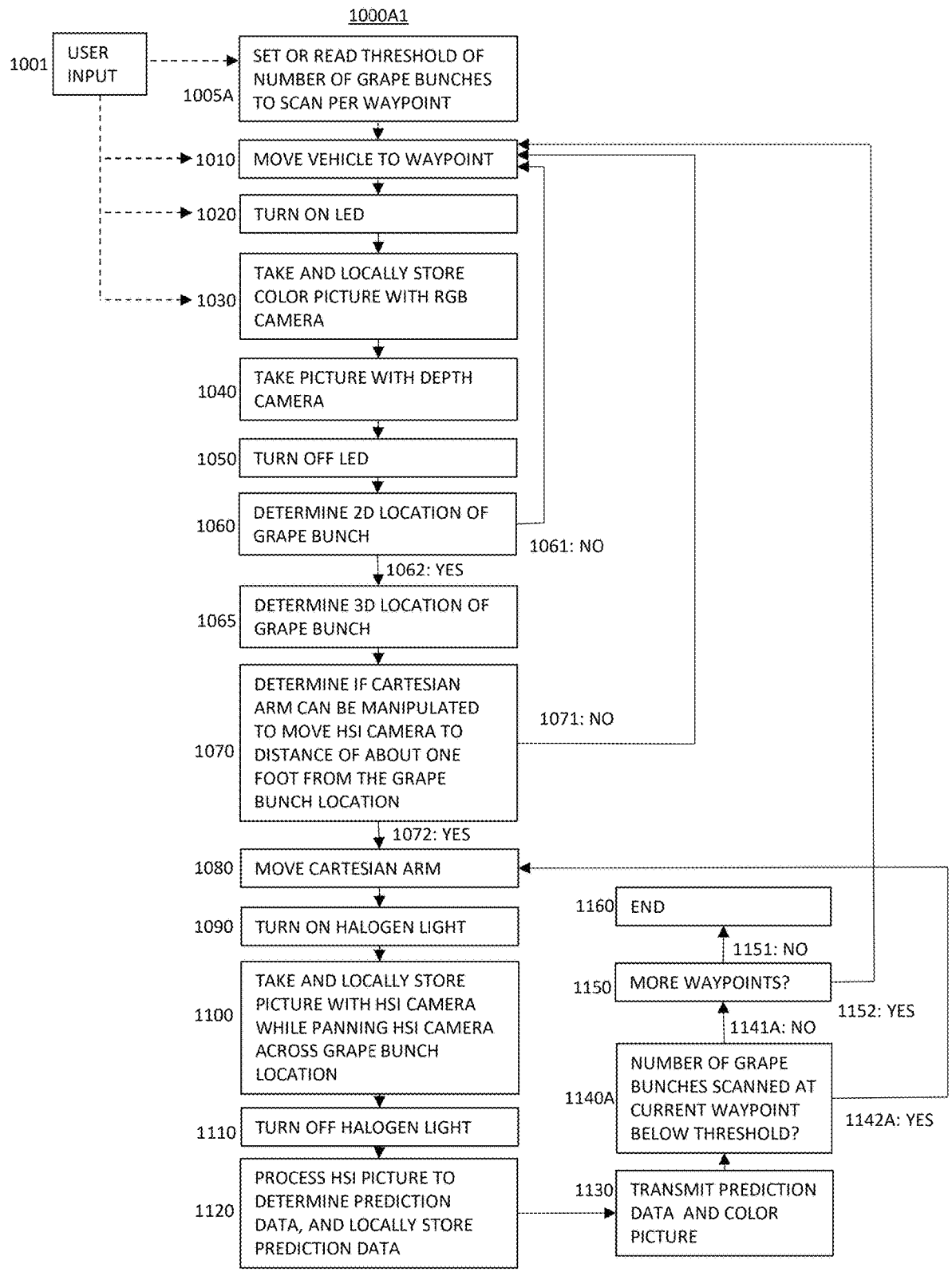
FIG. 30 is a flowchart showing processes performed by a vehicle or a cartesian arm system according to preferred embodiments of the present invention.

FIG. 30 is a flowchart showing processes performed by a vehicle or a cartesian arm system according to preferred embodiments of the present invention. In particular, FIG. 30 shows a modified process 1000A1 in which only a predetermined portion of grape bunches is sampled and in which a user input 1001 is provided. Detailed description of operations shown in FIG. 30 that are the same as those shown in FIGS. 4A and 4B are omitted for conciseness. The modified process 1000A1 shown in FIG. 30 can be implemented with one or more of the cartesian arm system 100 shown in FIG. 1, the camera system 300 shown in FIGS. 9A-9C, and the camera system 400 shown in FIG. 16.

As shown in FIG. 30, the modified process 1000A1 can further include an operation 1001 of receiving a user input. As a first example, the user input can be an initial operation of the modified process 1000A1, for example, when performing the operation 1005A of setting or reading a predetermined threshold of the number of grape bunches to be scanned per waypoint.

As a second example, the user input in operation 1001 can be provided after the operation 1005A of setting or reading a predetermined threshold of the number of grape bunches to be scanned per waypoint, but before the vehicle begins to move a waypoint in operation 1010.

As a third example, the user input in operation 1001 can be provided at any time prior to operation 1030 of taking color image (e.g., two-dimensional color image) with the RGB camera.

The user input in operation 1001 can include, for example, an input of a particular agricultural item to be sampled as shown in the first region 610 of the display 600 of FIG. 27, such as a specific variety of grape. Alternatively or in addition, the user input in operation 1001 can include, for example, the sampling parameters shown in the second region 620 of the application display 600 shown in FIG. 27. Alternatively or in addition, the user input in operation 1001 can include, for example, a sampling rate and/or a sampling mode as shown in the third region 630 of the application display 600 shown in FIG. 27. Accordingly, a user's input for the operation of, for example, the cartesian arm system 100 shown in FIG. 1, the camera system 300 shown in FIGS. 9A-9C, and the camera system 400 can be provided prior to any operations that may be affected by the user's input.

In a preferred embodiment of the present invention, a portion or an entirety of the controller 355 and/or the functional units or blocks thereof as described herein with respect to the various preferred embodiments of the present invention can be implemented in one or more circuits or circuitry, such as an integrated circuit(s) or as an LSI (large scale integration). For example, the controller 355 can include one or more circuits or circuitry such as a microprocessor, a microcontroller, a multi-core processor, a central processing unit (CPU), a graphics processing unit (GPU), and a superscalar processor, for example, in forms such as semiconductor integrated circuit chip packages, semiconductor integrated circuit modules, and single-board computers that can operate in connection with built-in or external memory. Each functional unit or block of each of the controller 355 may be individually made into an integrated circuit chip. Alternatively, a portion or an entirety of the functional units or blocks of each of the controller 355 may be integrated and made into an integrated circuit chip. Additionally, the method of forming a circuit or circuitry defining each of the controller 355 is not limited to LSI, and an integrated circuit may be implemented by a dedicated circuit or one or more general-purpose processor or controller that is specifically programed to define a special-purpose processor or controller to perform one or more of the functions, operations, steps, or processes disclosed herein. Further, if a technology or technologies for forming an integrated circuit, which replaces LSI, arises as a result of advances in semiconductor technology, an integrated circuit formed by that technology may be used.

Furthermore, a program which is operated in each of the controller 355 and/or other elements of various preferred embodiments of the present invention, is a program (e.g., a program causing a computer to perform a function or functions, operations, steps, or processes) controlling a controller, in order to realize one or more functions, operations, steps, or processes of the various preferred embodiments according to the present invention, including each of the various circuits or circuitry described herein and recited in the claims. Further, information which is handled by the controller may be temporarily accumulated in a RAM at the time of the processing. Thereafter, the information is stored in various types of circuitry in the form of ROMs and HDDs, and is read out by circuitry within, or included in combination with, the controller 355 as necessary, and modification or write-in may be performed thereto. Examples of a recording medium storing the program or programs can include integrated circuits on a same semiconductor chip that defines the controller 355, integrated circuits formed on a different semiconductor chip from the controller 355, or various storage media that can communicate data and address signals via a network bus. As a recording medium storing the program or programs, any one of, or a combination of, a semiconductor medium (for example, the ROM, a nonvolatile memory card or the like), an optical recording medium (for example, a DVD, an MO, an MD, a CD, a BD or the like), and a magnetic recording medium (for example, a magnetic tape, a flexible disc or the like) may be used. Moreover, by executing the loaded program, the functions, operations, steps, or processes of the various preferred embodiments of the present invention are not only realized, but the functions, operations, steps, or processes of preferred embodiments of the present invention may be realized by processing the loaded program in combination with an operating system or other application programs, based on an instruction of the program.

Moreover, in a case of being distributed in a market, the program or programs can be distributed by being stored in a portable recording medium, or the program or programs can be transmitted to a server computer which is connected through a network such as the Internet. In this case, a storage device of the general purpose or special purpose computer is also included in preferred embodiments of the present invention. In addition, in the preferred embodiments described above, a portion or an entirety of the various functional units or blocks may be realized as an LSI which is typically an integrated circuit. Each functional unit or block of the controller may be individually chipped, or a portion thereof, or the whole thereof may be chipped by being integrated. In a case of making each functional block or unit as an integrated circuit, an integrated circuit controller that controls the integrated circuits, may be added.

Additionally, the method for making an integrated circuit is not limited to the LSI, and may be realized by a single-purpose circuit or a general-purpose processor that is programmable to perform the functions described above to define a special-purpose computer. Moreover, in a case of an appearance of a technology for making an integrated circuit which replaces the LSI due to an advance of a semiconductor technology, it is possible to use an integrated circuit depending on the technology.

Finally, it should be noted that the description and recitation in claims of this patent application referring to "CPU", "control unit", "computer", "processor", "microprocessor", "controller", "circuit", or "circuitry" is in no way limited to an implementation that is hardware only, and as persons of ordinary skill in the relevant art would know and understand, such descriptions and recitations of "CPU", "control unit", "computer", "processor", "microprocessor", "controller", "circuit", or "circuitry" include combined hardware and software implementations in which the controller, circuit, or circuitry is operative to perform functions and operations based on machine readable programs, software or other instructions in any form that are usable to operate the controller, circuit, or circuitry.

The processes and operations described herein are preferably performed at night so that a varying spectrum of light from the sun, which can vary according to weather conditions and the like, does not influence the predetermined spectrum of light emitted by the halogen light.

The processes and operations described herein are described with respect to an autonomous vehicle that is able to automatically move between waypoints. However, a vehicle and/or cameras that are manually operated by a user can be implemented within the scope of the preferred embodiments of the present invention.

The processes and operations described herein are described with respect to predicting quality parameters of grapes. However, the processes and operations described herein can be applied to any predetermined objects, including other agricultural products.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:

1. A quality measurement system comprising:
    a first camera;
    a second camera; and
    a controller, wherein
    the controller is configured or programmed to control the first camera to acquire a first image that includes a plurality of agricultural items;
    the controller is configured or programmed to determine, from the first image, one of the plurality of agricultural items that is suitable for measuring quality;
    the controller is configured or programmed to control the second camera to acquire measurement data of the one of the plurality of agricultural items;
    the controller is configured or programmed to store a plurality of estimation models for calculating at least one quality score based upon the measurement data acquired by the second camera;
    the controller is configured or programmed to select one of the plurality of estimation models according to the one of the plurality of agricultural items; and
    the controller is configured or programmed to calculate the at least one quality score of the one of the plurality of agricultural items based upon the selected one of the plurality of estimation models.

2. The quality measurement system according to claim 1, wherein the controller is configured or programmed to select the one of the plurality of estimation models according to a variety of the one of the plurality of agricultural items.

3. The quality measurement system according to claim 1, wherein:
    the one of the plurality of agricultural items is a grape bunch, and
    the controller is configured or programmed to store predetermined relationships between plurality of estimation models and grape varieties.

4. The quality measurement system according to claim 1, wherein at least one of the plurality of estimation models is associated with at least two grape varieties.

5. The quality measurement system according to claim 1, wherein each of the plurality of estimation models is a calibration curve that associates wavelength intensity with the at least one quality score.

6. The quality measurement system according to claim 1, wherein the at least one quality score includes one or more of Brix, pH, and titratable acidity (TA).

7. The quality measurement system according to claim 1, wherein:
    the first camera is a stereo camera, and
    the second camera is an HSI (hyperspectral imaging) camera.

8. The quality measurement system according to claim 1, wherein the controller is configured or programmed to select the one of the plurality of estimation models according to a location of the quality measurement system.

9. A vehicle comprising:
    the quality measurement system according to claim 1, wherein
    the controller is configured or programmed to control movement of the vehicle.

10. The vehicle according to claim 9, wherein the controller is configured or programmed to control the vehicle to stop and remain stationary while the first camera acquires the first image.

11. The vehicle according to claim 9, wherein the controller is configured or programmed to control the vehicle to stop and remain stationary while the second camera acquires the second image.

12. The vehicle according to claim 9, further comprising at least one slider that is configured to move the second camera.

13. The vehicle according to claim 12, wherein the controller is configured or programmed to control the at least one slider to move the second camera while the vehicle is stationary.

14. An agricultural system comprising:
    the vehicle according to claim 9; and
    a display device that is operable by a user.

15. The agricultural system according to claim 14, wherein the controller is configured or programmed to determine the one of the plurality of agricultural items that is suitable for measuring quality in response to an input by the user of the display device.

16. The agricultural system according to claim 14, wherein the display device is configured to display a selection of varieties of the plurality of agricultural items.

17. The agricultural system according to claim 14, wherein the display device is configured to display selectable parameters for measuring the at least one quality score.

18. The agricultural system according to claim 14, wherein the controller is configured or programmed to receive operational parameters input by the user of the display device prior to controlling the vehicle to begin movement to the plurality of agricultural items.

* * * * *